US011825820B2

(12) United States Patent
Trifiro et al.

(10) Patent No.: US 11,825,820 B2
(45) Date of Patent: Nov. 28, 2023

(54) POLY-GLUTAMINE ANDROGEN RECEPTOR KNOCK-IN MOUSE MODELS, REAGENTS AND METHODS

(71) Applicants: Mark Trifiro, Montreal (CA); Miltiadis Paliouras, Laval (CA); Lenore K. Beitel, Montreal (CA); Carlos Alvarado, Dollard des Ormeaux (CA)

(72) Inventors: Mark Trifiro, Montreal (CA); Miltiadis Paliouras, Laval (CA); Lenore K. Beitel, Montreal (CA); Carlos Alvarado, Dollard des Ormeaux (CA)

( * ) Notice: Subject to any disclaimer, the term of this patent is extended or adjusted under 35 U.S.C. 154(b) by 1328 days.

(21) Appl. No.: 15/940,387

(22) Filed: Mar. 29, 2018

(65) Prior Publication Data
US 2018/0288985 A1 Oct. 11, 2018

Related U.S. Application Data

(60) Provisional application No. 62/479,754, filed on Mar. 31, 2017.

(51) Int. Cl.
A01K 67/027 (2006.01)
C07K 14/72 (2006.01)

(52) U.S. Cl.
CPC ........ A01K 67/0278 (2013.01); C07K 14/721 (2013.01); A01K 2217/072 (2013.01); A01K 2217/203 (2013.01); A01K 2227/105 (2013.01); A01K 2267/035 (2013.01); A01K 2267/0393 (2013.01)

(58) Field of Classification Search
CPC .......... A01K 67/0278; A01K 2217/072; A01K 2217/203; A01K 2227/105; A01K 2267/035; A01K 2267/0393; C07K 14/721
See application file for complete search history.

(56) References Cited

PUBLICATIONS

Alvarado et al. "Metabolic X Syndrome is an AR-CAG Tract Disorder?" Endocrine Reviews, (2016) vol. 37, No. 2, Supp. Supplement 1. Abstract No. SUN-700 (Year: 2016).*
Albertelli, M. A. "Genetic variation in the androgen receptor impacts prostate cancer initiation and progression in the humanized AR mouse." Order No. 3253209 University of Michigan, 2007 Ann ArborProQuest. (Year: 2007).*
Krishnaswamy et al. "South Indian men with reduced CAG repeat length in the androgen receptor gene have an increased risk of prostate cancer" Journal of Human Genetics vol. 51, pp. 254-257 (2006) (Year: 2006).*
Lieberman AP., et al. The androgen receptor's CAG/glutamine tract in mouse models of neurological disease and cancer. J Alzheimers Dis 2008; 14:247-55.
Mousavi G. Generating vectors for production of transgenic mouse models to investigate the role of the androgen receptor and its CAG repeat in human prostate cancer [Thesis (M Sc )]; 2005.
Staels B, et al. Hepatoprotective effects of the dual peroxisome proliferator-activated receptor alpha/delta agonist, GFT505, in rodent models of nonalcoholic fatty liver disease/nonalcoholic steatohepatitis. Hepatology 2013;58:1941-52.
Fukunaga T, et al. An insulin-sensitizing thiazolidinedione, which minimally activates PPARgamma, does not cause bone loss. J Bone Miner Res 2015;30:481-8.
Hogan B. Manipulating the mouse embryo : a laboratory manual. 2nd ed. Plainview, N.Y.: Cold Spring Harbor Laboratory Press; 1994.
Mhatre AN., et al. Reduced transcriptional regulatory competence of the androgen receptor in X-linked spinal and bulbar muscular atrophy. Nature genetics 1993;5:184-8.
Southwell J., et al. An investigation into CAG repeat length variation and N/C terminal interactions in the T877A mutant androgen receptor found in prostate cancer. The Journal of steroid biochemistry and molecular biology 2008;111:138-46.
Alvarado C., et al. Somatic mosaicism and cancer: a micro-genetic examination into the role of the androgen receptor gene in prostate cancer. Cancer research 2005;65:8514-8.
Sircar K., et al. Androgen receptor CAG repeat length contraction in diseased and non-diseased prostatic tissues. Prostate Cancer Prostatic Dis 2007;10:360-8.
Gottlieb B., et al. Making sense of intratumor genetic heterogeneity: altered frequency of androgen receptor CAG repeat length variants in breast cancer tissues. Human mutation 2013;34:610-8.
Hossain D, et al. Significance of the TMPRSS2:ERG gene fusion in prostate cancer. BJU international 2013;111:834-5.
Loomba R, et al. The ASK1 inhibitor selonsertib in patients with nonalcoholic steatohepatitis: A randomized, phase 2 trial. Hepatology 2017.
Nickerson ML, et al. Somatic alterations contributing to metastasis of a castration-resistant prostate cancer. Human mutation 2013;34:1231-41.
Wu X, et al. Current mouse and cell models in prostate cancer research. Endocrine-related cancer 2013;20:R155-70.
Nelson WG, et al. The role of inflammation in the pathogenesis of prostate cancer. The Journal of urology 2004;172:S6-11; discussion S-2.
Vignozzi L, et al. Prostate cancer: intriguing data on inflammation and prostate cancer. Nat Rev Urol 2014;11:369-70.

(Continued)

Primary Examiner — Titilayo Moloye
(74) Attorney, Agent, or Firm — BENOIT & COTE INC.

(57) ABSTRACT

A knock-in non-human mammal comprising a recombinant androgen receptor (AR) cassette containing an exogenous human polyglutamine (polyQ) tract encoding sequence in exon 1, wherein the human polyQ tract encoding sequence is stably integrated into the genome of the animal. Also provided are recombinant cells, fertilized eggs and tissues. The resulting animal displays a wide range of phenotypes, best characterized as Metabolic Syndrome and can be used in screening and other assays.

17 Claims, 15 Drawing Sheets
Specification includes a Sequence Listing.

(56) References Cited

PUBLICATIONS

De Nunzio, et al. The correlation between metabolic syndrome and prostatic diseases. European urology 2012;61:560-70.

Hwang B., et al. Pyruvate dehydrogenase kinase isoenzyme 4 (PDHK4) deficiency attenuates the long-term negative effects of a high-saturated fat diet. The Biochemical journal 2009;423:243-52.

Hwang B, et al. Additive effects of clofibric acid and pyruvate dehydrogenase kinase isoenzyme 4 (PDK4) deficiency on hepatic steatosis in mice fed a high saturated fat diet. The FEBS journal 2012;279:1883-93.

Ande SR, et al. Prohibitin-induced, obesity-associated insulin resistance and accompanying low-grade inflammation causes NASH and HCC. Sci Rep 2016;6:23608.

Nakatsu D, et al. L-cysteine reversibly inhibits glucose-induced biphasic insulin secretion and ATP production by inactivating PKM2. Proceedings of the National Academy of Sciences of the United States of America 2015;112:E1067-76.

Pillai R, et al. Aryl hydrocarbon receptor nuclear translocator/hypoxia-inducible factor-1{beta} plays a critical role in maintaining glucose-stimulated anaplerosis and insulin release from pancreatic {beta}-cells. The Journal of biological chemistry 2011;286:1014-24.

Pardo V, et al. Role of hepatocyte S6K1 in palmitic acid-induced endoplasmic reticulum stress, lipotoxicity, insulin resistance and in oleic acid-induced protection. Food and chemical toxicology : an international journal published for the British Industrial Biological Research Association 2015,80:298-309.

Kurikawa N, et al. A novel inhibitor of stearoyl-CoA desaturase-1 attenuates hepatic lipid accumulation, liver injury and inflammation in model of nonalcoholic steatohepatitis. Biol Pharm Bull 2013;36:259-67.

Pires KM, et al. Treatment with a SOD mimetic reduces visceral adiposity, adipocyte death, and adipose tissue inflammation in high fat-fed mice. Obesity (Silver Spring) 2014;22:178-87.

\* cited by examiner

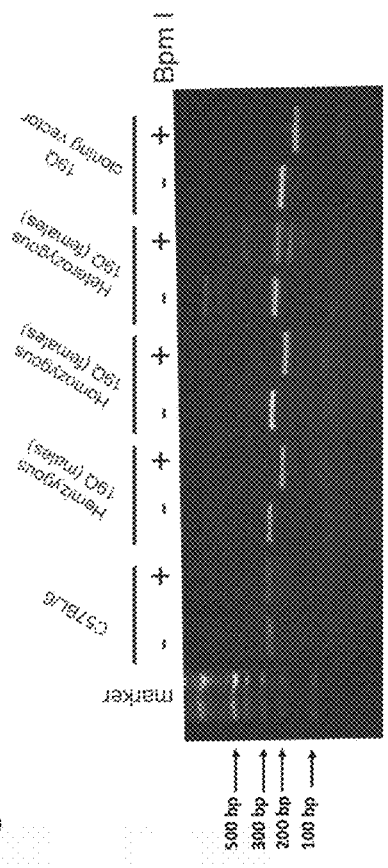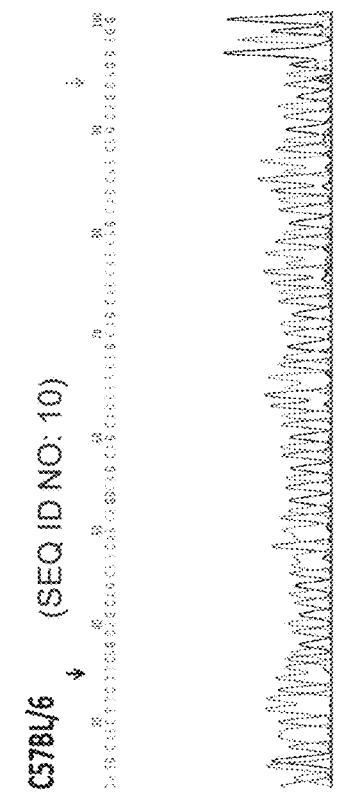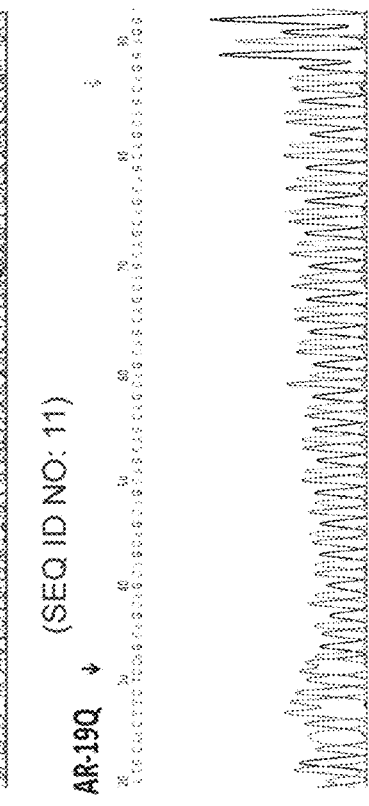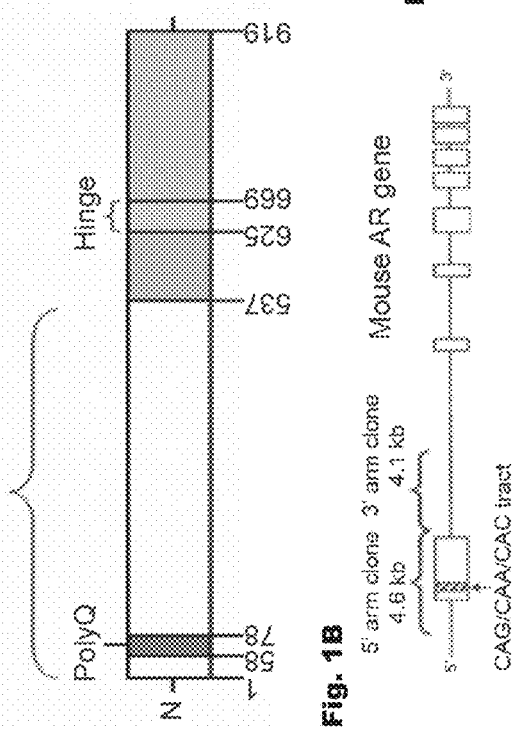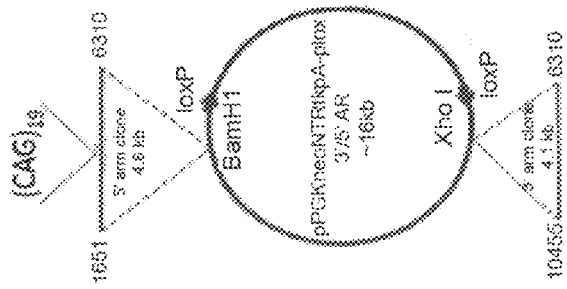

(SEQ ID NO:12)  0 CAG (SEQ ID NO:14) 39 CAG (SEQ ID NO:13)  40 CAG/CAA

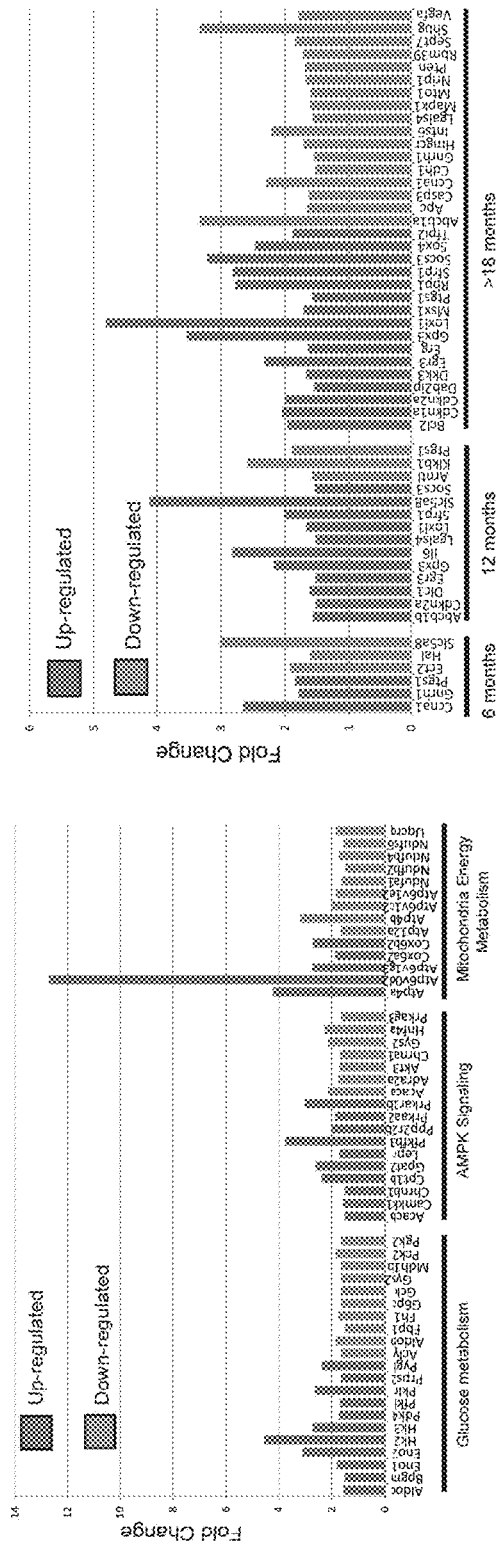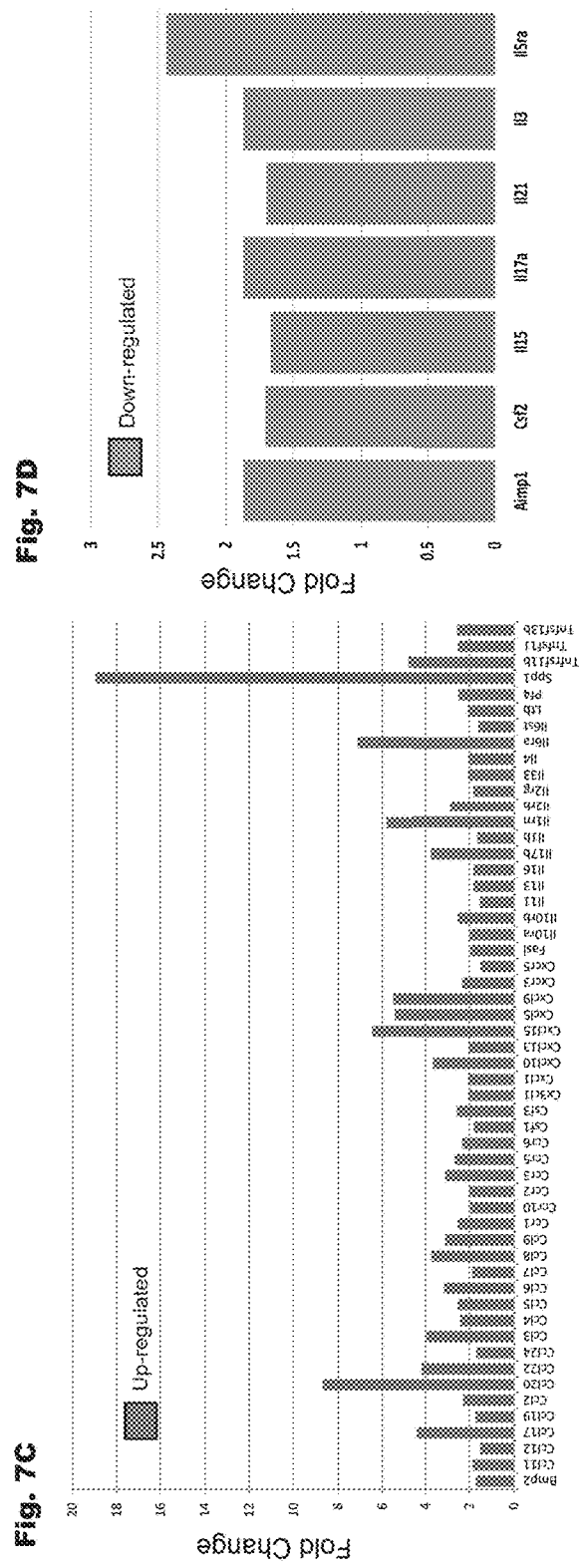

Fig. 11A
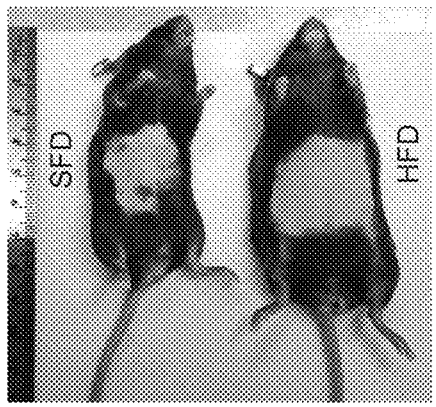
Fig. 11B
Fig. 11C
Fig. 11D
Fig. 11E
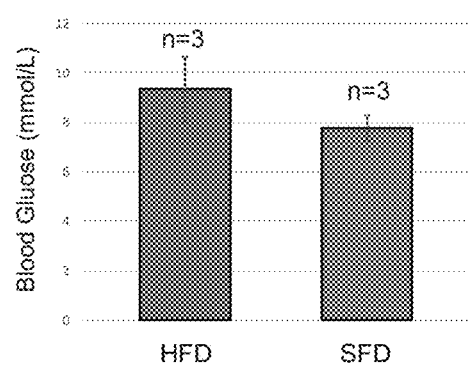
Fig. 11F
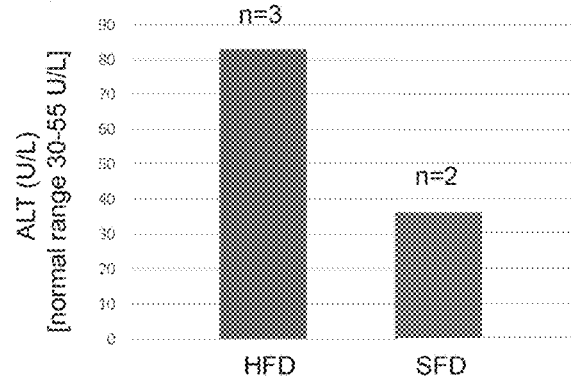

Fig. 13

Mouse AR exon 1/19Q plus junction/intron 1     (SEQ ID NO: 8)

```
1                                                             60
ATGGAGGTGC AGTTAGGGCT GGGAAGGGTC TACCCACGGC CCCCATCCAA GACCTATCGA
61                                                           120
GGAGCGTTCC AGAATCTGTT CCAGAGCGTG CGCGAAGCGA TCCAGAACCC GGGCCCCAGG
121                                                          180
CACCCTGAGG CCGGTAACAT AGCACCTGCC GGCGCCTGTT TACAGCAGAG GCAGGAGACT
181                                                          240
AGCCCCCGGC GGCGGCGGCG GCAGCAGCAC ACTGAGGATG GTTCTCCTCA GCCCACATC
241                                                          300
AGAGGCCCCA CAGGCTACCT GGCCCTGGAG GAGGAACAGC AGCCTTCACA GCAGCAGGCA
301                                                          360
GCCTCCGAGG GCCACCCTGA GAGCAGCTGC CTCCCCGAGC CTGGGCGGC CACCGCTCCT
361                                                          420
GGCAAGGGGC TGCCGCAGCA GCCACCAGCT CCTCCAGATC AGGATGACTC AGCTGCCCCA
421                                                          480
TCCACGTTGT CCCTGCTGGG CCCCACTTTC CCAGGCTTAA GCAGCTGCTC CGCCGACATT
481                                                          540
AAAGACATTT TGAACGAGGC CGGCACCATG CAACTTCTCC AGCAGCAGCA GCAGCAGCAG
541                                                          600
CAGCAGCAGC AGCAGCAGCA GCAGCAGCAG CAGCAGGAGG TAATCTCCGA AGGCAGCAGC
601                                                          660
GCAAGAGCCA GGGAGGCCAC GGGGCTCCC TCTTCCTCCA AGGATAGTTA CCTAGGGGGC
661                                                          720
AATTCAACCA TATCTGACAG TGCCAAGGAG TTGTGTAAAG CAGTGTCTGT GTCCATGGGA
721                                                          780
TTGGGTGTGG AAGCATTGGA ACATCTGAGT CCAGGGGAAC AGCTTCGGGG AGATTGCATG
781                                                          840
TACGCGTCGC TCCTGGAGG TCCACCCGCG GTGCGTCCGA CTCCTTGTGC GCCGCTGCCC
841                                                          900
GAATGCAAAG GTCTTCCCCT GGACGAAGGC CCAGGCAAAA GCACTGAAGA GACTGCTGAG
901                                                          960
TATTCCTCTT TCAAGGGAGG TTACGCCAAA GGATTGGAAG GTGAGAGCTT GGGGTGCTCT
961                                                         1020
GGCAGCAGTG AAGCAGGTAG CTCTGGGACA CTTGAGATCC CGCCTCTCT GTCTCTTAT
1021                                                        1080
AAATCTGGAG CACTAGACGA GGCAGCAGCA TACCAGAATC GCGACTACTA CAACTTTCCG
1081                                                        1140
CTGGCTCTGT CCGGGCCGCC GCACCCCCG CCCCCTACCC ATCCACACGC CCGTATCAAG
1141                                                        1200
CTGGAGAACC CATTGGACTA CGGCAGCGCC TGGGCTGCGG CGGCAGCGCA ATGCCGCTAT
1201                                                        1260
GGGGACTTGG GTAGTCTACA TGGAGGGAGT GTAGCCGGGC CCAGCACTGG ATCGCCCCA
1261                                                        1320
GCCACCACCT CTTCTTCCTG GCATACTCTC TTCACAGCTG AAGAAGGCCA ATTATATGGG
```

Fig. 13 Cont.

```
1321                                                                  1380
      CCAGGAGGCG GGGGCGGCAG CAGCAGCCCA AGCGATGCCG GGCCTGTAGC CCCCTATGGC
1381                                                                  1440
      TACACTCGGC CCCCTCAGGG GCTGACAAGC CAGGAGAGTG ACTACTCTGC CTCCGAAGTG
1441                                                                  1500
      TGGTATCCTG GTGGAGTTGT GAACAGAGTA CCCTATCCCA GTCCCAATTG TGTCAAAAGT
1501                                                                  1560
      GAAATGGGAC CTTGGATGGA GAACTACTCC GGACCTTATG GGACATGCG GTAAGTTTAT
1561                                                                  1620
      ACTAAAAATG CCTCCTTTTG ACCAAGGGCA CAGAGTAAGC AGTTTGCATT TTGTGGGATC
1621                                                                  1680
      TAGGGACTCC CGCCCAATAG AACAATCGGA AGGATCCTAA GTCAGCTCAG ACTAGTTCTA
1681                                                                  1740
      TAGGAAGGTC TGTCCTACAT CTGGAGCCCT CGTGGGGACT GTCATCTTGT GAAATGTTCC
1741                                                                  1800
      GCCTAAGCCC AGGGAATCTT TGCTGCGCTC CGGGGTGCTA ATACGTGCTC TTTGAGATTC
1801                                                                  1860
      CCCTCCAATT CCCCTAGCTT TCTAAACTCC TCCATTAAGA TCCACTAGTA ACGGCCGCCA
1861                                                                  1920
      GTGTGCTGGA ATTCTGCAGA TGATCCCCG GGCTGCAGGA ATTCGATATC AAGCTTATCG
1921                                                                  1980
      ATACCGTCGA GGAATTCCGA TCATATTCAA TAACCCTTAA TATAACTTCG TATAATGTAT
1981                                                                  2040
      GCTATACGAA GTTATTAGGT CCCTCGACGA GCTCGGATCT TTCTGATATT TCAAATCCTA
2041                                                                  2100
      TGAGTTCCAA ACTTAAATCA ATTGCATGGG CCATTTTCAG AAATGACGCC TGTAAGCTCT
2101                                                                  2160
      TCACGGTTTT TCATTCTTTT CCTCAAAGTT CTGGAAACAC GATCAGACAT GTAGGGAGTT
2161                                                                  2220
      TCTTGTCTTT GGGTCTGTTG GTAATCACCT TCCAGACCCG TGAAGTGAAT GGTCTTGGCA
2221                                                                  2280
      TAAGAAAAGG GAAATAAAAG CAGAAACCTG ATTTTCGGCC CGCATCCTTC AAAGAGAGAT
2281                                          2320
      AATAGAATTC TCAATTCTCC TAGAAAGAAA AGCCGCATCT -----------
```

Staring at Nucleotide 1

CAG sequence: 520-576 (underlined)
End of mouse exon 1: 1550
Intron mouse 5' arm: 1551-1838
pCDN3 vector: 1839-1881
ploxneo vector sequence: 1882-1995 (5' loxp sequence contained: 1962-1995)
3'loxp sequence: 1996-2008 (contains XhoI site: 2003-2008)
pCDN3 vector 3' arm: 2009-2018
rest is mouse intron DNA and mouse sequence: 2019-

Fig. 14

Exon 1 Sequence of mouse Androgen receptor with a 19 CAG tract

SEQ ID NO: 9

ATGGAGGTGCAGTTAGGGCTGGGAAGGGTCTACCCACGGCCCCCATCCAAGACCTATCGA
GGAGCGTTCCAGAATCTGTTCCAGAGCGTGCGCGAAGCGATCCAGAACCCGGGCCCCAGG
CACCCTGAGGCCGCTAACATAGCACCTCCCGGCGCCTGTTTACAGCAGAGGCAGGAGACT
AGCCCCCGGCGGCGGCGGCGGCAGCAGCACACTGAGGATGGTTCTCCTCAAGCCCACATC
AGAGGCCCCACAGGCTACCTGGCCCTGGAGGAGGAACAGCAGCCTTCACAGCAGCAGGCA
GCCTCCGAGGGCCACCCTGAGAGCAGCTGCCTCCCCGAGCCTGGGGCGGCCACCGCTCCT
GGCAAGGGGCTGCCGCAGCAGCCACCAGCTCCTCCAGATCAGGATGACTCAGCTGCCCCA
TCCACGTTGTCCCTGCTGGGCCCCACTTTCCCAGGCTTAAGCAGCTGCTCCGCCGACATT
AAAGACATTTTGAACGAGGCCGGCACCATGCAACTTCTT<u>CAGCAGCAGCAACAACAGCAG</u>
<u>CAGCACCAACAGCAGCACCAACAGCACCAACAGCAGCAG</u>GAGGTAATCTCCGAAGGCAGC
AGCGCAAGAGCCAGGGAGGCCACGGGGCTCCCTCTTCCTCCAAGGATAGTTACCTAGGG
GGCAATTCAACCATATCTGACAGTGCCAAGGAGTTGTGTAAAGCAGTGTCTGTGTCCATG
GGATTGGGTGTGGAAGCATTGGAACATCTGAGTCCAGGGGAACAGCTTCGGGGAGACTGC
ATGTACGCGTCGCTCCTGGGAGGTCCACCCGCGGTGCGTCCACTCCTTGTGCGCCGCTG
CCCGAATGCAAAGGTCTTCCCCTGGACGAAGGCCCAGGCAAAAGCACTGAAGAGACTGCT
GAGTATTCCTCTTTCAAGGGAGGTTACGCCAAAGGATTGGAAGGTGAGAGCTTGGGGTGC
TCTGGCAGCAGTGAAGCAGGTAGCTCTGGGACACTTGAGATCCCGTCCTCTCTGTCTCTG
TATAAATCTGGAGCACTAGACGAGGCAGCAGCATACCAGAATCGCGACTACTACAACTTT
CCGCTGGCTCTGTCCGGGCCGCCGCACCCCCCGCCCCCTACCCATCCACACGCCCGTATC
AAGCTGGAGAACCCATTGGACTACGGCAGCGCCTGGGCTGCGGCGGCAGCGCAATGCCGC
TATGGGGACTTGGGTAGTCTACATGAGGGAGTGTAGCCGGGCCCAGCACTGGATCGCCC
CCAGCCACCACCTCTTCTTCCTGGCATACTCTCTTCACAGCTGAAGAAGGCCAATTATAT
GGGCCAGGAGGCGGGGGCGGCAGCAGCAGCCCAAGCGATGCCGGGCCTGTAGCCCCCTAT
GGCTACACTCGGCCCCCTCAGGGGCTGACAAGCCAGGAGAGTGACTACTCTGCCTCCGAA
GTGTGGTATCCTGGTGGAGTTGTGAACAGAGTACCCTATCCCAGTCCCAATTGTGTCAAA
AGTGAAATGGGACCTTGGATGGAGAACTACTCCGGACCTTATGGGGACATGCG

The 19 CAG repeat is <u>underlined</u>

SEQUENCE LISTING

<160> NUMBER OF SEQ ID NOS: 14

<210> SEQ ID NO 1
<211> LENGTH: 26
<212> TYPE: DNA
<213> ORGANISM: Artificial Sequence
<220> FEATURE:
<223> OTHER INFORMATION: Synthetic Construct

<400> SEQUENCE: 1
acgaggccgg caccatgcaa cttctc                                26

<210> SEQ ID NO 2
<211> LENGTH: 22
<212> TYPE: DNA
<213> ORGANISM: Artificial Sequence
<220> FEATURE:
<223> OTHER INFORMATION: Synthetic Construct

<400> SEQUENCE: 2
cttcgtccag gggaagacct tt                                    22

<210> SEQ ID NO 3
<211> LENGTH: 26
<212> TYPE: DNA
<213> ORGANISM: Artificial Sequence
<220> FEATURE:
<223> OTHER INFORMATION: Synthetic Construct

<400> SEQUENCE: 3
agcatttagg tgacactata gaatag                                26

<210> SEQ ID NO 4
<211> LENGTH: 21
<212> TYPE: DNA
<213> ORGANISM: Artificial Sequence
<220> FEATURE:
<223> OTHER INFORMATION: Synthetic Construct

<400> SEQUENCE: 4
gttccagagc gtgcgcgaag t                                     21

<210> SEQ ID NO 5
<211> LENGTH: 21
<212> TYPE: DNA
<213> ORGANISM: Artificial Sequence
<220> FEATURE:
<223> OTHER INFORMATION: Synthetic Construct

<400> SEQUENCE: 5
tggggcctct acgatgggct t                                     21

<210> SEQ ID NO 6
<211> LENGTH: 47
<212> TYPE: DNA
<213> ORGANISM: Artificial Sequence
<220> FEATURE:
<223> OTHER INFORMATION: Synthetic Construct

<400> SEQUENCE: 6
acgaggccgg caccatgcaa cttctcgagg taatctccga aggcagc          47

<210> SEQ ID NO 7
<211> LENGTH: 22
<212> TYPE: DNA
<213> ORGANISM: Artificial Sequence -continued

```
<220> FEATURE:
<223> OTHER INFORMATION: Synthetic Construct

<400> SEQUENCE: 7
ccaggcttaa gcagctgctc cg                                                22

<210> SEQ ID NO 8
<211> LENGTH: 2320
<212> TYPE: DNA
<213> ORGANISM: Artificial Sequence
<220> FEATURE:
<223> OTHER INFORMATION: Synthetic Construct
<220> FEATURE:
<221> NAME/KEY: exon
<222> LOCATION: (1)..(1550)
<220> FEATURE:
<221> NAME/KEY: Intron
<222> LOCATION: (1551)..(1838)
<220> FEATURE:
<221> NAME/KEY: misc_feature
<222> LOCATION: (1839)..(1881)
<223> OTHER INFORMATION: pCDN3 vector
<220> FEATURE:
<221> NAME/KEY: misc_feature
<222> LOCATION: (1882)..(1995)
<223> OTHER INFORMATION: ploxneo vector sequence
<220> FEATURE:
<221> NAME/KEY: misc_feature
<222> LOCATION: (1996)..(2008)
<223> OTHER INFORMATION: 3'loxp sequence
<220> FEATURE:
<221> NAME/KEY: misc_feature
<222> LOCATION: (2009)..(2018)
<223> OTHER INFORMATION: pCDN3 vector 3' arm
<220> FEATURE:
<221> NAME/KEY: Intron
<222> LOCATION: (2019)..(2320)

<400> SEQUENCE: 8 atg gag gtg cag tta ggg ctg gga agg gtc tac cca cgg ccc cca tcc         48
Met Glu Val Gln Leu Gly Leu Gly Arg Val Tyr Pro Arg Pro Pro Ser
1               5                   10                  15 aag acc tat cga gga gcg ttc cag aat ctg ttc cag agc gtg cgc gaa         96
Lys Thr Tyr Arg Gly Ala Phe Gln Asn Leu Phe Gln Ser Val Arg Glu
            20                  25                  30 gcg atc cag aac ccg ggc ccc agg cac cct gag gcc gct aac ata gca        144
Ala Ile Gln Asn Pro Gly Pro Arg His Pro Glu Ala Ala Asn Ile Ala
        35                  40                  45 cct ccc ggc gcc tgt tta cag cag agg cag gag act agc ccc cgg cgg        192
Pro Pro Gly Ala Cys Leu Gln Gln Arg Gln Glu Thr Ser Pro Arg Arg
    50                  55                  60 cgg cgg cgg cag cag cac act gag gat ggt tct cct caa gcc cac atc        240
Arg Arg Arg Gln Gln His Thr Glu Asp Gly Ser Pro Gln Ala His Ile
65                  70                  75                  80 aga ggc ccc aca ggc tac ctg gcc ctg gag gag gaa cag cag cct tca        288
Arg Gly Pro Thr Gly Tyr Leu Ala Leu Glu Glu Glu Gln Gln Pro Ser
                85                  90                  95 cag cag cag gca gcc tcc gag ggc cac cct gag agc agc tgc ctc ccc        336
Gln Gln Gln Ala Ala Ser Glu Gly His Pro Glu Ser Ser Cys Leu Pro
            100                 105                 110 gag cct ggg gcg gcc acc gct cct ggc aag ggg ctg ccg cag cag cca        384
Glu Pro Gly Ala Ala Thr Ala Pro Gly Lys Gly Leu Pro Gln Gln Pro
        115                 120                 125 cca gct cct cca gat cag gat gac tca gct gcc cca tcc acg ttg tcc        432
Pro Ala Pro Pro Asp Gln Asp Asp Ser Ala Ala Pro Ser Thr Leu Ser
    130                 135                 140 ctg ctg ggc ccc act ttc cca ggc tta agc agc tgc tcc gcc gac att        480
```

-continued

| | | |
|---|---|---|
| Leu Leu Gly Pro Thr Phe Pro Gly Leu Ser Ser Cys Ser Ala Asp Ile<br>145                            150                            155                            160 | | |
| aaa gac att ttg aac gag gcc ggc acc atg caa ctt ctc cag cag cag<br>Lys Asp Ile Leu Asn Glu Ala Gly Thr Met Gln Leu Leu Gln Gln Gln<br>                     165                            170                            175 | | 528 |
| cag cag cag cag cag cag cag cag cag cag cag cag cag cag cag cag<br>Gln Gln Gln Gln Gln Gln Gln Gln Gln Gln Gln Gln Gln Gln Gln Gln<br>                     180                            185                            190 | | 576 |
| gag gta atc tcc gaa ggc agc agc gca aga gcc agg gag gcc acg ggg<br>Glu Val Ile Ser Glu Gly Ser Ser Ala Arg Ala Arg Glu Ala Thr Gly<br>                     195                            200                            205 | | 624 |
| gct ccc tct tcc tcc aag gat agt tac cta ggg ggc aat tca acc ata<br>Ala Pro Ser Ser Ser Lys Asp Ser Tyr Leu Gly Gly Asn Ser Thr Ile<br>210                            215                            220 | | 672 |
| tct gac agt gcc aag gag ttg tgt aaa gca gtg tct gtg tcc atg gga<br>Ser Asp Ser Ala Lys Glu Leu Cys Lys Ala Val Ser Val Ser Met Gly<br>225                            230                            235                            240 | | 720 |
| ttg ggt gtg gaa gca ttg gaa cat ctg agt cca ggg gaa cag ctt cgg<br>Leu Gly Val Glu Ala Leu Glu His Leu Ser Pro Gly Glu Gln Leu Arg<br>                     245                            250                            255 | | 768 |
| gga gac tgc atg tac gcg tcg ctc ctg gga ggt cca ccc gcg gtg cgt<br>Gly Asp Cys Met Tyr Ala Ser Leu Leu Gly Gly Pro Pro Ala Val Arg<br>                     260                            265                            270 | | 816 |
| ccc act cct tgt gcg ccg ctg ccc gaa tgc aaa ggt ctt ccc ctg gac<br>Pro Thr Pro Cys Ala Pro Leu Pro Glu Cys Lys Gly Leu Pro Leu Asp<br>                     275                            280                            285 | | 864 |
| gaa ggc cca ggc aaa agc act gaa gag act gct gag tat tcc tct ttc<br>Glu Gly Pro Gly Lys Ser Thr Glu Glu Thr Ala Glu Tyr Ser Ser Phe<br>290                            295                            300 | | 912 |
| aag gga ggt tac gcc aaa gga ttg gaa ggt gag agc ttg ggg tgc tct<br>Lys Gly Gly Tyr Ala Lys Gly Leu Glu Gly Glu Ser Leu Gly Cys Ser<br>305                            310                            315                            320 | | 960 |
| ggc agc agt gaa gca ggt agc tct ggg aca ctt gag atc ccg tcc tct<br>Gly Ser Ser Glu Ala Gly Ser Ser Gly Thr Leu Glu Ile Pro Ser Ser<br>                     325                            330                            335 | | 1008 |
| ctg tct ctg tat aaa tct gga gca cta gac gag gca gca gca tac cag<br>Leu Ser Leu Tyr Lys Ser Gly Ala Leu Asp Glu Ala Ala Ala Tyr Gln<br>                     340                            345                            350 | | 1056 |
| aat cgc gac tac tac aac ttt ccg ctg gct ctg tcc ggg ccg ccg cac<br>Asn Arg Asp Tyr Tyr Asn Phe Pro Leu Ala Leu Ser Gly Pro Pro His<br>                     355                            360                            365 | | 1104 |
| ccc ccg ccc cct acc cat cca cac gcc cgt atc aag ctg gag aac cca<br>Pro Pro Pro Pro Thr His Pro His Ala Arg Ile Lys Leu Glu Asn Pro<br>370                            375                            380 | | 1152 |
| ttg gac tac ggc agc gcc tgg gct gcg gcg gcg caa tgc cgc tat<br>Leu Asp Tyr Gly Ser Ala Trp Ala Ala Ala Ala Gln Cys Arg Tyr<br>385                            390                            395                            400 | | 1200 |
| ggg gac ttg ggt agt cta cat gga ggg agt gta gcc ggg ccc agc act<br>Gly Asp Leu Gly Ser Leu His Gly Gly Ser Val Ala Gly Pro Ser Thr<br>                     405                            410                            415 | | 1248 |
| gga tcg ccc cca gcc acc acc tct tct tcc tgg cat act ctc ttc aca<br>Gly Ser Pro Pro Ala Thr Thr Ser Ser Ser Trp His Thr Leu Phe Thr<br>                     420                            425                            430 | | 1296 |
| gct gaa gaa ggc caa tta tat ggg cca gga ggc ggg ggc ggc agc agc<br>Ala Glu Glu Gly Gln Leu Tyr Gly Pro Gly Gly Gly Gly Gly Ser Ser<br>                     435                            440                            445 | | 1344 |
| agc cca agc gat gcc ggg cct gta gcc ccc tat ggc tac act cgg ccc<br>Ser Pro Ser Asp Ala Gly Pro Val Ala Pro Tyr Gly Tyr Thr Arg Pro<br>450                            455                            460 | | 1392 |

-continued

| | | |
|---|---|---|
| cct cag ggg ctg aca agc cag gag agt gac tac tct gcc tcc gaa gtg<br>Pro Gln Gly Leu Thr Ser Gln Glu Ser Asp Tyr Ser Ala Ser Glu Val<br>465                 470                 475                 480 | 1440 | |
| tgg tat cct ggt gga gtt gtg aac aga gta ccc tat ccc agt ccc aat<br>Trp Tyr Pro Gly Gly Val Val Asn Arg Val Pro Tyr Pro Ser Pro Asn<br>            485                 490                 495 | 1488 | |
| tgt gtc aaa agt gaa atg gga cct tgg atg gag aac tac tcc gga cct<br>Cys Val Lys Ser Glu Met Gly Pro Trp Met Glu Asn Tyr Ser Gly Pro<br>500                 505                 510 | 1536 | |
| tat ggg gac atg cg gtaagtttat actaaaaatg cctcctttg accaagggca<br>Tyr Gly Asp Met<br>            515 | 1590 | |
| cagagtaagc agtttgcatt ttgtgggatc tagggactcc cgcccaatag aacaatcgga | 1650 | |
| aggatcctaa gtcagctcag actagttcta taggaaggtc tgtcctacat ctggagccct | 1710 | |
| cgtggggact gtcatcttgt gaaatgttcc gcctaagccc agggaatctt tgctgcgctc | 1770 | |
| cggggtgcta atacgtgctc tttgagattc ccctccaatt ccctagcttt tctaaactcc | 1830 | |
| tccattaaga tccactagta acggccgcca gtgtgctgga attctgcaga tgatccccg | 1890 | |
| ggctgcagga attcgatatc aagcttatcg ataccgtcga ggaattccga tcatattcaa | 1950 | |
| taaccccttaa tataacttcg tataatgtat gctatacgaa gttattaggt ccctcgacga | 2010 | |
| gctcggatct ttctgatatt tcaaatccta tgagttccaa acttaaatca attgcatggg | 2070 | |
| ccattttcag aaatgacgcc tgtaagctct tcacggtttt tcattctttt cctcaaagtt | 2130 | |
| ctggaaacac gatcagacat gtagggagtt tcttgtcttt gggtctgttg gtaatcacct | 2190 | |
| tccagacccg tgaagtgaat ggtcttggca taagaaaagg gaaataaaag cagaaacctg | 2250 | |
| attttcggcc cgcatccttc aaagagagat aatagaattc tcaattctcc tagaaagaaa | 2310 | |
| agccgcatct | 2320 | |

<210> SEQ ID NO 9
<211> LENGTH: 1550
<212> TYPE: DNA
<213> ORGANISM: Artificial Sequence
<220> FEATURE:
<223> OTHER INFORMATION: Synthetic Construct

<400> SEQUENCE: 9

| | |
|---|---|
| atggaggtgc agttagggct gggaagggtc tacccacggc ccccatccaa gacctatcga | 60 |
| ggagcgttcc agaatctgtt ccagagcgtg cgcgaagcga tccagaaccc gggccccagg | 120 |
| caccctgagg ccgctaacat agcacctccc ggcgcctgtt tacagcagag gcaggagact | 180 |
| agcccccggc ggcggcggcg gcagcagcac actgaggatg gttctcctca gcccacatc | 240 |
| agaggcccca caggctacct ggccctggag gaggaacagc agccttcaca gcagcaggca | 300 |
| gcctccgagg ccacccctga gcagctgct ctccccgagc ctggggcggc caccgctcct | 360 |
| ggcaagggc tgccgcagca gccaccagct cctccagatc aggatgactc agctgcccca | 420 |
| tccacgttgt ccctgctggg ccccactttc ccaggcttaa gcagctgctc cgccgacatt | 480 |
| aaagacattt tgaacgaggc cggcaccatg caacttcttc agcagcagca gcagcagcag | 540 |
| cagcagcagc agcagcagca gcagcagcag cagcaggagg taatctccga aggcagcagc | 600 |
| gcaagagcca gggaggccac ggggggctccc tcttcctcca aggatagtta cctagggggc | 660 |
| aattcaacca tatctgacag tgccaaggag ttgtgtaaag cagtgtctgt gtccatggga | 720 |
| ttgggtgtga agcattgga acatctgagt ccagggggaac agcttcgggg agactgcatg | 780 |
| tacgcgtcgc tcctgggagg tccacccgcg gtgcgtccca ctccttgtgc gccgctgccc | 840 |

```
gaatgcaaag gtcttcccct ggacgaaggc ccaggcaaaa gcactgaaga gactgctgag    900
tattcctctt tcaagggagg ttacgccaaa ggattggaag gtgagagctt ggggtgctct    960
ggcagcagtg aagcaggtag ctctgggaca cttgagatcc cgtcctctct gtctctgtat   1020
aaatctggag cactagacga ggcagcagca taccagaatc gcgactacta caactttccg   1080
ctggctctgt ccgggccgcc gcacccccg ccccctaccc atccacacgc ccgtatcaag    1140
ctggagaacc cattggacta cggcagcgcc tgggctgcgg cggcagcgca atgccgctat   1200
ggggacttgg gtagtctaca tggagggagt gtagccgggc ccagcactgg atcgccccca   1260
gccaccacct cttcttcctg gcatactctc ttcacagctg aagaaggcca attatatggg   1320
ccaggaggcg ggggcggcag cagcagccca agcgatgccg ggcctgtagc ccctatggc    1380 tacactcggc cccctcaggg gctgacaagc caggagagtg actactctgc ctccgaagtg   1440
tggtatcctg gtggagttgt gaacagagta ccctatccca gtcccaattg tgtcaaaagt   1500
gaaatgggac cttggatgga gaactactcc ggaccttatg gggacatgcg              1550
```

<210> SEQ ID NO 10
<211> LENGTH: 78
<212> TYPE: DNA
<213> ORGANISM: Mus musculus

<400> SEQUENCE: 10

```
catgcaactt cttcagcagc agcaacaaca ggcagcagca ccaacagcag caccaacagc    60
accaacagca gcaggagg                                                  78
```

<210> SEQ ID NO 11
<211> LENGTH: 73
<212> TYPE: DNA
<213> ORGANISM: Artificial Sequence
<220> FEATURE:
<223> OTHER INFORMATION: Synthetic Construct

<400> SEQUENCE: 11

```
atgcaacttc tccagcagca gcagcagcag cagcagcagc agcagcagca gcagcagcag    60
cagcagcagg agg                                                       73
```

<210> SEQ ID NO 12
<211> LENGTH: 54
<212> TYPE: DNA
<213> ORGANISM: Artificial Sequence
<220> FEATURE:
<223> OTHER INFORMATION: Synthetic Construct

<400> SEQUENCE: 12

```
gaacgaggcc ggcaccatgc aacttctcga ggtaatctcc gaaggcagca gcgc          54
```

<210> SEQ ID NO 13
<211> LENGTH: 130
<212> TYPE: DNA
<213> ORGANISM: Artificial Sequence
<220> FEATURE:
<223> OTHER INFORMATION: Synthetic Construct

<400> SEQUENCE: 13

```
tctccagcag cagcagcagc agcagcagca gcagcagcag cagcagcagc agcagcagca    60
gcagcagcag cagcagcagc agcagcagca gcagcagcag cagcagcagc agcagcagca   120
ggaggtaatc                                                          130
```

```
<210> SEQ ID NO 14
<211> LENGTH: 131
<212> TYPE: DNA
<213> ORGANISM: Artificial Sequence
<220> FEATURE:
<223> OTHER INFORMATION: Synthetic Construct

<400> SEQUENCE: 14
tctccaacaa cagcaacaac agcagcagca gcaacagcaa caacagcagc agcaacaaca        60
acagcagcag cagcaacagc agcaacaaca gcagcagcag caacagcagc agcaacaaca       120
gcaggaggta a                                                            131
```

POLY-GLUTAMINE ANDROGEN RECEPTOR KNOCK-IN MOUSE MODELS, REAGENTS AND METHODS

This is a U.S. application, which claims the benefit of 35 U.S.C. 119 based on the priority of Provisional Patent Application No. 62/479,754 filed Mar. 31, 2017, herein incorporated by reference in its entirety.

INCORPORATION OF SEQUENCE LISTING

A computer readable form of the Sequence Listing "SequenceListing_ST25.txt" (14,390 bytes), submitted via EFS-WEB and created on Mar. 28, 2018, is herein incorporated by reference.

FIELD

This disclosure relates to reagents, screening assays and animal models and particularly to mouse models comprising a humanized androgen receptor with a polyglutamine (polyQ) tract as an animal model of various diseases including type 2, diabetes, metabolic syndrome and related liver disorders, prostatic, ovarian, cardiovascular, as well as screening assays employing said animal models and reagents related thereto.

BACKGROUND

The Androgen Receptor Protein and its Polyglutamine Tract

The X-linked androgen receptor (AR) protein is a member of the nuclear receptor superfamily. It is a ligand-inducible transcription factor containing a polymorphic N-terminal region, a central DNA-binding domain (DBD) and a C-terminal ligand-binding domain (LBD). The AR DBD contains two zinc fingers, each anchored by four cysteines, and two α-helical segments. The AR DBD binds to a bipartite androgen response element (ARE) and contributes to the dimerization that underlies co-operative interaction between a pair of AR monomers and the ARE. The AR LBD has the typical nuclear receptor LBD structure of 12 α-helices and small β-sheets in a 3-layer "sandwich"[1-3]. In response to ligand binding, the LBD undergoes conformational changes, completing the assembly of an AF-2 domain and initiating coactivator recruitment.

The structurally flexible N-terminal domain (NTD), harbours a long polymorphic polyglutamine (polyQ) tract (n=11-33). Encoded by a genomic CAG repeat, it helps modulate AR transcriptional activity; ARs with shorter polyQ tracts are the most transcriptionally active.

Trinucleotide repeats are genomically very unstable, i.e., they can expand or contract in length in somatic cells. This exceeds, by many orders of magnitude, the comparative genetic stability of common nucleotide sequences. Using laser microdissection significant somatic AR CAG repeat instability in prostate and breast pathology including short AR CAG repeat lengths has been reported, including polyGln tract deletions.

An attempt to humanize the AR in mouse has been done previously; a knock-in mouse model was created by replacing all of mouse exon one with human exon one (with a 21Q tract) but had no phenotype[1]. Vectors for production of transgenic mouse models to investigate the role of the androgen receptor and its CAG repeat in human prostate cancer are described in Mousavi G[2].

The Androgen Receptor and Intermediary Metabolism

The AR mechanism of action has classically been studied in target organs of the reproductive system. In prostate tissue the AR has very important effects on growth and maintenance of the organ by supporting intracellular growth pathways but are tied to enhancing the basic metabolic machinery in the cell. Thus, androgens support glucose metabolism and do this with the direct involvement of mTOR. The effects of AR on intermediary metabolism are well documented within the liver, again supporting both glucose metabolism and protein metabolism.

Metabolic Syndrome and Related Liver Disorders

Insulin resistance in target tissues, combined with a relative deficiency of insulin secretion are the major features found in both overt T2D and the associated metabolic syndrome (obesity, diabetes, hyperlipidemia, hypertension). Under physiological conditions, when insulin sensitivity decreases, insulin secretion increases to maintain normal glucose levels; when insulin secretion fails to compensate, (β-cell dysfunction/islet failure) abnormal glucose tolerance develops with further progression to overt T2D. Nonalcoholic fatty liver disease (NAFLD) caused by excessive uptake of lipids by the liver has now become a major complication of diabetes. In 30% of patients, chronic inflammation and fibrosis referred to as nonalcoholic steatohepatitis (NASH) ensues with a high risk of hepatocellular carcinoma (HCC). NASH cirrhosis is becoming one of the most common pathological conditions requiring liver transplantations. This progressive hepatic disease often accompanies obesity and has a complex set of causes that include aforementioned insulin resistance, as well as signaling effects from adipose tissue, pancreatic islets, and skeletal muscle. NASH, NASH/cirrhosis and NASH/HCC is rapidly becoming an important health care concern with extensive morbidity and mortality and at the moment there is no assigned therapeutics.

Hepatic steatosis exemplified by nonalcoholic fatty liver disease (NAFLD) is the accumulation of fat in the liver that occurs up to 25% of individuals. NAFLD is identified as a serious risk factor for (30%) nonalcoholic steatohepatitis (NASH) an inflammatory hepatitis that can ultimately culminate in liver failure and cirrhosis. NAFLD is the most common liver disorder in developed countries. NAFLD and NASH are significant risk factors for hepatocellular carcinoma. In developed countries NASH cirrhosis is poised to be the most common disease accounting for liver transplantation.

In Type 2 Diabetes mellitus (T2D), the incidence of NAFLD is even more pronounced as the majority of diabetics (70%) have hepatic steatosis. Also, in T2D NASH, NASH cirrhosis and NASH liver failure is even more aggressive. Currently close to 4 million have diabetes and another 5 million have prediabetes in Canada. It is estimated that as much as 5% will develop liver failure.

Over time clinicians and researchers have made substantial improvements in addressing other serious diseases associated with diabetes (hypertension cardiovascular diseases, diabetic kidney diseases) by introducing new therapeutics. For instance, better hypertension medications with better control of hypertension, the use of powerful lipid lowering agents, and medications that help prevent kidney failure all have had a substantial beneficial effect on controlling complications. This is not the case for diabetes related liver disorders where there are no designated treatment regimens. Presently, close to 400 Canadians receive a liver transplant a year; at a cost of 50 million dollars for the transplant itself, excluding ancillary costs of medications nor costs associated with significant morbidities in individuals with ongoing liver disease. The costs to be incurred in all type II diabetes related liver disorders will become the largest expense overall of diabetic complications.

NAFLD and its progression to NASH with respect to other liver disorders is relatively newly recognized disorder and its morbidity and mortality effects are now being appreciated. For significant and effective therapies to be developed a better understanding of the pathophysiology is needed. To be successful animal models are critical not just for investigative studies but also to test new therapeutics in a convincing manner. Animal mouse models do exist but are far from representing the human condition; as they rely on genetic alterations (mostly through the leptin pathway, which patients do not have) or exaggerated diets are applied.

SUMMARY

An aspect is a construct comprising a) a nucleotide sequence comprising a 5' AR arm comprising a portion of exon 1 of mouse androgen receptor (AR), and b) an exogenous polyglutamime (polyQ) tract encoding sequence inserted into, and/or replacing the endogenous polyQ/H tract encoding sequence, and c) optionally a selectable marker Another aspect of the disclosure includes a recombinant cell or knock-in mouse comprising a recombinant androgen receptor (AR) cassette containing an exogenous polyglutamine (polyQ) tract encoding sequence in exon 1, wherein the polyQ tract encoding sequence is stably integrated into the genome of the cell.

Other aspects include animal disease models, methods of making said animal disease model and screening assays as using said animal models.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

An embodiment of the present disclosure will now be described in relation to the drawings in which:

FIGS. 1A, 1B, 1C and 1D show the Construction of the AR-19Q mouse. FIG. 1A is a schematic representation of the human AR. The NTD harbors a polymorphic nucleotide repeat (CAG) (PolyQ) which regulates the transcriptional activity of the AR. FIG. 1B is a schematic showing the AR CAG (19Q) knock-in targeting vector. Fragments of the mouse AR gene (5' arm, 5' UTR and exon 1; 3' arm, start of intron 1); were used to create the pPGKneoNTRtkpA-plox 3'/5' AR targeting vector. FIG. 1C is a blot showing genotyping of genomic DNA from AR-19Q knock-in mice. Males positives for the AR-19Q allele were bred to heterozygous females to generate the AR-19Q males, AR males, and homozygous AR-19Q female mice. Positive AR-19Q males were inbred to homozygous AR-19Q females to establish a stable lineage. The CAG tract was amplified by PCR using a set of primers flanking the CAG tract to give a PCR product of 256 bp, and positive clones selected by BpmI restriction digests (204 bp+52 bp). FIG. 1D is a schematic showing sequencing of the CAG tract of the AR-19Q knock-in mouse. The CAG repeat tract was amplified from genomic DNA. PCR products of interest were excised and sequenced. The sample from C57BL/6 mouse shows the presence of a mixed glutamine/histidine (CAG/CAA/CAC) tract (SEQ ID NO: 10). The sample from a hemizygous AR-19Q male shows the presence of a homogeneous CAG tract (SEQ ID NO: 11).

FIG. 2A shows sequence for 0 CAG (SEQ ID NO: 12), FIG. 2B shows sequence for 39 CAG (SEQ ID NO: 13) and FIG. 2C shows sequence for a mixed 40 CAG/CAA tract (SEQ ID NO: 14).

FIG. 4A is an image showing the obese phenotype of the AR-19Q knock-in mouse. The picture depicts a 16 month old AR-19Q mouse compared with a 16 month C57BL/6 (wild type) mouse. FIG. 4B is a graph showing body mass difference between the C57BL/6 mouse and the AR-19Q mouse. Mice were kept and fed with standard chow (18% protein rodent diet with 6% fat) and water ad libitum. Body mass started to increase in the AR-19Q mouse early and by six months was quite significant. FIG. 4C is a graph showing fat analysis of AR-19Q mice. White and brown adipose tissue (WAT and BAT, respectively) weight was analyzed between C57BL/6 vs. AR-19Q mice, and found that AR-19Q mice had significantly ($p<0.005$, $p<-/05$) more of all types of white adipose tissue (inguinal, visceral, and subcutaneous). FIG. 4D is a graph of Intraperitoneal Glucose Tolerance Test (IPGTT) of C57BL/6 and AR-19Q mice: Mice were fasting for 4 hour prior to the test. C57BL/6 and AR-19Q were injected intraperitoneally with a 20% glucose solution (2 g/kg body mass). Blood glucose was measured by pricking the saphenous vein and using an Accu-Check® Glucometer (Roche). Samples were taken at t=0 (baseline glucose level), and then post injection at t=20, t=40 and t=60 minutes. FIG. 4E is a graph showing a blood Glucose determination of C57BL/6 and AR-19Q mice: C57BL/6 mice and AR-19Q mice at an age 18 months are kept fasting for two hours and then blood samples are taken using an Accu-Check® Glucometer. FIG. 4F is a graph showing systolic Blood Pressure (SBP) of C57BL/6 and AR-19Q mice. SBP was determined by the Tail Cuff method using the MC 4000 Blood Pressure System (Hatteras). C57BL/6 (n=2) and AR-19Q (n=3) at an age 18 months were allowed to acclimatize to the system for 3 days after which the readings for the 4th and 5th day were recorded for analysis. FIG. 1G is a graph showing food intake between AR-19Q vs. wild-type counterparts, shows no difference. Therefore, AR-19Q mice cannot be considered a hyperphagic model for the phenotypes that are observed.

FIG. 6A images a-c show control prostate from C57BL/6J fed 3 months with high fat diet (HFD). Prostate presents a normal epithelial morphology. Images d through f prostate from AR-19Q fed 3 months with HFD. Epithelial invasion into the stroma is observed (d and f, fat arrow heads). Prostatic hyperplasia is observed as well as low grade mPIN (image e). Images g-i are prostate from AR-19Q fed 6 months with HFD. Prostatic hyperplasia is observed, mPIN and fat infiltration into the lumen of the glands (narrow arrows). Epithelial invasion into the stroma is also observed (fat arrows). FIG. 6B is a series of images from a 16 month old AR-19Q mouse on standard fat diet (SFD) diet (two magnifications). Shows significant epithelial invasion (fat arrowheads). FIG. 6C is Higher magnification immunostaining of prostates from AR-19Q and WT mice on SFD, for Ki67-proliferation marker, AR, and cFMS-inflammation marker.

FIGS. 7A, 7B, 7C and 7D are graphs of Qiagen $RT^2$ mouse gene expression array platform. Each array is designed to analyze the expression of 84 genes commonly involved in either prostate cancer development or each of the metabolic pathways selected. Besides containing specific genes to study, each array contains 5 housekeeping genes, 1 genomic DNA control, 3 reverse-transcription controls, and 3 positive PCR controls. Triplicate total RNA samples for all arrays were prepared and analyzed. Genes that showed a >+/−1.5 fold change in AR-19Q vs. WT mice are included in the figure. FIG. 7A shows results forArray profiling of >18 month AR-19Q vs. WT mouse prostate, performed on arrays specially for Glucose metabolism, AMP-activated protein kinase (AMPK) Signaling, and Mitochondrial Energy Metabolism. In addition to the genes mentioned previously, most notable changes include genes involved in cycle regulation (CCNA1, CDKN1A, CDKN2A, RB1), Fatty acid and Glucose metabolism (ACACB, PFKFB3, ENO1, ENO2), and * indicate components of the electron transport chain and oxidative phosphorylation complexes; ATP6v0D2, a proton pump and marker for lysosomal biogenesis shows the highest expression. FIG. 7B shows results for 6, 12, and >18 month AR-19Q mouse prostate vs. WT time course on a prostate specific array. FIGS. 7C and 7D show another array assessing 84 Inflammatory genes. Of the 84 genes, 80% of chemokines/cytokines (27 genes), 60% of interleukins (8 genes), and 50% of the associated receptors (15 genes) are changed in their expression in AR-19Q vs. WT prostate samples.

FIG. 8A is a graph showing alanine amino transferase (ALT) measurement in AR-19Q vs. C57BL/6 (wild-type) mice. A Biochemical Profile was done using a Comprehensive Profile from Abaxis. C57BL/6 mice and AR-19Q mice at an age 18 months were used. Data indicate that AR-19Q mice present with abnormally high values for ALT indicative of hepatic damage. FIG. 8B are images of H/E stainings of representative livers from C57BL/6 (wild-type) vs. AR-19Q mice, at 6, 12, and 24 months. It is strikingly clear of the fatty liver phenotype of the AR-19Q as it ages, towards the development of NASH. The fatty liver NAFLD and NASH progression phenotype is observed in 100% of the mice.

FIG. 9A are images of Liver Histopathology of C57BL/6 vs. AR-19Q mice. B-NASH, steatosis; AR-19Q sample shows macrovesicular steatosis, confirming the hepatic damage. FIG. 9B are images showing inflammation staining, confirmed from the infiltration of leukocytes. FIG. 9C are images showing fibrosis staining. AR-19Q sample stained with Masson's trichrome stain presents with a high density of collagen fibers indicative of advanced liver damage. FIG. 9D are images showing Hepatocellular carcinoma (HCC) staining. Positive, immunostaining with HepParl antibody for HCC in AR-19Q, illustrated by the strong, punctate staining, is indicative of HCC.

FIGS. 11A, 11B, 11C, 110, 11E and 11F show Assessment of AR-19Q mice under high fat diet. AR-19Q mice were placed on standard fat diet (SFD) or high fat diet (HFD) for a 3 month period. FIG. 11A is an image showing HFD mice gained a considerable amount of weight in that period. FIG. 11B are images showing livers also looked lighter an indication of higher fat content. FIGS. 11C and 11D are graphs showing HFD AR-19Q mice also had higher blood glucose and ALT levels respectively than SFD fed AR-19Q mice. FIG. 11E is a series of images showing comparison of accelerated liver disease of AR-19Q mice on 3 months or 6 months HFD. FIG. 11F is a series of images showing liver histopathology in female AR-19Q mice fed HFD for 6 months. Microvesicles are observed indicating steatosis, some ballooning and periportal fibrosis.

FIG. 13 shows vector sequence containing the exon 1/19Q plus junction/intron 1 in AR-19Q mice.

FIG. 14 shows sequence of exon 1 region of mouse AR knocked-in with a 19Q tract.

DETAILED DESCRIPTION OF THE DISCLOSURE

Figure 2A:
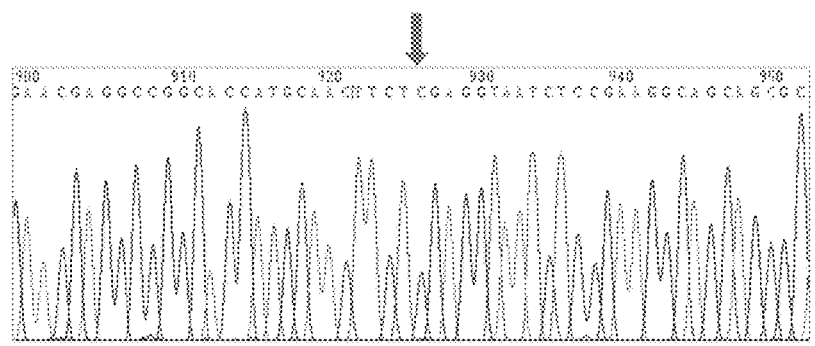
FIGS. 2A, 2B and 2C show sequencing of pPGKneoN-TRtkpA-plox 3'/5'AR plasmids. Confirmation of the generation of targeting vector containing different CAG or CAG/CAA tract lengths.
Figure 2B:
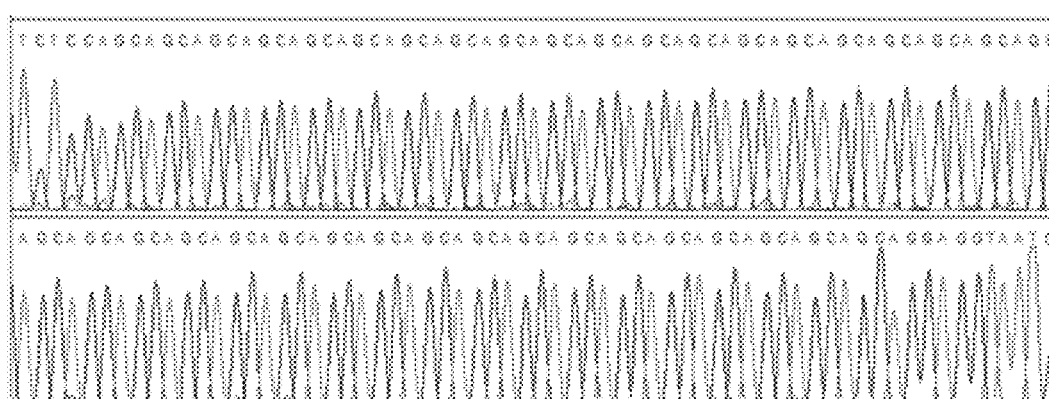
Figure 2C:
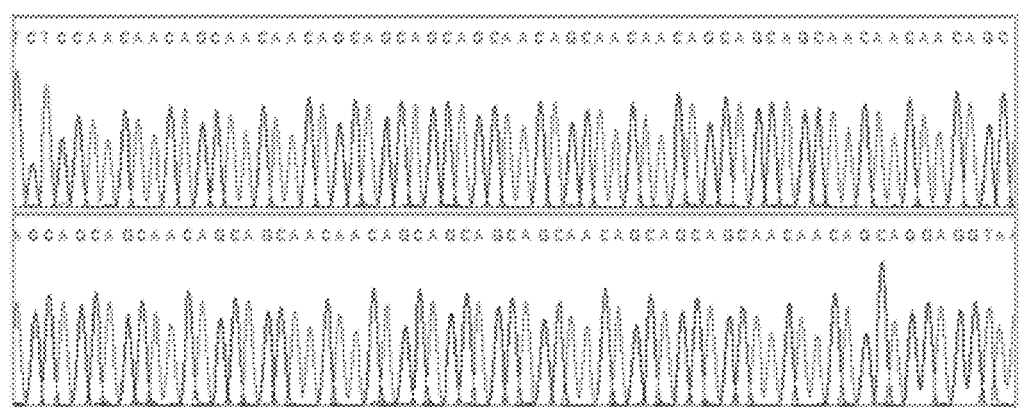

In the following passages, different aspects of the disclosure are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

I. Definitions

The term "knock-in mammal" as used herein means a non-human mammal, for example a mouse, having an exogenous nucleotide sequence, for example a polyQ tract encoding sequence, stably integrated in its genome. In the context of a polyQ knock-in non-human mammal, the non-human mammal can be any mammal lacking a pure endogenous polyQ tract encoding sequence in its AR gene that is amenable to gene knock-in technologies.

The term "androgen receptor" or "AR" (also known as NR3C4) as used herein refers to an AR polypeptide or nucleic acid encoding an AR, from any species and including naturally occurring variants. In humans and in mice the AR gene, is located at the long arm of X-chromosome and is composed of 8 exons. In humans, the AR comprises in exon 1 of its N-terminal domain a nucleotide sequence encoding a polyQ tract. The mouse AR shares over 90% homology with the human ortholog, but lacks the polyQ tract; instead the mouse possess a mixed CAG/CAA/CAC-glutamine/histidine tract in the N-terminal domain of exon 1. The mouse mixed CAG/CAA/CAC tract may comprise 18, 19 or 20 units.

The term "polyglutamine tract" or "polyQ tract" alternatively "polyGln" refers to an amino acid sequence consisting of a plurality of uninterrupted (contiguous) glutamine residues, for example 16, 17, 18, 19, 20, 21, 22 or 23 amino acid residues, or depending on the usage, the nucleotide sequence of repeating CAG or CAA units, optionally only CAG units, encoding said amino acid sequence which is present in exon 1 of the AR gene.

The term "polyQ tract encoding sequence" as used herein means a nucleic acid sequence comprising CAG and/or CAA units, optionally CAG units that encodes a polyQ tract.

The term "sequence identity" as used herein refers to the percentage of sequence identity between two nucleic acid sequences or two polypeptide sequences. To determine the percent identity of two nucleic acid sequences or two amino acid sequences, the sequences are aligned for optimal comparison purposes (e.g., gaps can be introduced in the sequence of a first nucleic acid or amino acid sequence for optimal alignment with a second nucleic acid or amino acid sequence). The nucleotides or amino acid residues at corresponding nucleotide positions or amino acid positions are then compared. When a position in the first sequence is occupied by the same nucleotide or amino acid residue as the corresponding position in the second sequence, then the molecules are identical at that position. The percent identity between the two sequences is a function of the number of identical positions shared by the sequences (i.e., % identity=number of identical overlapping positions/total number of positions times 100%). In one embodiment, the two sequences are the same length. The determination of percent identity between two sequences can also be accomplished using a mathematical algorithm. A preferred, non-limiting example of a mathematical algorithm utilized for the comparison of two sequences is the algorithm of Karlin and Altschul (1990), modified as in Karlin and Altschul (1993). Such an algorithm is incorporated into the NBLAST and XBLAST programs of Altschul et al. (1990). BLAST nucleotide searches can be performed with the NBLAST nucleotide program parameters set, e.g., for score=100, wordlength=12 to obtain nucleotide sequences homologous to a nucleic acid molecules of the present disclosure. BLAST protein searches can be performed with the XBLAST program parameters set, e.g., to score=50, wordlength=3 to obtain amino acid sequences homologous to a protein molecule of the present disclosure. To obtain gapped alignments for comparison purposes, Gapped BLAST can be utilized as described in Altschul et al. (1997). Alternatively, PSI-BLAST can be used to perform an iterated search which detects distant relationships between molecules (Altschul et al., 1997). When utilizing BLAST, Gapped BLAST, and PSI-Blast programs, the default parameters of the respective programs (e.g., of XBLAST and NBLAST) can be used (see, e.g., the NCBI website). Another non-limiting example of a mathematical algorithm utilized for the comparison of sequences is the algorithm of Myers and Miller (1988). Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

The term "recombinant AR cassette" as used herein means a nucleic acid encoding a recombinant AR polypeptide comprising an exogenous polyQ tract instead of or partially replacing an endogenous polyQ/H tract, for example the recombinant AR cassette can refer to a recombinant AR gene in a genome or an isolated nucleic acid encoding a recombinant AR polypeptide. When referring to a recombinant gene in a genome (e.g. of a recombinant cell, fertilized egg, tissue or knock-in mouse, the recombinant AR cassette can also be referred to as the polyQ AR knock in gene or humanized gene. Preferably, only the polyQ tract or a part thereof is exogenous although some sequence upstream and downstream of the polyQ/H tract can also be replaced, for example up to 100 nucleotides, up to 50 nucleotides upstream and/or downstream of the polyQ/H encoding tract in exon 1. When referring to the recombinant AR cassette in a genome, the recombinant AR cassette is under the control of its natural promoter and endogenous gene regulation elements. Typically, for example, a recombinant AR cassette in a recombinant cell, fertilized egg, tissue or knock-in mouse comprises mouse AR sequence and a non-mouse polyQ tract encoding sequence such that all encoded histidines of the endogenous polyQ/H tract are replaced with glutamine residues.

The term "polyQ AR knock-in gene", "knock-in gene" (in the context of AR) or "humanized AR gene" as used herein are used interchangeably and mean a recombinant non-human AR gene comprising an exogenous polyQ tract encoding sequence, regardless of the method used to produce the recombinant non-human AR gene. In such recombinant gene, the endogenous polyQ/H is replaced or partially replaced with or otherwise mutated to produce a polyQ tract encoding sequence. The exogenous polyQ tract encoding sequence can replace all or part of the endogenous mixed poly glutamine/histidine tract, or histidine containing portions thereof. The polyQ AR knock-in gene remains under the control for example, of its natural promoter and endogenous gene regulation elements.

The term "recombinant cell" as used herein refers to any cell, particularly a mouse cell, comprising a recombinant AR cassette and/or expressing a recombinant AR polypeptide, including stem cells such as embryonic stem cells and induced pluripotent stem cells, derived for example from fertilized eggs and differentiated cells respectively. The recombinant cell can be but is not limited to a pancreatic cell, a prostate cell, a kidney cell, a hepatic cell, a mammary cell, or an ovarian cell, for example isolated from a polyQ AR knock in mouse.

The term "replaces all of an endogenous polyQ/H tract encoding sequence" in the context of an exogenous polyQ tract encoding sequence means that the entire endogenous polyQ/H tract encoding sequence in exon 1 of the AR gene is replaced by the exogenous polyQ tract encoding sequence such that no endogenous polyQ/H tract encoding sequence forms part of the recombinant AR cassette. For example, in the context of the mouse whose AR comprises 19 mixed Q/H tract, the exogenous polyQ tract encoding sequence includes 16, 17, 18, 19, 20, 21, 22 or 23 CAG/CAA units and replaces the endogenous 19 Q/H tract encoding sequence.

The term "replaces part of an endogenous polyQ/H tract encoding sequence" in the context of an exogenous polyQ tract encoding sequence means that some residues of the endogenous polyQ/H tract encoding sequence form part of the recombinant AR cassette. The part can be for example 11, 12, 13 up to 18 codons. For example, in the context of the mouse whose AR comprises 19 mixed Q/H tract, the exogenous polyQ tract encoding sequence can comprise 16, 17, 18, 19, 20, 21, 22, 23 CAG/CAA units and replace at least 16, at least 17, at least 18 of the endogenous polyQ/H tract encoding sequence. In some embodiment, 1, 2, 3 or up to 8 CAG/CAA/CAC units from the endogenous polyQ/H tract encoding sequence form part of the recombinant AR cassette. In the C57BL/6 mouse, the polyQ/H tract consists of an initial run of 8 Q encoding codons. Accordingly, a person skilled in the art would understand that an exogenous polyQ tract of 11 Q encoding codons could be used to replace the sequence encoding endogenous polyQ/H at 9 to 19 providing an AR recombinant cassette that includes a total of 19 Q encoding codons. In some embodiments, the exogenous polyQ tract encoding sequence and endogenous polyQ/H tract encoding sequence encode a maximum of 19, 20, 21, 22 or 23 amino acids, optionally a maximum of 19, 20, 21, 22 or 23 contiguous Q amino acids.

The term "metabolic syndrome" as used herein refers to a condition characterized by at least three of central obesity, elevated triglycerides, reduced high-density lipoprotein (HDL), hypertension, and hyperglycemia.

The term "metabolic syndrome related liver disorders" as used herein includes non-alcoholic fatty liver disease (NAFLD), chronic liver inflammation, non-alcoholic steatohepatitis (NASH), hepatitis, NASH fibrosis, NASH cirrhosis, hepatomegaly and/or hepatocellular carcinoma (HCC) that are subsequent to developing metabolic syndrome.

The term "normal diet" "standard diet" or "standard chow" as used herein refers to a diet providing sufficient caloric intake for the subject without causing more than about a 5%, or optionally a 10% weight fluctuation. For example, a normal diet for mice could include a mixture of glucose, lipid, and protein composite. An example includes an 18% protein rodent diet with 6% fat and water ad libitum.

The term "high caloric diet" as used herein includes a high fat diet, a high cholesterol diet, a high glucose diet, a high fructose diet, a high carbohydrate diet and/or a high protein diet.

The term "high fat diet" or "HFD" as used herein refers to a diet wherein at least 60%, of the animal's calorie intake is provided by fat (e.g. lard and/or soy bean oil). A high fat diet may be a high cholesterol diet (e.g. where lard is used) or a non-high cholesterol diet.

The term "high cholesterol diet" as used herein refers to a diet wherein at least 2%, optionally, 2 to 4%, of the animal's calorie intake is provided by cholesterol.

The term "high glucose diet" as used herein refers to a diet wherein at least 60%, of the animal's calorie intake is provided by dextrose.

The term "high fructose diet" as used herein refers to a diet wherein at least 60%, at least 45% or at least 50% of the animal's calorie intake is provided by fructose.

The term "high carbohydrate diet" as used herein refers to a diet wherein at least 70% of the animal's calorie intake is provided by carbohydrate (e.g. sucrose).

The term "high protein diet" as used herein refers to a diet wherein at least 40%, at of the animal's calorie intake is provided by protein (e.g. casein).

The term "test compound" means any compound or composition including any small molecule, metabolite, synthetic polymer nanoparticle, aptamer or biologic such as a nucleic acid (e.g. siRNA), peptide, polypeptide including for example an antibody or binding fragment thereof, composite molecule and/or any composition such as an extract, or combination thereof. The test compound may be in a library or a compound selected from a druggable genome database and can be tested for example in or as part of, a preventative or therapeutic regimen.

The term "preventative or therapeutic regimen" includes a dietary intervention, lifestyle intervention, drug intervention including preventative or therapeutic regimens to be tested using a model described here. A regimen as used here can include administrations of multiple doses of a test compound (i.e. repeated drug intervention) or a combination of a drug intervention and other intervention.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of addiction, stabilized (i.e. not worsening) state of addiction, delay or slowing of addiction progression, amelioration, diminishment of the reoccurrence of the addiction, and remission (whether partial or total), whether detectable or undetectable. "Treating" and "Treatment" can also mean prolonging survival as compared to expected survival if not receiving treatment. "Treating" and "treatment" as used herein also include prophylactic treatment.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps.

The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

In understanding the scope of the present disclosure, the term "consisting" and its derivatives, as used herein, are intended to be close ended terms that specify the presence of stated features, elements, components, groups, integers, and/or steps, and also exclude the presence of other unstated features, elements, components, groups, integers and/or steps.

As used in this specification and the appended claims, the singular forms "a", "an" and "the" include plural references unless the content clearly dictates otherwise. Thus, for example, a composition containing "a compound" includes a mixture of two or more compounds. It should also be noted that the term "or" is generally employed in its sense including "and/or" unless the content clearly dictates otherwise.

The definitions and embodiments described in particular sections are intended to be applicable to other embodiments herein described for which they are suitable as would be understood by a person skilled in the art.

The recitation of numerical ranges by endpoints, for example activity levels, blood pressure levels, enzyme levels, and the like herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about." Further, it is to be understood that "a,"

"an," and "the" include plural referents unless the content clearly dictates otherwise. The term "about" means plus or minus 0.1 to 10%, 1-10%, or preferably 1-5%, of the number to which reference is being made.

Further, the definitions and embodiments described in particular sections are intended to be applicable to other embodiments herein described for which they are suitable as would be understood by a person skilled in the art. For example, in the following passages, different aspects of the present disclosure are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

II. Constructs

The present disclosure provides a nucleic acid construct for producing a recombinant mouse that comprises a humanized androgen receptor (AR) gene.

In one embodiment, the construct is a targeting construct for making a recombinant (i.e. knock in) mouse that comprises a humanized AR gene or plasmid construct that includes a portion such as an arm (e.g. a 5' arm or 3' arm) for making the humanized AR targeting construct.

In one embodiment, the construct comprises a vector backbone and a 5' arm comprising all or part of a mouse AR exon1 and an exogenous polyQ tract encoding sequence. In all cases, the 5' arm includes i) mouse AR sequence upstream and downstream of the endogenous mixed poly glutamine/histidine tract encoding sequence and ii) the exogenous polyQ tract encoding sequence. The exogenous polyQ tract encoding sequence replaces all or part of the endogenous mixed poly glutamine/histidine tract.

The vector backbone comprising for example the 5' arm can be any suitable plasmid, for example pUC19 or plasmids described elsewhere. Suitable vector backbones for the targeting vector include for example the pPGKneoN-TRtkpA-plox 3'/5' targeting vector as was used herein.

Referring to Example 1 and FIG. 1B, fragments of the mouse AR gene (5' arm, 5' UTR and exon 1; 3' arm, start of intron 1) were used to create the pPGKneoNTRtkpA-plox 3'/5' AR targeting vector.

Virus vectors for generating recombinant cultured cells can also be used. For example, recombinant adeno-associated viruses (rAAVs) have been adapted for targeting cells. Infectious rAAV stock can be produced comprising the targeting construct and used to prepare heterozygous and homozygous knock-in cells.

As shown in FIG. 1B, the 5' AR arm has a size of 4.6 kb, the 3' AR arm a size of 4.1 kb, and the assembled pPGK-neoNTRtkpA-plox 3'/5' AR targeting vector a size of about 16 kb. Depending on the available sequence other size arms can also be used.

Other constructs and other technologies such as CRISPR can be used to obtain a polyQ knock-in mouse.

For example, a method or construct can be any method or construct capable of inserting a polyQ tract encoding sequence and/or replacing an endogenous polyQ/H tract encoding sequence in an AR gene. As described herein, an AR Q19 knock-in mouse was made. The sequence of exon 1/19Q plus junction/intron 1 after Cre recombinase treatment is shown in FIG. 13 and SEQ ID NO: 8.

In an embodiment, the construct is one that produces a polyQ knock-in having the sequence as shown in SEQ ID NO: 8 or at least 80%, at least 85%, at least 90%, at least 95%, at least 98% or at least 99% sequence identity thereto. For example, the construct specific portions that are non-functional (e.g. pCN3 sequence) can be excluded or varied. The sequence can for example be more similar to SEQ ID NO: 9 which shows exon 1 region knocked-in with a 19Q tract (FIG. 14).

As the construct is for producing a recombinant mouse that comprises a humanized androgen receptor (AR) gene, the length of the polyQ tract encoding sequence can for example encode 16 to 23 glutamine residues and preferably 19 glutamine residues. When referring to the length of the polyQ tract it will be understood that the length can depending on the context. For example, the length may refer to the sequence in the construct which may encode 16 or less glutamine residues or may refer to the length in the transgenic animal which can comprise an exclusively exogenous polyQ tract or combination exogenous and endogenous polyQ tract as long as the tract is composed of glutamine residues only. Hence, the length of the polyQ tract can refer to the length of the exogenous polyQ tract or the polyQ tract that is partially endogenous (for example the mouse polyQ/H tract begins with a string of Q residues) and exogenous, such that all His encoding residues are replaced.

Figure 3:
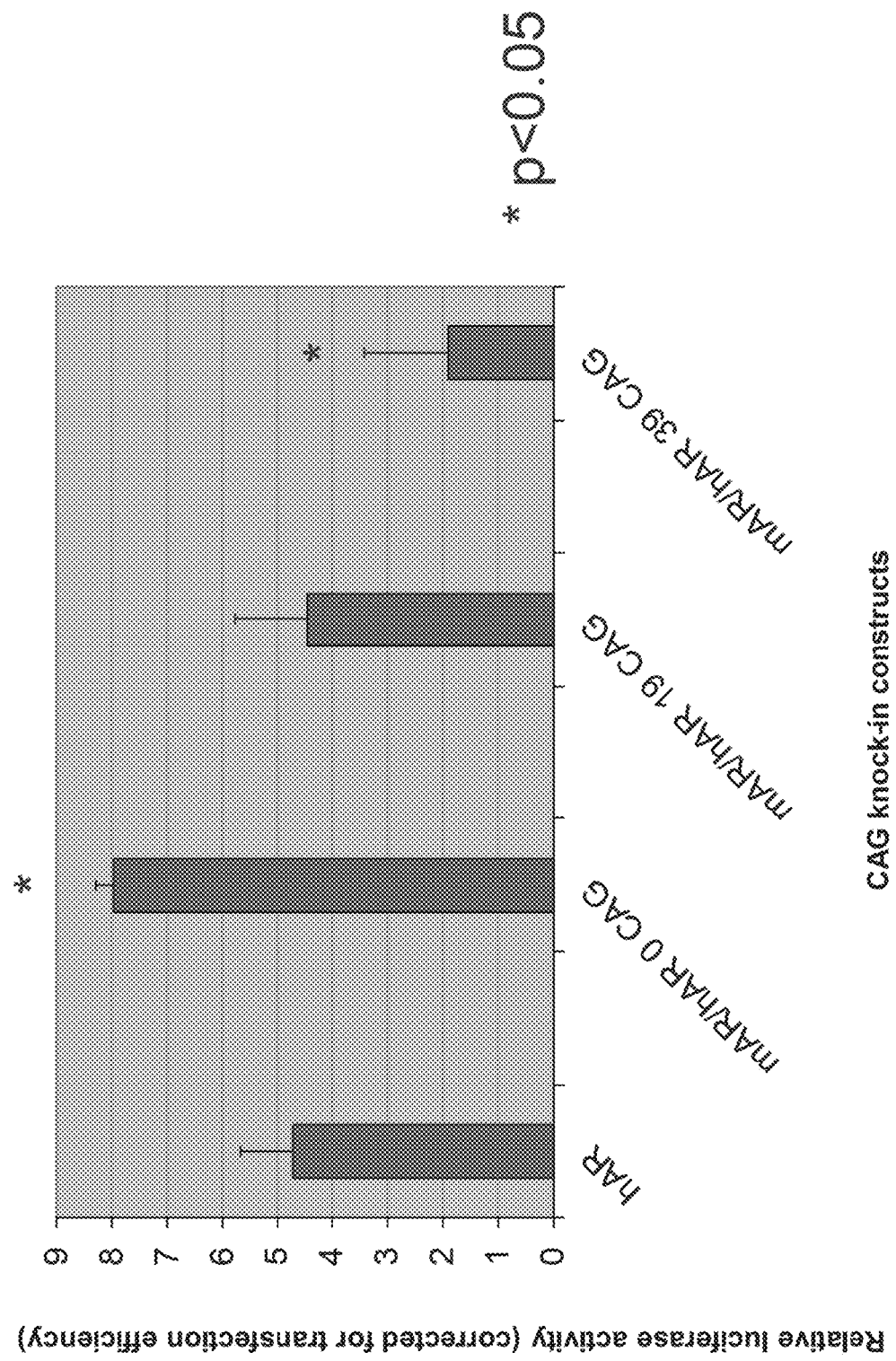
FIG. 3 Is a graphs showing CAG tract length activities. Relative luciferase activity in transfected COS-1 cells comparing transcriptional activity between wildtype AR and AR with various knock-in CAG repeats. * denotes significant p-value ($<0.05$) relative to human AR (hAR).

Referring to FIG. 3, in in vitro transactivation assays, it was shown that an AR construct comprising 19 CAG repeats had similar activity to the human androgen receptor whereas constructs comprising a 0 CAG repeat or 39 CAG repeats had significantly different activity from human AR. The term "similar activity" as used in this context means a no greater than 40%, 30%, 20%, 10% or 5% difference in transactivation properties compared to human AR. Constructs having 16 to 23 CAG units may also show similar activity and would be expected to show a phenotype similar to the phenotype of the AR-19Q knock-in mouse described in the Examples.

In one embodiment, the polyQ tract encoding sequence comprises at least 16 contiguous CAG units. For example, the polyQ tract encoding sequence comprises 16, 17, 18, 19, 20, 21, 22 or 23 contiguous CAG units.

For example, the polyQ tract encoding sequence comprises 16 to 23 contiguous CAG units. For example, the polyQ tract encoding sequence comprises 18 to 21 contiguous CAG units, for example, the polyQ tract encoding sequence comprises 19 CAG units. For example, the polyQ tract encoding sequence consists of 19 CAG units.

In other embodiments, the polyQ tract encoding sequences comprises CAA units.

Referring to Example 1, the polyQ tract encoding sequence comprises 19 contiguous CAG repeats and replaces the endogenous poly glutamine/histidine encoding sequence.

The CAG units of the polyQ tract encoding sequence may fully or partially replace the native endogenous tract sequence. For example, in the context of native mouse AR, which natively comprises in exon 1 a mixed CAG/CAA/CAC-glutamine/histidine tract of 19 units, the polyQ tract encoding sequence may comprise 19 CAG units and fully replace the native endogenous tract sequence. For example, the exogenous polyQ tract encoding sequence can comprise fewer than 19 units, such as 16 CAG units. The 16 CAG units can fully or partially replace the endogenous tract. In an embodiment, it partially replaces the native CAG/CAA/CAC tract of mouse AR (e.g. the polyQ tract comprises 16 CAG units and 3 native units of mouse CAG/CAA/CAC tract remain).

If desired, the construct can be engineered to comprise selectable markers such as reporter genes. As used herein, a "selectable marker" refers to a genetic element that provides a selectable phenotype to a cell in which the selectable marker has been introduced. A selectable marker is generally a gene whose gene product provides resistance to an agent that inhibits cell growth or kills a cell. A variety of selectable markers can be used in the DNA constructs of the disclosure, including, for example, Neo, Hyg, hisD, Gpt, hsv-tk and Ble genes, as described, for example in Ausubel et al.[3] and U.S. Pat. No. 5,981,830. Drugs useful for selecting for the presence of a selectable marker include, for example, G418 for Neo, hygromycin for Hyg, histidinol for hisD, xanthine for Gpt, and bleomycin for Ble (see Ausubel et al, supra, (1999); U.S. Pat. No. 5,981,830). DNA constructs can incorporate a positive selectable marker, a negative selectable marker, or both (see, for example, U.S. Pat. No. 5,981,830).

For example, as shown in Example 1, the neomycin resistance (neo) and herpes simplex virus-thymidine kinase (hsv-tk) selectable genes are included in the construct.

The constructs can be used for generating knock-in cells or knock-in mouse models.

Also provided are reagents for making and/or confirming that the construct is stably integrated into genome of the knock-in mouse.

As described in Example 1, specific primers flanking the CAG tract encoding sequence were used to amplify the CAG tract encoding sequence by PCR and to give a PCR product of 256 bp.

An aspect provided herein is a primer having the following nucleic acid sequence: FWD:

(SEQ ID NO: 4)
5'-GTTCCAGAGCGTGCGCGAAGT-3'.

Another aspect provided herein is a primer having the following nucleic acid sequence:

REV:
(SEQ ID NO: 5)
5'-TGGGGCCTCTACGATGGGCTT-3'.

A further aspect includes an isolated nucleic acid sequence amplified using SEQ ID NO: 4 and 5, or a portion of any of the foregoing. In an embodiment, the isolated nucleic acid comprises all or part of SEQ ID NO: 8 or a sequence with at least or at least 80%, at least 85%, at least 90%, at least 95%, at least 98% or at least 99% sequence identity thereto.

III. Cells, Fertilized Eggs and Animals

Described herein are transgenic mice, fertilized eggs and recombinant cells comprising a humanized AR gene. The transgenic mice, fertilized eggs and recombinant cells comprising endogenous AR sequence with an exogenous polyQ tract encoding sequence and uses thereof. Said transgenic mice, fertilized eggs and recombinant cells can be made using for example targeting constructs and methods described herein. As shown herein, these transgenic mice and recombinant cells are useful as disease models for several diseases as described herein.

As described herein, the humanized AR gene comprises an endogenous mouse AR sequence with the exogenous polyQ tract encoding sequence replacing or partially replacing the endogenous mouse polyQ/H tract encoding sequence, wherein all histidine residues in said polyQ/H are replaced with glutamine residues.

Accordingly, one aspect is a knock in mouse comprising a recombinant androgen receptor (AR) cassette, the recombinant AR cassette comprising an exogenous polyQ tract encoding sequence in exon 1 of an endogenous AR sequence, wherein the polyQ tract encoding sequence is stably integrated into the genome of the knock-in mouse.

A method of making the humanized AR mouse is described herein. A person skilled in the art would recognize other methods such as CRISPR could also be used to convert the mouse sequence encoding the polyQ/H tract in exon 1 to a polyQ tract.

A construct comprising a sequence encoding a polyQ tract can be integrated into the genome of a mouse or used to convert the sequence encoding the polyQ/H tract to one encoding a polyQ tract, by any method known to those skilled in the art. The construct be introduced into pluripotent cells, such as ES cells, by any suitable method that will permit replacing DNA in animal cells. Techniques that can be used include, but are not limited to, CRISPR technology, calcium phosphate/DNA co-precipitates, microinjection of DNA into the nucleus, electroporation, bacterial protoplast fusion with intact cells, transfection, and polycations, (e.g., polybrene, polyornithine, etc.). The DNA can be single or double stranded DNA, linear or circular. (See for example, Hogan et al.[4], Hogan et al.[5] U.S. Pat. Nos. 5,602,299; 5,175,384; 6,066,778; 4,873,191 and 6,037,521; retrovirus mediated gene transfer into germ lines (Van der Putten et al. (1985)) Proc. Natl. Acad. Sci. U.S.A. 82, 6148-6152; gene targeting in embryonic stem cells (Thompson et al. (1989) Cell 56, 313-321); electroporation of embryos (Lo (1983) Mol. Cell. Biol. 3, 1803-1814); and sperm-mediated gene transfer (Lavitrano et al. (1989) Cell 57, 717-723))

Referring to FIG. 1, mouse embryonic stem (ES) cells were electroporated with a construct (knock-in vector). ES cells identified as having homologous recombination of the polyQ AR knock-in gene were selected and then injected into mouse blastocysts which were implanted into female mice. Back-crossing of chimeras was carried out until pure homozygous AR-19Q knock-in mice were obtained (FIG. 1C/D).

It will be understood that embryonal cells at various developmental stages can also be used to introduce genes for the production of knock-in mice. Also, different methods are used depending on the stage of development of the embryonal cell. For example, ES cells can be incorporated into a developing embryo through injection into the blastocyst cavity of a murine blastocyst-stage embryo, by injection into a morula-stage embryo, by co-culture of ES cells with a morula-stage embryo, or through fusion of the ES cell with an enucleated zygote. The resulting embryo is raised to sexual maturity and bred in order to obtain animals, whose cells (including germ cells) carry the polyQ AR knock-in gene. If the original ES cell was heterozygous for the insertion, several of these animals can be bred with each other in order to generate animals homozygous for the insertion. Upon making the knock-in mice having a polyQ AR knock-in gene, the animals may be screened using, for example, Southern blot analysis, Northern blot analysis, Western blot analysis or PCR techniques, to analyze animal tissues to verify the polyQ AR knock-in gene was been stably integrated in the genome of the animal. As shown herein, a construct for making the humanized AR was introduced into ES cells for implantation and creation of a chimeric mouse clone that was then bred to C57BL/6 strain mice making a C57BL/6-chimeric mouse. This mouse can be inter-bred to get a desired purity of the humanized AR gene, for example 5×, 7× or 10× or more to obtain a desired genetic purity.

An aspect provided herein is a recombinant cell. The recombinant cell can be a primary cell or a cell line, optionally a cell line produced from a primary cell such as a primary cell isolated from a recombinant mouse. The recombinant cell comprises a recombinant androgen receptor (AR) cassette, the recombinant AR cassette containing an exogenous polyglutamine (polyQ) tract encoding sequence in exon 1, wherein the polyQ tract encoding sequence is stably integrated into the genome of the cell. The recombinant cell may for example be made or isolate from a knock in mouse. The polyQ tract encoding sequence encodes a poly Q tract of at least 16 amino acids.

In an embodiment is provided a recombinant cell expressing a recombinant AR polypeptide, the recombinant AR polypeptide comprising an exogenous polyQ tract, wherein the exogenous polyQ tract replaces all or part of an endogenous AR polyQ/H tract.

The recombinant cell can for example be made using cell knock in technologies that result in converting the polyQ/H tract to a polyQ tract.

The recombinant cell is typically a mouse cell. Mouse cells comprise an AR with a mixed polyQ/H tract. Other species that have a mixed polyQ/H tract can also be used.

For example, the recombinant cell can be a pancreatic cell, a kidney cell, a hepatic cell, a mammary cell or an ovarian cell.

The recombinant cell can be a stem cell, for example an embryonic stem cell derived from a recombinant fertilized egg, or optionally an induced pluripotent stem cell derived from a polyQ AR knock in mouse.

For example, the recombinant cell can be an induced pluripotent stem cell, and be differentiated through a developmental program to generate, a pancreatic cell, a kidney cell, a hepatic cell, a mammary cell, an ovarian cell, or prostate cell, In an embodiment, the recombinant cell is made using a targeting construct, for example a recombinant adeno-associated virus targeting construct.

In a preferred embodiment, the recombinant cell is isolated from a recombinant mouse comprising the humanized AR gene.

In an embodiment, the recombinant cell is isolated from a recombinant mouse, optionally an AR-19Q knock-in mouse comprising an exogenous polyQ tract of 19 amino acids.

In an embodiment, the recombinant cell is from a knock-in mouse and the polyQ tract encoding sequence fully or partially replaces the native mixed CAG/CAA/CAC-glutamine/histidine tract.

Also provided in another aspect is a recombinant fertilized egg (e.g. mouse fertilized egg) comprising a recombinant AR cassette comprising an exogenous polyQ tract encoding sequence in exon 1 of an endogenous AR sequence, wherein the polyQ tract encoding sequence is stably integrated into the genome of the fertilized egg. The egg can for example be fertilized in vitro or isolated from a pregnant female. The recombinant fertilized eggs can be stored in liquid nitrogen in appropriate freezing media.

Also provided is a recombinant tissue comprising a recombinant AR cassette comprising an exogenous polyQ tract encoding sequence in exon 1 of an endogenous AR sequence, wherein the polyQ tract encoding sequence is stably integrated into the genome of cells of the tissue.

In an embodiment, provided is a polyQ AR knock-in mouse, recombinant cell, tissue or fertilized egg that expresses a recombinant AR polypeptide, the recombinant AR polypeptide comprising an exogenous polyQ tract, wherein the polyQ tract replaces all or part of an endogenous AR polyQ/H tract.

In an embodiment, the polyQ AR knock-in mouse comprises a recombinant androgen receptor (AR) cassette, the recombinant AR cassette containing an exogenous polyQ tract encoding sequence in exon 1, wherein the polyQ tract encoding sequence is stably integrated into the genome of the knock-in mouse and the recombinant AR cassette is expressed in the knock-in mouse.

In an embodiment, the polyQ tract comprises or consists of 16 to 23 glutamine residues.

For example, the polyQ tract comprises or consists of 18 to 21 glutamine residues.

In an embodiment, the polyQ tract comprises or consists of 19 glutamine residues.

It will be understood that any suitable mouse strain which has a mixed tract (e.g. polyQ/H tract) in which an exogenous polyQ tract encoding sequence may be stably integrated into the genome of the mouse may be used (e.g. any strain used for genetic altered mouse models). For example, the mouse can be a C57BL/6 mouse.

In an embodiment, the recombinant mouse, comprises an exogenous polyQ tract that encodes 19 amino acids referred to as an AR-19Q knock-in mouse.

In an embodiment, the polyQ AR knock-in mouse, is homozygous for the recombinant AR cassette, optionally wherein the recombinant AR cassette comprises a 19Q exogenous polyQ tract encoding sequence insert.

In some embodiments such as disease models and screening assays, mammals of a particular sex or age are desired.

It is demonstrated herein, that recombinant males and females for example when fed a high fat diet, exhibit different diseases and symptoms thereof.

As shown in the examples below, male mice for example depending on their age and diet exhibit metabolic disease and related liver abnormalities and obese phenotype, prostate disease, diabetes and cardiovascular disease.

Female mice for example fed a high fat diet exhibit metabolic syndrome and ovarian disease and the ensuing infertility.

Disease symptoms are detectable for example in females fed HFD after 3 months. Male mice also after 3 months of HFD as shown here exhibit detectable disease symptoms.

Accordingly, in one embodiment, the knock in mouse is a male mouse. In another embodiment, the knock in mouse is a female mouse. In some embodiments, the recombinant mouse is a recombinant mouse that has been fed a high fat or high cholesterol diet for at least one month, at least two months or at least three months.

In some embodiments, the polyQ AR knock-in mouse is female fed a high fat/high cholesterol diet or with altered androgen hormone levels, optionally wherein the hormone levels are altered by surgically removing the ovaries or by hormone replacement therapy resulting in for example increased testosterone levels. It is believed that higher estrogen levels in female mice may interfere and inhibit androgen receptor activity and that, for example, removing ovaries from the females or providing excess testosterone may alleviate androgen receptor inhibition.

Interestingly, it was found that mice, including female mice, once developing symptoms for example of metabolic syndrome continue to exhibit symptoms of the disease even when fed a normal diet.

In an embodiment, the polyQ tract encoding sequence fully or partially replaces the native mixed CAG/CAA/CAC-glutamine/histidine tract encoding sequence.

The AR-19Q mice described in the Examples exhibit signs of type 2 diabetes, prostatic disease, ovarian disease and accompanying infertility, a metabolic syndrome phenotype and related liver diseases and cardiovascular abnormalities.

IV. Disease Models and Screening Assays

The polyQ AR knock-in mice described herein comprising a recombinant AR cassette, for example the AR-19Q knock-in mouse described in Example 1, surprisingly exhibit phenotypes associated with several human diseases and based on the exhibited phenotype may be used as disease models, for example as a metabolic syndrome disease model, a type 2 diabetes mellitus (T2D) disease model, a prostate disorder model, a model for liver diseases associated with metabolic syndrome, a cardiovascular disease model, and an ovarian disease with accompanying infertility model. Recombinant animals can for example used in for screening assays to test or identify therapeutic agents, identify biomarkers, assess lifestyle impact and interventions, and for understanding initiation and/or progression of disease for example in different environments. Mice may be fed different diets and/or aged prior to testing and can be selected to have one or more of the features described herein.

As recombinant mice exhibit detectable symptoms at about 2 months of age, they can be used to investigate interventions that delay or reduce onset of disease and/or treat various stages or symptoms of said diseases.

Metabolic syndrome, Type 2 diabetes mellitus, and Hypertension.

An aspect provided herein is a polyQ AR knock-in mouse for use as a metabolic syndrome animal model. Such mammal models can be used for screening for new compounds and interventions, identifying useful biomarkers for disease monitoring and assessing disease progression and outcome. Furthermore, such mouse models can be used in exploring etiologies of disease initiation and/or progression.

As detailed in the Examples, the AR-19Q knock-in mouse exhibits several disease features associated with metabolic syndrome in humans including obesity, elevated triglycerides, high-density lipoprotein (HDL), hypertension, and hyperglycemia.

Figure 4A:
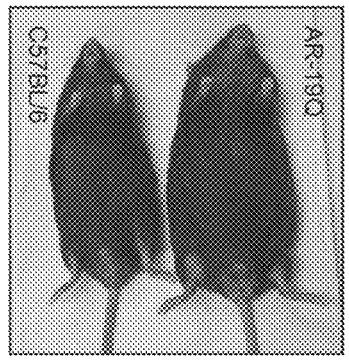
FIGS. 4A, 4B, 4C, 4D, 4E, 4F and 4G show characterization of AR-19Q knock-in mouse.
Figure 4B:
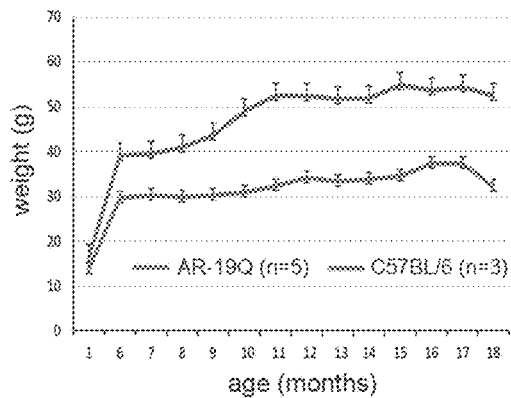
Figure 4C:
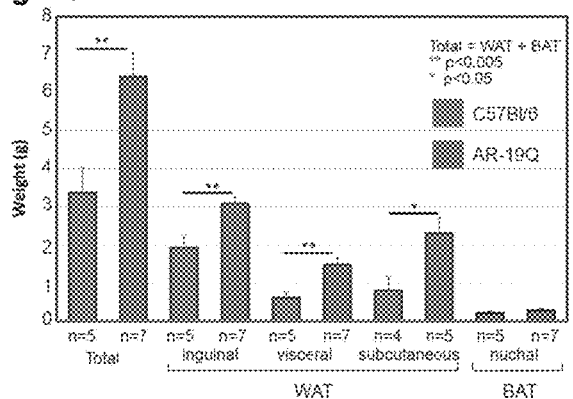

Referring to FIG. 4A to 4C, the AR-19Q mice exhibit weight gain commencing at 3 months, compared to wild-type mice. Both the AR-19Q and wild-type mice were fed the same diet.

Preventive or therapeutic regimens that inhibit or reverse one or more disease features are putative preventive or therapeutic regimen for the prevention or treatment of metabolic syndrome, type 2 diabetes mellitus, and/or hypertension. These can be assessed by measuring one or more relevant readouts depending on the disease or symptom and the regimen.

Referring to the weight gain between AR-19Q mice vs. the wild-type mice, is the AR-19Q does not eat more food than its wild-type counterpart, i.e., the AR-19Q is not a hyperphagic mouse model.

In an embodiment, the polyQ AR knock-in mouse has at least at least 30%, at least 40%, at least 50%, at least 60% or at least 70% greater weight compared to a control age-matched mouse lacking the recombinant AR cassette.

In some embodiments, the method further comprises one or more further controls such as age matched mouse lacking the recombinant AR cassette. By comparing AR-19Q to mice without the recombinant cassette (e.g. optionally treated or untreated), the degree of inhibition can be further assessed, for example by assessing if the regimen prevents a disease symptom or reduces the disease symptom to base line (e.g. return to wild type levels).

Figure 4D:
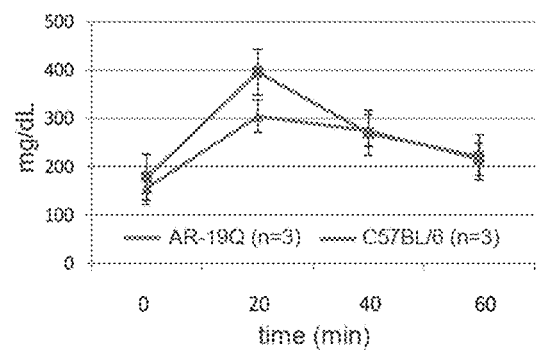
Figure 4E:
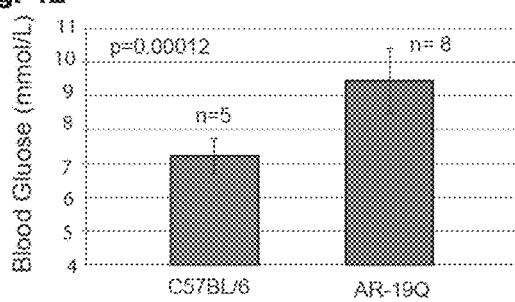
Figure 4F:
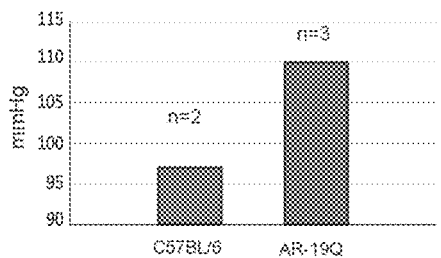
Figure 4G:
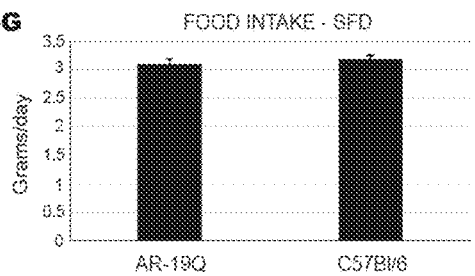

In FIG. 4F, it is shown that the systolic blood pressure of AR-19Q mice is elevated compared to wild-type mice. In an embodiment, the polyQ AR knock-in mouse tested exhibits systolic and/or diastolic hypertension. In an embodiment, the polyQ AR knock-in mouse has a systolic blood pressure of at least 10%, at least 20%, at least 30% or at least 40% greater than the systolic blood pressure of a control age-matched mammal lacking the recombinant AR cassette. In an embodiment, the polyQ AR knock-in mouse has a diastolic blood pressure of at least 10%, at least 20%, at least 30% or at least 40% greater than the systolic blood pressure of a control age-matched mice lacking the recombinant AR cassette. In some embodiments, the relevant disease readout is systolic blood pressure and/or diastolic blood pressure.

Referring now to FIGS. 4D and 4E, it was found that the AR-19Q mice had elevated blood glucose compared to wild-type mice.

In some embodiments, the polyQ AR knock-in mouse tested exhibits hyperglycemia, optionally post-prandial and/or fasting hyperglycemia. In such embodiments, the relevant readout can be measuring hyperglycemia.

Figure 5A:
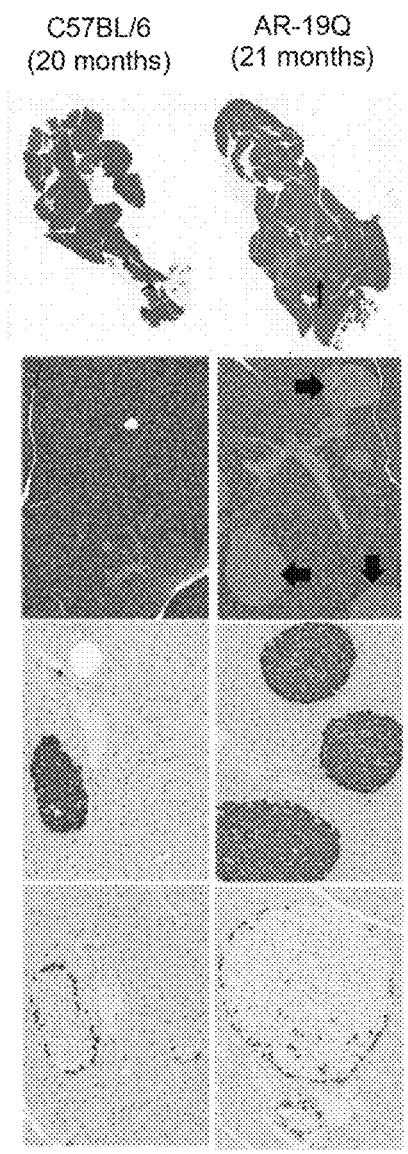
FIGS. 5A and B are images showing islet cell hyperplasia in AR-19Q knock-in mice. FIG. A shows histopathology of the pancreas from a 21 month old AR-19Q and a 20 month old C57BL/6 mice which was conducted using hematoxylin and eosin (H/E) stain. The analysis indicates that the AR-19Q mouse presents significant pancreatic islet hyperplasia as indicated by the arrows. AR-19Q mice also show robust expression of insulin and glucagon (middle and bottom panels respectively).
Figure 5B:
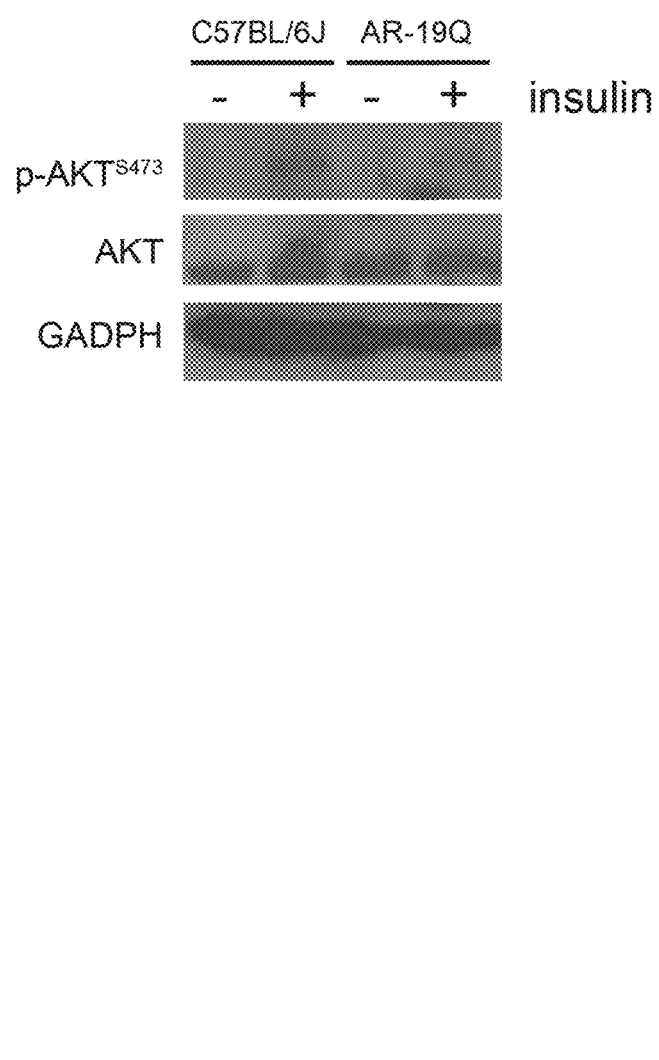
FIG. 5B is a Western blot analysis of insulin injected mice. White adipose tissue lysates of AR-19Q vs. WT counterparts, show a marked reduced p-AKT activity upon insulin stimulation, indicative of insulin resistance.

Referring now to FIG. 5, the AR-19Q knock-in mice presented pancreatic islet hyperplasia as well as a robust expression of insulin and glucagon.

In another aspect of FIG. 5, the islet hyperplasia and increase in insulin, results in the development of insulin resistance, as measured by p-AKT levels in adipose tissue from AR-19Q mice. Lower p-AKT levels indicate insulin resistance. Accordingly in some embodiments, the level of p-AKT is measured to see if a preventive or treatment regimen is improving insulin sensitivity.

In another aspect, the polyQ AR knock-in mouse is used as a type 2 diabetes mellitus (T2D) model.

For example, the mouse displays hyperglycemia, pancreatic hyperplasia, beta islet cell hyperplasia and/or insulin resistance.

For example, the mouse! develops diabetic kidney disease and may eventually develop kidney failure. For example, the mammal displays renal function, optionally as measured by albumin to creatinine ratio in the urine. Accordingly, the recombinant mouse can be used to test preventive or therapeutic regimens for any of the foregoing and assessment of one or more of the disease symptoms can be used as relevant readouts in an assay for assessing preventive or therapeutic regimens including for hyperglycemia, pancreatic hyperplasia, beta islet cell hyperplasia, insulin resistance, diabetic kidney disease and/or renal failure.

In an embodiment, the mammal is a male mammal, optionally a male mouse. In an embodiment, the mouse is a female mouse, optionally fed a high caloric diet such as a HFD or a HCD.

Referring now to FIG. 11, it was shown that placing the AR-19Q mice on a high fat diet may accelerate the appearance of the metabolic syndrome and T2D phenotype. It was shown that AR-19Q mice on a high fat diet (HFD) gained more weight (e.g. at least 20%, at least 30%, at least 40% or at least 50% more weight) compared to AR-19Q mice on a standard fat diet (SFD). The HFD fed mice also presented fatty liver, higher blood glucose and increased ALT levels. Female mice fed a HFD also exhibited appearance of the metabolic syndrome and T2D phenotype compared to wild type females and females fed a standard diet.

In further embodiments, the AR-19Q mice may be fed on special diets, for example high caloric diets, such as high fat diets (HFD) or high cholesterol diets (HCD), to accelerate the appearance of disease phenotypes. For example, the AR-19Q mouse fed on a HFD may develop hepatocellular carcinoma (HCC) more rapidly.

For example, the polyQ AR knock-in mouse is fed on I) a high glucose diet, II) a high fat diet, III) a high fructose diet, IV) a high carbohydrate diet, V) high cholesterol and/or VI) a high protein diet.

PolyQ AR knock-in mice can be selected that have modulations in some or all of the genes or markers, or particular levels of modulation for example as may be exhibited at different ages. The mammals can be used in screening assays described herein.

Metabolic Syndrome Related Liver Disease

Another aspect provided herein is a knock-in mouse for use as a liver disease model. Liver disease can develop subsequent to developing metabolic syndrome and as described in the Examples, the AR19Q mouse exhibits manifestations of liver disease.

In an embodiment, the polyQ AR knock-in mouse displays one or more of non-alcoholic fatty liver disease (NAFLD), chronic liver inflammation, non-alcoholic steatohepatitis (NASH), hepatitis, NASH fibrosis, NASH cirrhosis, hepatomegaly and/or hepatocellular carcinoma (HCC).

Figure 8A:
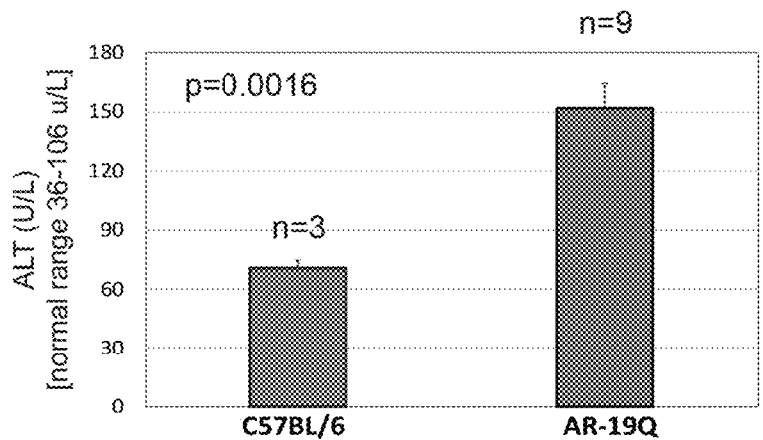
FIGS. 8A and 8B show NAFLD progression.

As described in FIG. 8, AR-19Q mice had increased alanine amino transferase (ALT) levels compared to wild type mice, which is indicated of hepatic damage. Also, AR-19Q mice all presented the fatty liver phenotype which progressed to nonalcoholic steatohepatitis (NASH) in older AR-19Q mice. Referring now to FIG. 9, AR-19Q mice presented other liver disease phenotypes such as NASH, macrovesicular steatosis, inflammation, and hepatocellular carcinoma (HCC).

In an embodiment, the polyQ AR knock-in mouse has an increased level of ALT compared to a control age-matched mammal lacking the recombinant AR cassette, by about 10%, about 20%, about 30%, about 40%, about 50%, about 60%, about 70%, about 80%, about 90% or greater than 100%.

Figure 10A:
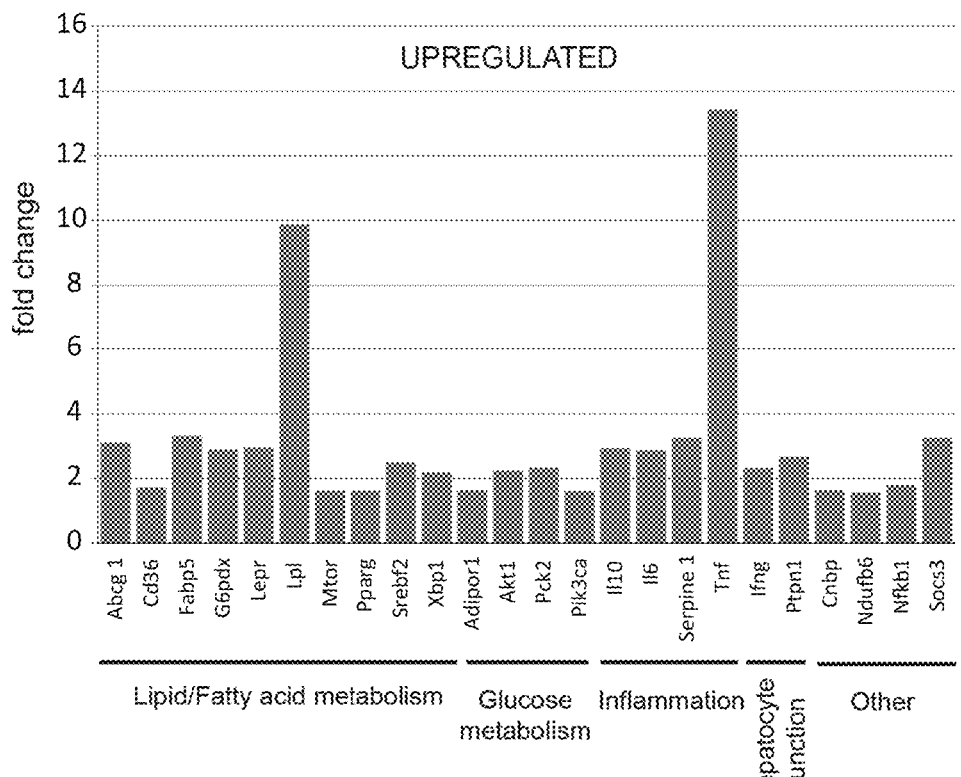
FIGS. 10A and 10B are graphs showing Liver Gene Profiling of the AR knock-in mouse. Analysis was carried out using a $RT^2$ Profiler PCR Array Mouse Fatty Liver platform from QIAGEN that allows for the analysis of 84 genes involved in the pathogenesis of fatty liver. Analysis performed on C57BL/6 (n=3), AR-19Q (n=8).
Figure 10B:
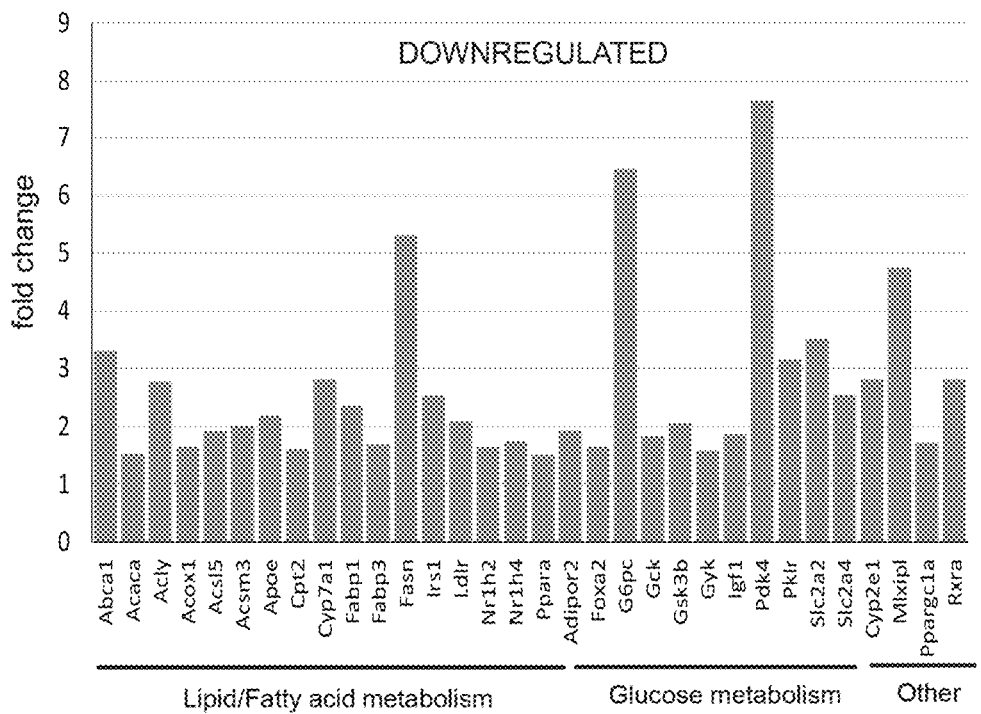

In FIG. 10, gene expression analysis was conducted to assess genes involved in the pathogenesis of fatty liver. At least one of the following genes involved in lipid/fatty acid metabolism were upregulated in AR-19Q mice: Abcg1, Cd36, Fabp5, G6pdx, Lepr, Lpl, Mtor, Pparg, Srebf2 and/or Xbp1 and at least one of the following were down regulated: Abca1, Acaca, Acly, Acox1, Acsl5, Acsm3, Apoe, Cpt2, Cyp7a1, Fabp1, Fabp3, Fasn, Irs1, Ldlr, Nr1h2, Nr1h4, Ppara.

Table 1 and 2 below show respectively the up-regulated and down-regulated genes in fatty liver in AR-19Q mice.

TABLE 1

Up-regulated genes in fatty liver in AR-19Q mice

| GENE NAME | ENTREZ ID | PROTEIN NAME |
| --- | --- | --- |
| Abcg1 | 11307 | ATP-binding cassette sub-family G member 1 |
| Adipor1 | 72674 | Adiponectin receptor protein 1 |
| Akt1 | 11651 | RAC-alpha serine/threonine-protein kinase |
| Cd36 | 12491 | Platelet glycoprotein 4 |
| Cnbp | 12785 | Cellular nucleic acid-binding protein |
| Fabp5 | 16592 | Fatty acid-binding protein, epidermal |
| G6pdx | 14381 | Glucose-6-phosphate 1-dehydrogenase X |
| Ifng | 15978 | Interferon gamma |
| Il6 | 16193 | Interleukin-6 |
| Il10 | 16153 | Interleukin-10 |
| Lepr | 16847 | Leptin receptor |
| Lpl | 16956 | Lipoprotein lipase |
| Mtor | 56717 | Mechanistic target of rapamycin (serine/threonine kinase) |
| Ndufb6 | 230075 | NADH dehydrogenase{ubiquinone} 1 beta subcomplex subunit 6 |
| Nfkb1 | 18033 | Nuclear factor NF-kappa-B p105 subunit |
| Pck2 | 74551 | Phosphoenolpyruvate carboxykinase [GTP], mitochondrial |
| Pik3ca | 18706 | Phosphatidylinositol 4,5-bisphosphate 3-kinase catalytic subunit alpha isoform |
| Pparg | 19016 | Peroxisome proliferator-activated receptor gamma |
| Ptpn1 | 19246 | Tyrosine-protein phosphatase non-receptor type 1 |
| Serpine1 | 18787 | Plasminogen activator inhibitor 1 |
| Socs3 | 12702 | Suppressor of cytokine signaling 3 |
| Srebf2 | 20788 | Sterol regulatory element-binding protein 2 |
| Tnf | 21926 | Tumor necrosis factor |
| Xbp1 | 22433 | X-box-binding protein 1 |

TABLE 2

Down-regulated genes in fatty liver in AR-19Q mice.

| GENE NAME | ENTREZ ID | PROTEIN NAME |
| --- | --- | --- |
| Abca1 | 11303 | ATP-binding cassette sub-family A member 1 |
| Acaca | 107476 | Acetyl-CoA carboxylase 1 |
| Acly | 104112 | ATP-citrate synthase |
| Acox1 | 11430 | Peroxisomal acyl-CoA oxidase 1 |
| Acsl5 | 433256 | Long-chain-fatty-acid-CoA ligase 5 |
| Acsm3 | 20216 | Acyl-CoA synthetase ACSM3, mitochondrial |

TABLE 2-continued

Down-regulated genes in fatty liver in AR-19Q mice.

| GENE NAME | ENTREZ ID | PROTEIN NAME |
|---|---|---|
| Adipor2 | 68465 | Adiponectin receptor protein 2 |
| Apoe | 11816 | Apolipoprotein E |
| Cpt2 | 12896 | Carnitine O-palmitoyltransferase 2, mitochondrial |
| Cyp2e1 | 13106 | Cytochrome P450 2E1 |
| Cyp7a1 | 13122 | Cholesterol 7-alpha-monooxygenase |
| Fabp1 | 14080 | Fatty acid-binding protein, liver |
| Fabp3 | 14077 | Fatty acid-binding protein, heart |
| Fasn | 14104 | Fatty acid synthase |
| Foxa2 | 15376 | Hepatocyte nuclear factor 3-beta |
| G6pc | 14377 | Glucose-6-phosphatase |
| Gck | 103988 | Glucokinase |
| Gsk3b | 56637 | Glycogen synthase kinase-3 beta |
| Gyk | 79223 | Glycerol kinase |
| Igf1 | 16000 | Insulin-like growth factor 1 |
| Irs1 | 16367 | Insulin receptor substrate 1 |
| Ldlr | 16835 | Low-density lipoprotein receptor |
| Mlxipl | 58805 | Carbohydrate-responsive element-binding protein |
| Nr1h2 | 22260 | Oxysterols receptor LXR-beta |
| Nr1h4 | 20186 | Bile acid receptor |
| Pdk4 | 27273 | Pyruvate dehydrogenase (acetyl-transferring) kinase isozyme 4 |
| Pklr | 18770 | Pyruvate kinase liver and red blood cell |
| Ppara | 19013 | Peroxisome proliferator-activated receptor alpha |
| Ppargc1a | 19017 | Peroxisome proliferator-activated receptor gamma coactivator 1-alpha |
| Rxra | 20181 | Retinoic acid receptor RXR-alpha |
| Slc2a2 | 20526 | Solute carrier family 2, facilitated glucose transporter member 2 |
| Slc2a4 | 20528 | Solute carrier family 2, facilitated glucose transporter member 4 |

In some embodiments the relevant readout is the level of gene expression of one or more glucose metabolism genes upregulated in AR-19Q mice selected from: Adipor1, Akt1, Pck2 and/or Pik3ca and/or at least one or more glucose metabolism genes down regulated in AR 19Q mice selected from: Adipor2, Foxa2, G6pc, Gck, Gsk3b, Gyk, Igf1, Pdk4, Pklr, Slc2a2 and Slc2a4.

In some embodiments the relevant readout is the level of gene expression of one or more genes involved in inflammation which were upregulated in AR-19Q mice selected from I110, I16, Serpine 1 and Tnf.

In some embodiments the relevant readout is the level of gene expression of one or more of the following genes involved in hepatocyte function which were upregulated in AR-19Q mice including lfng and/or Ptpn1.

In some embodiments the relevant readout is the level of gene expression of one or more of the following genes involved in liver disease which were upregulated in AR-19Q mice including Cnbp, Ndufb6, Nfkb1 and/or Socs3 and/or at least one of the following were down regulated including: Cyp2e1, Mlxipl, Ppargc1a, Rxra.

In an embodiment, the polyQ AR knock-in mouse selected for testing exhibits an up-regulation by at least 0.5 fold (e.g. a 50% increase), at least 1 fold, at least 1.5 fold, at least 2 fold, at least 2.5 fold, at least 3 fold, at least 3.5 fold, at least 4 fold, at least 4.5 fold, at least 5 fold, at least 6 fold, at least 7 fold, at least 8 fold, at least 9 fold, at least 10 fold, at least 11 fold, at least 12 fold, at least 13 fold or at least 14 fold, compared to a control age-matched mouse lacking the recombinant AR cassette, of at least one of the following genes: Abcg 1, Cd36, Fabp5, G6pdx, Lepr, Lpl, Mtor, Pparg, Srebf2, Xbp1, Adipor1, Akt1, Pck2, Pik3ca, Il10, Il6, Serpine 1, Tnf, lfng, Ptpn1, Cnbp, Ndufb6, Nfkb1 and/or Socs3.

In an embodiment, the polyQ AR knock-in mouse exhibits a down-regulation by at least 0.5 fold, at least 1 fold, at least 1.5 fold, at least 2 fold, at least 2.5 fold, at least 3 fold, at least 3.5 fold, at least 4, at least 5, at least 6 or at least 7 fold, compared to a control age-matched mammal lacking the recombinant AR cassette, of at least one of the following genes: Abca1, Acaca, Acly, Acox1, Acsl5, Acsm3, Apoe, Cpt2, Cyp7a1, Fabp1, Fabp3, Fasn, Irs1, Ldlr, Nr1h2, Nr1h4, Ppara, Adipor2, Foxa2, G6pc, Gck, Gsk3b, Gyk, Igf1, Pdk4, Pklr, Slc2a2, Slc2a4, Cyp2e1, Mlxipl, Ppargc1a and/or Rxra.

The mouse can be a male mouse or a female mouse. As female mice on HFD exhibit a similar metabolic phenotype as males, the gene expression pattern for such females would be expected to be similar.

PolyQ AR knock-in mammals can be selected that have modulations in some or all of the genes or markers, or particular levels of modulation for example as may be exhibited at different ages. The mammals can be used in screening assays described herein.

Prostate Disease

In a further embodiment, the polyQ AR knock-in mouse is a prostate disease mouse model.

In an embodiment, the mammal is a male mammal, optionally a male mouse.

Figure 6A:
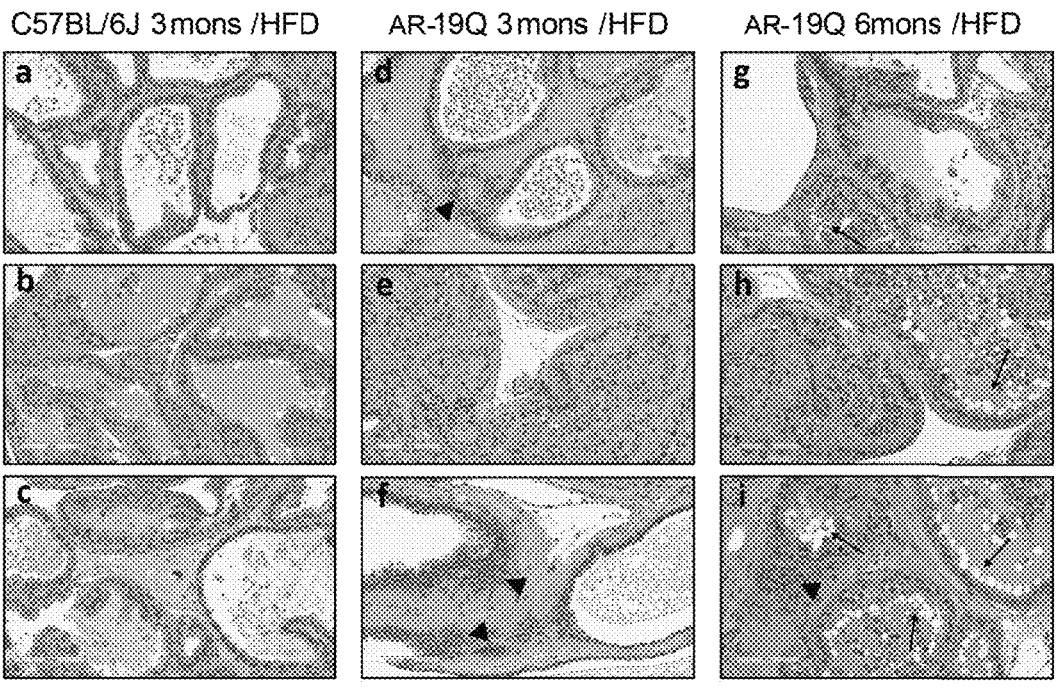
FIGS. 6A, 6B and 6C are images showing AR-19Q Prostate Histopathology.
Figure 6B:
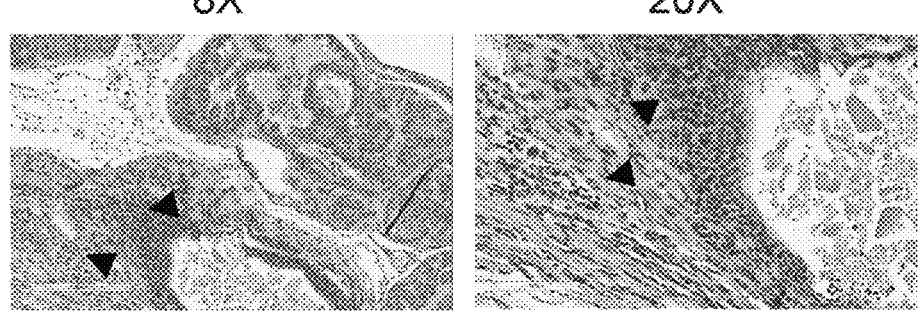

Referring now to FIG. 6, it was shown that AR-19Q mice have a high degree of benign prostatic hyperplasia (BPH)/hypertrophy with lymphocytic infiltration indicating an inflammatory process, prostatic intraepithelial neoplasia (PIN), and invasive adenocarcinoma compared to wild-type mice of similar age.

For example, the polyQ AR knock-in mouse displays prostate abnormalities, for example, high degree of benign prostatic hyperplasia (BPH)/hypertrophy with lymphocytic infiltration indicating an inflammatory process, prostatic intraepithelial neoplasia (PIN), and invasive adenocarcinoma.

As described in FIG. 7, certain genes commonly involved in prostate cancer are dysregulated in AR-19Q mice.

Table 3 and 4 below show respectively the up-regulated and down-regulated genes in prostate tissue in AR-19Q mice.

TABLE 3

Up-regulated genes in prostate tissue in AR-19Q mice

| GENE NAME | ENTREZ ID | PROTEIN NAME |
| --- | --- | --- |
| Abcb1b | 18669 | Multidrug resistance protein 1B |
| Acacb | 100705 | Acetyl-CoA carboxylase beta |
| Aldoc | 11676 | Fructose-bis-phosphate aldolase C |
| Atp4a | 11944 | Potassium-transporting ATPase alpha chain |
| Atp6v0d2 | 242341 | V-type proton ATPase subunit D2 |
| Atp6v1g3 | 338375 | V-type proton ATPase subunit G3 |
| Bcl2 | 12043 | B cell leukemia/lymphoma 2 |
| Bmp2 | 12156 | Bone morphogenetic protein 2 |
| Bpgm | 12183 | Bisphosphoglycerate mutase |
| Camkk1 | 55984 | Calcium/calmodulin-dependent protein kinase kinase 1, alpha |
| Ccl11 | 20292 | Eotaxin |
| Ccl12 | 20293 | C-C motif chemokine 12 |
| Ccl17 | 20295 | C-C motif chemokine 17 |
| Ccl19 | 24047 | C-C motif chemikine 19 |
| Ccl2 | 20296 | C-C motif chemokine 2 |
| Ccl20 | 20297 | C-C motif chemokine 20 |
| Ccl22 | 20299 | C-C motif chemokine 22 |
| Ccl24 | 56221 | C-C motif chemokine 24 |
| Ccl3 | 20302 | C-C motif chemokine 3 |
| Ccl4 | 20303 | C-C motif chemokine 4 |
| Ccl5 | 20304 | C-C motif chemokine 5 |
| Ccl6 | 20305 | C-C motif chemokine 6 |
| Ccl7 | 20306 | C-C motif chemokine 7 |
| Ccl8 | 20307 | C-C motif chemokine 8 |
| Ccl9 | 20308 | C-C motif chemikine 9 |
| Ccr1 | 12768 | C-C chemokine receptor type 1 |
| Ccr10 | 12777 | C-C chemokine receptor type 10 |
| Ccr2 | 12772 | C-C chemokine receptor type 2 |
| Ccr3 | 12771 | C-C chemokine receptor type 3 |
| Ccr5 | 12774 | C-C chemokine receptor type 5 |
| Ccr6 | 12458 | C-C chemokine receptor type 6 |
| Csf1 | 12977 | Macrophage colony-stimulating factor 1 |
| Csf3 | 12985 | Granulocyte colony-stimulating factor |
| Cx3cl1 | 20312 | Fractalkine |
| Cxcl1 | 14825 | Growth-regulated alpha protein |
| Cxcl10 | 15945 | C—X—C motif chemokine 10 |
| Cxcl13 | 55985 | C—X—C motif chemokine 13 |
| Cxcl15 | 20309 | C—X—C motif chemokine 15 |
| Cxcl5 | 20311 | C—X—C motif chemokine 5 |
| Cxcl9 | 17329 | C—X—C motif chemokine 9 |
| Cxcr3 | 12766 | C—X—C chemokine receptor type 3 |
| Cxcr5 | 12145 | C—X—C chemokine receptor type 5 |
| Cdkn1a | 12575 | Cyclin-dependent kinase inhibitor 1 |
| Cdkn2a | 12578 | Tumor suppressor ARF |
| Chrnb1 | 11443 | Acetylcholine receptor subunit beta |
| Cox6a2 | 12862 | Cytochrome c oxidase subunit VIa polypeptide 2 |
| Cox6b2 | 333182 | Cytochrome c oxidase subunit VIb polypeptide 2 |
| Cpt1b | 12895 | Carnitine O-oalmitoyltransferase 1, muscle isoform |
| Dab2ip | 69601 | Disabled homolog 2-interacting protein |
| Dkk3 | 50781 | Dickkopf-related protein 3 |
| Egr3 | 13655 | Early growth response protein 3 |
| Eno1 | 13806 | Alpha enolase |
| Eno2 | 13807 | Gamma enolase |
| Erg | 13876 | Transcriptional regulator ERG |
| Fasl | 14103 | Fas ligand |
| Gpat2 | 215456 | Glycerol-3-phosphate acyltransferase 2, mitochondrial |
| Gpx3 | 14778 | Glutathione peroxidase 3 |
| Hk2 | 15277 | Hexokinase-2 |
| Hk3 | 212032 | Hexokinase-3 |
| Il1b | 16176 | Interleukin-1 beta |
| Il1rn | 16181 | Interleukin-1 receptor antagonist protein |
| Il2rb | 16185 | Interleukin-2 receptor subunit beta |

TABLE 3-continued

Up-regulated genes in prostate tissue in AR-19Q mice

| GENE NAME | ENTREZ ID | PROTEIN NAME |
|---|---|---|
| Il2rg | 16186 | Cytokine receptor common subunit gamma |
| Il4 | 16189 | Interleukin-4 |
| Il6 | 16193 | Interleukin-6 |
| Il6ra | 16194 | Interleukin-6 receptor subunit alpha |
| Il6st | 16195 | Interleukin-6 receptor subunit beta |
| Il10ra | 16154 | Interleukin-10 receptor subunit alpha |
| Il10rb | 16155 | Interleukin-10 receptor subunit beta |
| Il11 | 16156 | Interleukin-11 |
| Il13 | 16163 | Interleukin-13 |
| Il16 | 16170 | Pro-Interleukin-16 |
| Il17b | 56069 | Interleukin-17B |
| Il33 | 77125 | Interleukin-33 |
| Msx1 | 17701 | Homeobox protein MSX-1 |
| Pf4 | 56744 | Platelet factor 4 |
| Pdk4 | 27273 | Pyruvate dehydrogenase kinase, isoenzyme 4, mitochondrial |
| Pfkfb3 | 170768 | 6-phosphofructo-2-kinase/fructose-2,6-biphosphate 3 splice variant 2 |
| Pfkl | 18641 | ATP-dependent 6-phosphofructokinase, liver type |
| Pklr | 18770 | Pyruvate kinase liver and red blood cell |
| Ppp2r2b | 72930 | Serine/threonine-protein phosphatase 2A 55 kDa regulatory subunit B beta |
| Prkaa2 | 108079 | 5'-AMP-activated protein kinase catalytic subunit alpha-2 |
| Prkar1b | 19085 | cAMP-dependent protein kinase type I-beta regulatory subunit |
| Prps2 | 110639 | Ribose-phosphate pyrophosphokinase 2 |
| Ptgs1 | 19224 | Prostaglandin-endoperoxide synthase 1 |
| Pygl | 110095 | Glycogen phosphorylase, liver form |
| Rbp1 | 19659 | Retinol-binding protein 1 |
| Sfrp1 | 20377 | Secreted frizzled-related protein 1 |
| Socs3 | 12702 | Suppressor of cytokine signaling 3 |
| Sox4 | 20677 | Transcription factor Sox-4 |
| Spp1 | 20750 | Osteopontin |
| Srebf1 | 20787 | Sterol regulatory element-binding protein 1 |
| Tfpi2 | 21789 | Tissue factor pathway inhibitor 2 |
| Tgfb1i1 | 21804 | Transforming growth factor beta-1-induced transcript 1 protein |
| Tnfrsf11b | 18383 | Tumor necrosis factor receptor superfamily member 11B |
| Tnfsf11 | 21943 | Tumor necrosis factor ligand superfamily member 11 |
| Tnfsf13b | 24099 | Tumor necrosis factor ligand superfamily member 13B |

TABLE 4

Down-regulated genes in prostate tissue in AR-19Q mice

| Abcb1a | 18671 | Multidrug resistance protein 1A |
|---|---|---|
| Acaca | 107476 | Acetyl-CoA carboxylase 1 |
| Acly | 104112 | ATP-citrate synthase |
| Adra2a | 11551 | Adrenergic receptor, alpha 2a |
| Aimp1 | 13722 | Aminoacyl tRNA synthase complex-interacting multifunctional protein 1 |
| Akt3 | 23797 | RAC-gamma serine/threonine-protein kinase |
| Aldob | 230163 | Fructose-bisphosphate aldolase B |
| Apc | 11789 | Adenomatous polyposis coli |
| Atp4b | 11945 | Potassium-transporting ATPase subunit beta |
| Atp12a | 192113 | Potassium-transporting ATPase alpha chain 2 |
| Atp6v1c2 | 68775 | V-type proton ATPase subunit C2 |
| Atp6v1e2 | 74915 | V-type proton ATPase subunit E2 |
| Casp3 | 12367 | Caspase-3 |
| Ccna1 | 12427 | Cyclin-A1 |
| Chrna1 | 11435 | Acetylcholine receptor subunit alpha |
| Csf2 | 12981 | Granulocyte-macrophage colony-stimulating factor |
| Fbp1 | 14121 | Fructose-1,6-bisphosphatase 1 |
| Fh1 | 14194 | Fumarate hydratase 1 |
| G6pc | 14377 | Glucose-6-phosphatase |
| Gck | 103988 | Glucokinase |
| Gys2 | 232493 | Glycogen synthase, liver |
| Hmgcr | 15357 | 3-hydroxy-3-methylglutaryl-CoA reductase |
| Hnf4a | 15378 | Hepatocyte nuclear factor 4-alpha |
| Il3 | 16187 | Interleukin-3 |
| Il5ra | 16192 | Interleukin-5 receptor subunit alpha |
| Il15 | 16168 | Interleukin-15 |
| Il17a | 16171 | Interleukin-17A |
| Il21 | 60505 | Interleukin-21 |
| Ints6 | 18130 | Integrator complex subunit 6 |
| Lgals4 | 16855 | Galectin-4 |
| Mapk1 | 26413 | Mitogen-activated protein kinase 1 |
| Mdh1b | 76668 | Putative malate dehydrogenase 1B |
| Mto1 | 68291 | Protein MTO1 homolog, mitochondrial |
| Ndufa1 | 54405 | NADH dehydrogenase[ubiquinone] 1 alpha subcomplex subunit 1 |
| Ndufb2 | 68198 | NADH dehydrogenase[ubiquinone] 1 beta subcomplex subunit 2 |
| Ndufb4 | 68194 | NADH dehydrogenase[ubiquinone] 1 beta subcomplex subunit 4 |
| Ndufs6 | 407785 | NADH dehydrogenase[ubiquinone] iron-sulfur protein 6 |
| Nrip1 | 268903 | Nuclear receptor-interacting protein 1 |
| Pck2 | 74551 | Phosphoenolpyruvate carboxykinase[GTP], mitochondrial |
| Pgk2 | 18663 | Phosphoglycerate kinase 2 |
| Prkag3 | 241113 | 5'-AMP-activated protein kinase subunit gamma-3 |
| Pten | 19211 | Phosphatase and tensin homolog |
| Rbm39 | 170791 | RNA-binding protein 39 |
| Sept7 | 235072 | Septin-7 |
| Shbg | 20415 | Sex hormone-binding globulin |
| Slc5a8 | 216225 | Sodium-coupled monocarboxylate transporter 1 |
| Uqcrq | 22272 | Cytochrome b-c1 complex subunit 8 |
| Vegfa | 22339 | Vascular endothelial growth factor A |

In an embodiment, the polyQ AR knock-in mouse exhibits an up-regulation by at least 0.5 fold, at least 1 fold, at least 1.5 fold, at least 2 fold, at least 2.5 fold, at least 3 fold, at least 3.5 fold, at least 4 fold, at least 4.5 fold, at least 5 fold, at least 6 fold, at least 7 fold, at least 8 fold, at least 9 fold, at least 10 fold, at least 11 fold, at least 12 fold, compared to a corresponding wild type mouse at least one of the following genes: Ccna1, Gnrh1, Ptgs1, Abcb1b, Cdkn2a, DIc1, Egr3, Gpx3, 116, Lgals4, Loxl1, Sfrp1, Slc5a8, Socs3, Bcl2, Cdknla, Cdkn2a, Dab2ip, Dkk3, Egr3, Erg, Gpx3, Loxl1, Msx1, Ptgs1, Rbp1, Sfrp1, Socs3, Sox4 and/or Tfpi2.

In an embodiment, the polyQ AR knock-in non-human mouse exhibits a down-regulation by at least 0.5 fold, at least 1 fold, at least 1.5 fold, at least 2 fold, at least 2.5 fold, at least 3 fold, at least 3.5 fold or at least 4 fold compared to a corresponding wild type mouse to at least one of the following genes: Ect2, Hal, Slc5a8, Arntl, Klkb1, Ptgs1, Abcb1a, Apc, Casp3, Ccna1, Cdh1, Gnrh1, Hmgcr, Ints6, Lgals4, Mapk1, Mto1, Nrip1, Pten, Rbm39, Sept7, Shbg and/or Vegfa, In an embodiment, one or more genes shown in FIG. 7 are measured to assess prostate changes in the polyQ AR knock-in mouse.

PolyQ AR knock-in mice can be selected for age, exhibition of a a phenotype, a modulations in or more genes or markers described herein, or particular levels of modulation for example as may be exhibited at different ages. The mammals can be used in screening assays described herein.

As the AR-19Q mice develop a prostatic phenotype including hyperplasia, the AR-19Q mice may be manipulated, for example genetically by crossing to other mutant mice, introducing cancer promoting genes optionally dominant active forms using for example a modified adenovirus system for long-term expression or optionally by diet hormone replacement therapy or other treatment, to illicit prostate cancer. Such manipulated mice may also be used in screening assays described herein.

Cardiovascular Disease

In yet another embodiment, the polyQ AR knock-in mouse is a cardiovascular disease model. For example, as described above, the mammal displays hypertension, obesity, diabetes and/or hyperlipidemia. For example, the mammal has elevated triglyceride and LDL cholesterol levels.

In an embodiment, the mammal is a male mammal, optionally a male mouse.

PolyQ AR knock-in mammals can be selected that have modulations in some or all of the genes or markers, or particular levels of modulation for example as may be exhibited at different ages. The mammals can be used in screening assays described herein.

In addition, as described in FIG. 7, genes involved in glucose metabolism, AMPK signaling, mitochondria energy metabolism and inflammatory processes are altered. These genes may be relevant for each of the models described herein.

Ovarian Disease and Accompanying Infertility Phenotype

As demonstrated herein, the polyQ AR female knock-in mice exhibit an ovarian disease.

Figure 12:
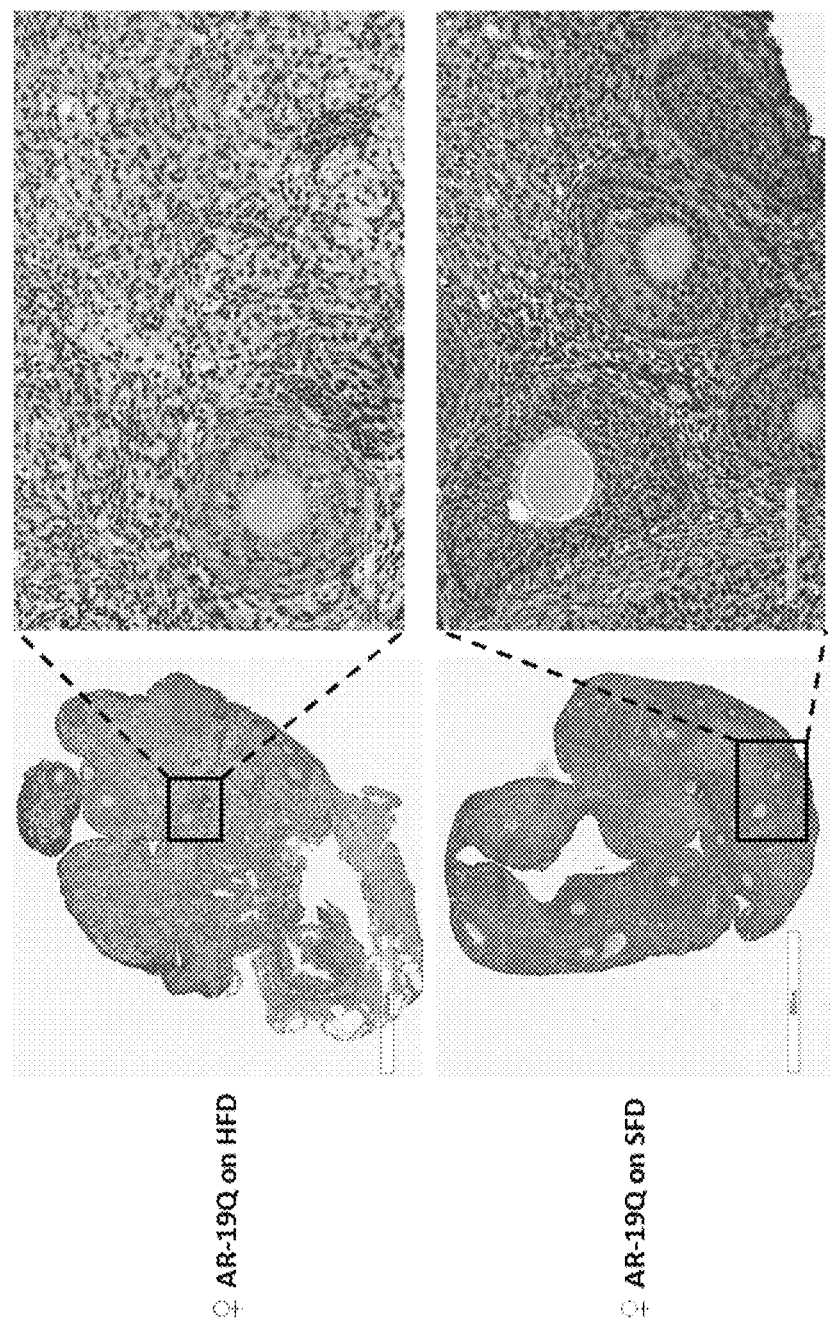
FIG. 12 is a series of images showing ovarian disease in female AR-19Q mice. Ovaries dissected from female AR-19Q mice on a high-fat diet stained by H/E. Ovaries display significant fat infiltration compared to their wild-type counterparts. Moreover, follicle cells surrounding the oocyte also show significant fat ballooning.

Referring now to FIG. 12, the AR-19Q knock-in female mice on HFD presented ovarian disease phenotype with strong fat infiltration. Another example, these female AR-19Q knock-in mice on HFD were also accompanied by an infertility phenotype. Accordingly, female mice can be used to assess fertility treatments and treatments that reduce ovarian fat infiltration. Suitable readout for such a model is for example restoration of fertility and/or decrease in ovarian fat.

Any of the described expression products or changes described can be assessed in various screening assays.

An aspect includes a method for discovering a preventive or therapeutic regimen for the prevention or treatment of a disease described herein, optionally metabolic syndrome, type 2 diabetes mellitus, and/or hypertension, comprising the steps of:

feeding a polyQ AR knock in mouse (e.g. a mouse comprising a recombinant AR cassette) with a diet, optionally a high caloric diet; before during and/or after the diet, treating the mouse with the preventive or therapeutic regimen; and assessing one or more relevant disease readouts such as weight gain, triglycerides, HDL, hypertension, and/or hyperglycemia compared to a control mouse, e.g. an aged matched polyQ AR knock in mouse fed the same diet not treated with the preventive or therapeutic regimen.

In some embodiments, the preventive or treatment regimen comprises an alteration in diet or activity.

In some embodiments, the preventive or treatment regimen comprises contacting the recombinant cell or administering the polyQ AR knock in mouse a test compound.

An aspect provided herein is a method of screening for putative preventive or treatment for treating metabolic syndrome, metabolic syndrome related liver disorder, type 2 diabetes mellitus, prostate disease, and/or ovarian disease and accompanying infertility, comprising:

a. contacting a test compound and/or change in media components reflective of a diet change with a recombinant cell described herein;

b. contacting a test compound and/or change in media components reflective of a diet change with a recombinant tissue described herein;

c. administering one or more doses of the test compound to a knock-in mouse described herein; or d. iii) altering a diet of a polyQ AR knock in mouse, optionally in combination with iii) prior to or after administering the one or more doses of the test compound; and determining any effect of the test compound and/or diet, on the recombinant cell, tissue or knock-in mouse compared to suitable control, optionally untreated control cells or untreated age-matched control animals.

Typically, the test compound is contacted with the recombinant cells in tissue culture assays where the cells are grown in standard media. The recombinant tissue is also typically contacted with the test compound in a nutrient media. Changes in media components reflective of diet change can be tested with or with addition of a test compound.

In an embodiment, untreated control cells are vehicle treated recombinant cells or tissue derived the same knock in mouse genotype, optionally from the AR-19Q knock-in mouse.

In an embodiment, untreated age-matched control animals are vehicle treated knock-in mouse.

In an embodiment, the recombinant cell is an AR-19Q mouse cell, the recombinant tissue is isolated or derived from an AR-19Q mouse tissue or knock in mouse, and the knock-in mouse is an AR-19Q mouse.

In an embodiment, infertility is assessed by mating female and/or male polyQ AR knock in mice with wild type mice and assessing if the mice get pregnant, how long to pregnancy, hormone levels associated with pregnancy or any other relevant readout related to pregnancy.

In an embodiment, the test compound, preventive or therapeutic regimen and/or diet, is for weight loss and an effect measured in the mammal is a decrease in weight, optionally a decrease in volume of fat pads, optionally epididymal or subcutaneous fat pads.

In an embodiment, the test compound, preventive or therapeutic regimen and/or diet, is for treating hypertension and an effect measured in the mammal is a decrease in blood pressure, optionally systolic or diastolic blood pressure. In other embodiments, the expression pattern of the recombinant cell or tissue is assessed.

In an embodiment, the test compound, preventive or therapeutic regimen and/or diet, is for treating T2D and an effect measured in the mammal is a decrease in glycemia, optionally post-prandial hyperglycemia and/or fasting hyperglycemia, and/or a decrease in insulin resistance, optionally measured by a decrease in glucose tolerance test (GTT).

In an embodiment, the test compound, preventive or therapeutic regimen and/or diet, for treating T2D and an effect measured in the mammal is no change (e.g. no increase) in pancreatic volume, optionally as measured by histopathology, or an increase in insulin content in the pancreas and/or increase in glucagon in the pancreas.

In an embodiment, the test compound, preventive or therapeutic regimen and/or diet, is for treating hypertriglyceridemia in the mammal and an effect measured is a decrease in triglyceride levels, optionally a decrease in lipoprotein lipase (LPL) levels.

In an embodiment the test compound, preventive or therapeutic regimen and/or diet, is for treating liver disease related to metabolic syndrome in the mammal and an effect measured is improved liver function, optionally as determined by liver enzyme activity, optionally alanine aminotransferase (ALT) AST, ALP and/or GGT levels, and/or a decrease in liver volume and content, optionally as measured by histopathology or ultrasound.

In an embodiment the test compound, preventive or therapeutic regimen diet, and/or light environment, is for treating prostatic disease, optionally prostatic hyperplasia, prostatic hypertrophy, prostatic neoplasia, optionally prostatic interepithelial neoplasia or prostatic interepithelial neoplasia, prostatic neoplasia in situ, prostatic hyperplasia lymphocytic infiltration, and the effect measured is a change in prostate morphology and/or an increase in volume, optionally as measured by microscopy.

In an embodiment, the method comprises administering the test compound, preventive or therapeutic regimen and/or diet, t, to the polyQ AR knock-in cell, tissue or mouse and measuring the levels of gene expression as described above, for example by conducting gene expression analysis as described in FIG. 7 (Table 3 and 4) and 10 (Table 1 and 2). For example, in genes that are up-regulated in polyQ AR knock-in cells or mammals, the effect measured for a test compound is a decrease in expression of said genes compared to an untreated control. In genes that are down-regulated in polyQ AR knock-in cells or mammals, the effect measured for a test compound is an increase in expression of said genes compared to an untreated/placebo control.

For example, the test compound, preventive or therapeutic regimen and/or diet, is for treating prostatic disease and an effect measured effect is a decrease in expression of by at least 0.5 fold, at least 1 fold, at least 1.5 fold, at least 2 fold, at least 2.5 fold, at least 3 fold, at least 3.5 fold, at least 4 fold, at least 4.5 fold, at least 5 fold, at least 6 fold, at least 7 fold, at least 8 fold, at least 9 fold, at least 10 fold, at least 11 fold or at least 12 fold of at least one of the following genes.

For example, the test compound, preventive or therapeutic regimen and/or diet, is for treating prostatic disease and an effect measured is an increase in expression by at least 0.5 fold, at least 1 fold, at least 1.5 fold, at least 2 fold, at least 2.5 fold, at least 3 fold, at least 3.5 fold or at least 4 fold to at least one of the following genes: Ect2, Hal, Slc5a8, Arntl, Klkb1, Ptgs1, Abcb1a, Apc, Casp3, Ccna1, Cdh1, Gnrh1, Hmgcr, Ints6, Lgals4, Mapk1, Mto1, Nrip1, Pten, Rbm39, Sept7, Shbg, Vegfa, Acly, Aldob, Fbp1, Fh1, G6pc, Gck, Gys2, Mdh1b, Pck2, Pgk2, Acaca, Adra2a, Akt3, Chrna1, Gys2, Hnf4a, Prkag3, Atp12a, Atp4b, Atp6v1c2, Atp6v1e2, Ndufa1, Ndufb2, Ndufb4, Ndufs6, Uqcrq, Aimp1, Csf2, Il15, IL17a, Il21, Il3 and/or Il5ra, compared to an untreated control.

For example, the test compound, preventive or therapeutic regimen and/or diet, is for treating liver disease and an effect measured is a decrease by at least 0.5 fold, at least 1 fold, at least 1.5 fold, at least 2 fold, at least 2.5 fold, at least 3 fold, at least 3.5 fold, at least 4 fold, at least 4.5 fold, at least 5 fold, at least 6 fold, at least 7 fold, at least 8 fold, at least 9 fold, at least 10 fold, at least 11 fold, at least 12 fold, at least 13 fold or at least 14 fold, to at least one of the following genes: Abcg 1, Cd36, Fabp5, G6pdx, Lepr, Lpl, Mtor, Pparg, Srebf2, Xbp1, Adipor1, Akt1, Pck2, Pik3ca, Il10, Il6, Serpine 1, Tnf, Ifng, Ptpn1, Cnbp, Ndufb6, Nfkb1 and/or Socs3, compared to an untreated control.

For example the test compound, preventive or therapeutic regimen and/or diet, is for treating liver disease and an effect measured is an increase by at least 0.5 fold, at least 1 fold, at least 1.5 fold, at least 2 fold, at least 2.5 fold, at least 3 fold, at least 3.5 fold, at least 4, at least 5, at least 6 or at least 7 fold, to at least one of the following genes: Abca1, Acaca, Acly, Acox1, Acsl5, Acsm3, Apoe, Cpt2, Cyp7a1, Fabp1, Fabp3, Fasn, Irs1, Ldlr, Nr1h2, Nr1h4, Ppara, Adipor2, Foxa2, G6pc, Gck, Gsk3b, Gyk, Igf1, Pdk4, Pklr, Slc2a2, Slc2a4, Cyp2e1, Mlxipl, Ppargc1a and/or Rxra, compared to an untreated control.

For example, the AR-19Q knock-in mouse, recombinant tissue or recombinant cell is derived from aAR-19Q mouse, tissue or cell and the control is an AR-19Q mouse or cell that was not treated/contacted with said putative treatment. For example, if liver disease related genes, normally up-regulated in AR-19Q mice or derived recombinant cell or tissue, exhibit a decrease in expression following administering of a treatment (e.g. a decrease compared to an untreated AR-19Q mouse), then the compound is considered to be effective for treating liver disease.

In other embodiments, the effect measured of the test compound, preventive or therapeutic regimen and/or diet, is a similarity of physiological/functional parameters, parameters, gene expression levels, etc. of the polyQ AR knock-in mouse compared to a wild type age controlled mouse. For example, if following treatment for treating obesity, the weight of the AR-19Q mouse decreases such that it is similar to the weight of a wild type age-controlled mouse of the same strain, then the compound is considered to be effective for treating obesity.

In an embodiment, the test compound, preventive or therapeutic regimen and/or diet, is tested in combination with an existing therapeutic.

In another embodiment, the test compound, preventive or therapeutic regimen, is an existing therapeutic.

In an embodiment, the effect of the test compound and/or diet, is determined after 1, 7, 14, 21, 28 days and/or 1, 2, 3, 6, and/or 9 months of treatment.

As described herein the polyQ mouse models described herein may be validated as disease models, for example to confirm that the models correlate with clinical trials.

For example, the AR-19Q mice are treated with therapeutic compounds, for example elafibranor, MSCD-0602L or obeticholic acid, to assess the AR-19Q mouse disease model correlation with clinical trials. AR-19Q mice exhibiting a NAFLD Activity Score of greater than 4 are determined suitable for treatment.

In an embodiment, the polyQ mouse model is used as a pre-clinical model, for example for in-vivo testing of therapeutic compounds and/or diets for treating metabolic syndrome, type 2 diabetes mellitus, metabolic syndrome related liver disease, prostatic disease, ovarian disease and accompanying infertility, and cardiovascular disease. For example, the models may be used to identify biomarkers involved in the disease disclosed herein.

In an embodiment, the polyQ mouse model is used as a pre-clinical model, for treating metabolic syndrome, type 2 diabetes mellitus, metabolic syndrome related liver disease, prostatic disease, ovarian disease, and cardiovascular disease. For example, the models may be used to identify biomarkers involved in the disease disclosed herein.

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1: AR-19Q Mouse

The Androgen Receptor Protein and its Polyglutamine Tract

The X-linked androgen receptor (AR) protein is a member of the nuclear receptor superfamily. It is a ligand-inducible transcription factor containing a polymorphic N-terminal region, a central DNA-binding domain (DBD) and a C-terminal ligand-binding domain (LBD) (FIG. 1A).

The structurally flexible N-terminal domain (NTD), harbours a long polymorphic polyglutamine (polyQ) tract (n=11-33). Encoded by a genomic CAG repeat, it helps modulate AR transcriptional activity; ARs with shorter polyQ tracts are the most transcriptionally active[6,7]. This functional polymorphism has now been well documented to participate in all facets of androgen physiology and is an independent factor affecting almost every aspect of both AR reproductive and non-reproductive biology both in males and females (PubMed >1000 references).

Trinucleotide repeats are genomically very unstable, i.e., they can easily expand or contract in length in somatic cells. This exceeds, by many orders of magnitude, the comparative genetic stability of common nucleotide sequences. Using laser microdissection significant somatic AR CAG repeat instability in prostate[8,9] and breast[10] pathology including short AR CAG repeat lengths were documented, and polyGln tract deletions were found, which would result in a superactive AR.

AR-19Q Knock-in Mouse: A Metabolic Syndrome Mouse

The mouse AR shares over 90% homology with the human ortholog, but interestingly lacks the CAG encoded-polyglutamine tract; instead mice possess a mixed CAG/CAA/CAC-glutamine/histidine tract. To study AR functionality in a more structured fashion, including the newly identified AR properties, a knock-in mouse model that would have the equivalent of human polyQ tract was created. This would allow to study AR functions in more controlled experimental conditions and at the same time assess the impact of polyQ in overall reproductive physiology. A similar attempt to humanize the AR in mouse has been done previously; a knock-in mouse model was created by replacing all of mouse exon one with human exon one[1], a rather large and drastic change considering both exon ones have more than 400 amino acids. This particular whole exon 1 knock-in mouse model (21Q tract) does not have an obvious phenotype, but when crossed with the TRAMP prostate mouse model it showed that the presence of a CAG tract accelerates prostate neoplasia but minimally. A more precise humanized mouse AR model was made by replacing only the mouse 19-glutamine/histidine tract with the human pure 19-glutamine tract by knock-in methodology.

Generating the Targeting Vector for Transfection of ES Cells.

To construct the targeting vector, sequences from the ploxPneo-1 plasmid and pPGKneo-NTR-tkpA plasmid were used. The pPGKneo-NTR-tkpA plasmid encodes the neomycin resistance (neo$^r$) and herpes simplex virus-thymidine kinase (hsv-tk) selectable genes with the 5' nontranslated region (NTR) of encephalomyocarditis virus inserted in between.

To generate the targeting vector, the PGK-neo cassette in ploxPneo-1 was replaced with the neo-NTR-hsv-tk sequences from pPGKneoNTR-tkpA as follows:

Five micrograms of ploxPneo-1 plasmid were partially digested with Xba I (37° C./16 h). Xba I was heat inactivated for 20 min at 65° C. and the ends were blunted using Klenow polymerase (37° C./10 min). The DNA was then completely digested with Blp I (37° C./16 h). Five micrograms of pPGKneoNTR-tkpA plasmid was digested with Nsi I (37° C./16 h). Enzyme was inactivated by heating at 65° for 20 min and the ends were blunted with T4 polymerase (RT/5 min). The DNA was then digested with Blp I (37° C./16 h).

The Nsi I-Blp I fragment was ligated to the Xba I-Blp I vector backbone using T4 DNA ligase (RT/4 h), such that the neo-hsv-tk fragment removed from pPGKneoNTR-tkpA was introduced into the ploxPneo-1 vector, flanked by two loxP sites. Ligation was confirmed by restriction enzyme digestion.

Constructing 3' and 5' Mouse AR Genomic DNA Clones.

Mouse AR mRNA (NM_013476) was used to search Genbank using BLAST. A 17,202-base pair long Sanger assembly f162083 was found. f162083 is the contig of a number of different BAC clones, including RPCI-23-191K6 (191K6 BAC clone) and RPCI-23-259K23 (259K23 BAC clone), which contain different mouse AR genomic DNA fragments. 191K6 BAC clone contains the 5' untranslated region and its sequenced region starts at bp 1311 of f162083 and ends at bp 1775. 259K23 BAC clone starts at exon 1 and continues up to exon eight of the mouse AR gene. Its sequence region starts at bp 4470 of f162083. The ORF of the AR starts at bp 4470 of f162083.

Verification of the clones for AR sequences was carried out by PCR.

191K6 or 259K23 were used as DNA template and a set of specific primers used:

```
TR12404A
                                       (SEQ ID NO: 1)
(FWD: 5'-ACGAGGCCGGCACCATGCAACTTCTC-3')
and TR12404B
                                       (SEQ ID NO: 2)
(REV: 5'-CTTCGTCCAGGGGAAGACCTTT-3').
```

PCR was done using Vent DNA polymerase in a total reaction volume of 50 µl. After initial denaturation at 94° C./45 s, 36 cycles (94° C./45 s; 55° C./45 s; 72° C./1 min) were carried out. The product of PCR was predicted to be a 317 bp fragment.

The 191K6 BAC clone contains 4 Bgl II sites according to the fl62083 assembly, located at bp 891, bp 1651, bp 6310, and at bp 12601.

The interval from 1651 to 6310 (4.6 kb) includes the 5' UTR, exon 1 and 300 bp downstream of exon 1 of the mouse AR gene. The interval from 6310 to 12601 (6.2 kb) includes intron 1 sequence. The 191K6 BAC clone was digested with Bgl II (37° C./16 h) and run in a 1% agarose gel. The 4.6 kb and 6.2 kb bands were excised, and the DNA extracted.

Confirmation that the right bands had been excised was done by Southern blot using the PCR fragments of 191K6 and 259K23 clones as probes.

The 4.6 kb piece is referred to as the 5'-end AR sequence.

The 6.2 kb piece is referred to as the 3'-end AR sequence.

Both pieces, 4.6 kb and 6.2 kb, were subcloned into the pcDNA3 vector.

pcDNA3 was opened by digesting it with Bam HI, dephosphorylated with Calf Intestinal Alkaline Phosphatase to remove the 5'-phosphate group.

The product of Bam HI digestion was run in agarose gel containing guanosine. Band was excised and the DNA extracted. The Bgl II-Bgl II 5'-end was then ligated into pcDNA3. Clones were screened by Southern blot using the 191K6 PCR product as probe. Southern blot results were confirmed by restriction enzyme digestion.

Similar procedure was used to subclone the 3'-end into the pcDNA3 vector.

To confirm that the 3'-end and 5'-end AR fragments were intact in pcDNA3, positive clones were sequenced using the Thermo Sequenase Radiolabeled Terminator Cycle sequencing kit. The Sp6 primer (REV: 5'-AGCATTTAGGTGACACTATAGAATAG-3') (SEQ ID NO: 3), downstream of Bam HI (pcDNA3 cloning site) was used for sequencing.

Creating the 19 CAG Tract.

A pSVhAR.BHEX plasmid containing 19 CAG repeats and 1 CAA, which had been created in the laboratory, was used as template for PCR to amplify the CAG repeat.

Specific primers flanking the CAG tract were used:

```
Primer 1.15A
                                       (SEQ ID NO: 4)
(FWD: 5'-GTTCCAGAGCGTGCGCGAAGT-3').

Primer 1.15B
                                       (SEQ ID NO: 5)
(REV: 5'-TGGGGCCTCTACGATGGGCTT-3').
```

The PCR reaction consisted of an initial denaturation step at 94° C./45 s followed by 36 cycles (94° C./45 s; 55° C./45 s; 72° C./1 min). The PCR product was loaded into a 2.3% agarose gel and the sample is fractionated. The right product is approximately 230 bp.

The band was excised and the DNA extracted and then digested with Alw261 (37° C./16 h), which site is downstream of the CAG repeat.

Klenow polymerase was used to fill in using only dATP/dGTP. The end was blunted using Mung Bean Nuclease (30° C./30 min)

The DNA was then digested with HpyCH4V (37° C./16 h), upstream of the human CAG repeat.

These procedures produced a blunt ended fragment containing only 19 CAG repeats, without flanking sequences.

Changes in the CAG repeat length due to PCR artifacts gave as results fragments with 18 CAG repeats, which upon ligation with the 19 CAG repeat fragment produced an insert with 37 CAG repeats.

In order to subclone different CAG repeat lengths into the 5'-AR, the 5'-end AR 0 CAG cloned in pUC19 was opened at the Xho I site (37° C./16 h), filled in using Klenow polymerase with dTTP/dCTP only (37° C./15 min), and then blunted using Mung Bean nuclease (30° C./30 min) in order to keep the ORF.

Subsequently, different length CAG fragments were cloned into the opened vector.

Resulting clones were screened by restriction enzyme digestion.

Results indicated that there were two clones containing 19 CAG repeats, a single clone containing 18 CAGs, and a single clone containing 37 CAGs in the correct orientation and reading frame.

Introducing the 3'-End AR Fragment into pPGKneoNTR-tkpA-Plox.

The 3'-end of the AR was obtained by digesting the pcDNA3-3'end clone with Kpn I (37° C./16 h) restriction site in pcDNA3 and SnaB I (37° C./16 h) site in the AR. After digestion the Kpn I site was blunted with T4 DNA polymerase (RT/15 min).

The pPGKneoNTR-tkpA-plox vector was opened with Xho I (37° C./16 h) and then blunted.

The 3'-end AR released from pcDNA3 is then subcloned into the pPGKneoNTR-tkpA-plox to produce a new construct, pPGKneoNTR-tkpA-plox-3'-AR, of approximately 11 kb. (FIG. 1B)

Mouse 129/SV embryonic stem (ES) cells were electroporated with the AR 19 CAG knock-in vector. PCR was used to confirm homologous recombination had taken place in certain ES clones. Specific 19 CAG ES clones were electroporated with Cre recombinase. Following PCR screening a number of ES clones in which the neo-tk cassette had been correctly excised were identified. Positive ES cells were used for blastocyst injections and chimeric mice obtained.

25 chimeras from four 19-CAG clones were obtained. Only males with ≥80% chimerism were mated with C57BL/6 females. Females of the F1 generation were genotyped and positive females were back-crossed with C57BL/6 males. Back-crossing continued until the appearance of positive males for the AR-19Q allele in the F7 generation (FIG. 1C/1D). Males positive for the AR-19Q allele were mated with heterozygous females and their litters genotyped. Homozygous females were obtained in F10. Since then it has been possible to breed pure homozygous AR-19Q knock-in mice.

Constructing the 0 CAG Repeat.

In order to make 0 CAG in exon 1 of the mouse AR gene, PCR methodology was used.

Two specific primers were made:

```
Primer #1
                                    (SEQ ID NO: 6)
(FWD: 5'-ACGAGGCCGGCACCATGCAACTTCTCGAGGTAATCTC
CGAAGGCAGC-3')
``` which starts 26 bp upstream of CAG/CAA/CAC repeat, skips over the CAG/CAA/CAC repeat and continues 21 bp downstream of it. One single T bp was change to C to create an Xho I site for future manipulations.

```
Primer #2
                                    (SEQ ID NO: 2)
(REV: 5'-CTTCGTCCAGGGGAAGACCTTT-3')
```

191K6 or/and 259K23 BAC clones were used as DNA templates.

PCR reaction consisted of an initial denaturation at 94° C./2 min, followed by 35 cycles (96° C./45 s, 60° C./30 s, 72° C./1 min).

PCR product lacked the mouse CAG/CAA/CAC repeat.

Introducing 0 CAG Fragment into the 5'-End AR Fragment.

The 5'-end fragment (4.6 kb) was taken out from the pcDNA3 plasmid and introduced into the pUC19 cloning vector.

Ten micrograms of pcDNA3 were digested with Kpn I and Not I (37° C./16 h), and blunted with T4 DNA polymerase (RT/5 min).

pUC19 was opened with Sma I (25° C./16 h) and then dephosphorylated with CIP (37° C./15 min).

The Kpn I/Not I fragment from pcDNA3 was ligated into the pUC19 vector using T4 DNA ligase (RT/16 h).

The pUC19 vector containing the 5'-end fragment was the digested with Bsm I (sticky ends) (65° C./5 h) and partially with Nae I (blunt) (37° C./2 h).

The PCR fragment lacking the CAG/CAA/CAC repeat (0 CAG) was also digested with Bsm I and Nae I, and then ligated into the 5'-end fragment in pUC19 using T4 DNA ligase (RT/16 h).

A positive clone was sequenced using the TR12404B primer (REV: 5'-CTTCGTCCAGGGGAAGACCTTT-3') (SEQ ID NO: 2) and also a second primer called preCAG (FWD: 5'-CCAGGCTTAAGCAGCTGCTCCG-3') (SEQ ID NO: 7), which anneals upstream of the Xho I site that was created.

Sequencing results indicated that the positive clone had three Bsm I-Nae I insert, that correspond to one 0 CAG and two multiple CAG repeats.

In order to eliminate the two multiple CAG repeats, the clone was digested with Avr II (37° C./16 h), giving as a result the obtention of four pieces.

Two small bands (<500 bp) corresponding to the extra inserts, which had to be eliminated.

The two largest bands corresponds to the vector itself (6.3 kb) and to the correct insert (1.6 kb), and they were excised, the DNA extracted, dephosphorylated with CIP (37° C./15 min) and religated to each other using T4 ligase (RT/16 h).

To confirm that the ligation worked properly, resulting clones were sequenced using the primer preCAG (FWD: 5'-CCAGGCTTAAGCAGCTGCTCCG-3') (SEQ ID NO: 7), which is upstream of the Xho I site.

Results indicated the presence of a unique Xho I site and lacking of the CAG/CAA/CAC repeat. (FIG. 2A).

Creating Various Lengths of CAG Tract

Introducing Different Lengths of CAGs into the Targeting Vector.

The 5'-end AR clones in pUC19, which included the different length CAG repeats, were digested with EcoRV (37° C./16 h), run in a 2% agarose gel and then extracted.

The linearized vector was then digested with Sac I (37° C./16 h), and then the ends blunted with T4 polymerase (RT/5 min). The product was run in a 2% gel and two bands were observed. The upper band (4.6 kb) that corresponded to the 5'-end AR fragment containing the CAG repeat was extracted. The extracted fragment, either containing 0, 19 or 37 CAG or the mixed repeats, 19 CAG/CAC or 40 CAG/CAC, was subcloned into the pPGKneoNTR-tkpA-plox-3'-end AR vector that had been digested with BamHI and blunted with Klenow polymerase. Ligation was done using T4 DNA ligase (RT/16 h). Clones were screened by restriction enzyme digestion. Confirmation of the right CAG tract length was done by sequencing.

The 0Q tract was lethal in male and female mice and only females heterozygous for the expanded 39Q tract survived.

To assess the impact of introducing the 19Q tract into the mouse AR (mAR), a 19Q mAR construct was used in transactivation assays; the mAR-19Q construct demonstrated slightly higher transactivation properties than the wild-type mAR vector at identical androgen ligand concentrations (FIG. 3). The stability of the CAG repeat of the mouse has been analyzed and shown to be stable.

AR-19Q Phenotype

The AR-19Q mice phenotype can be best described as a mice counterpart to the Metabolic Syndrome or MetS, reflecting the dependence on androgens as well as the AR 19Q tract; to date castrated mice have not expressed the phenotype. Females have not yet been challenged with estrogen depletion (castration) or androgen supplementation. No reproducible phenotype was initially observed in females (see ovarian phenotype described below). Penetrance of the phenotype in males is very high (>95%). All mice are fed completely normal chow. The first obvious characteristic is the appreciable gain of weight, commencing at 3 months (FIG. 4A). The extent of obesity and weight gain is significant, with the 19Q mice displaying 40% greater weight vs. C57BL5 mice (FIG. 4B). To assess obesity status we weighed fat pads, epididymal, subcutaneous, and brown adipose tissue vs. age-matched controls (FIG. 4C). The 19Q mice first appear to have post-prandial hyperglycemia and eventually develop moderate fasting hyperglycemia, as seen from glucose tolerance tests and elevated blood glucose levels (FIGS. 4D/4E). Moreover, abdominal ultrasound reveals hepatomegaly and features of a fatty liver, without ascites fluid accumulation. The mice soon after having documented systolic hypertension that persists throughout their lifespan (FIG. 4F).

Example 2: Metabolic Syndrome Mouse Model and Type 2 Diabetes (T2D) and Islet n-Cell Failure Model Pioneer studies clearly demonstrated that T2D is a "in continuum" disease entity that primarily starts with peripheral insulin resistance with normal serum glucose dynamics, although at the expense of higher circulating insulin levels. This demand is reflected by higher insulin production and by the sine qua non finding of islet hyperplasia. There are very few pathological sequelae at this stage and it is only when insulin demands are not met that postprandial hyperglycemia, and eventually frank hyperglycemia, is seen. Late stage disease is marked by significant loss of insulin production and islet accumulation of amyloid material. The critical element responsible for initiation of disease entities associated with diabetes is islet β-cell failure. Thus, insulin resistance in target tissues, combined with a relative deficiency of insulin secretion from pancreatic islet β-cells, are the major features of T2D. Under physiological conditions, when insulin sensitivity decreases, insulin secretion increases to maintain normal glucose levels; when insulin secretion fails to compensate, abnormal glucose tolerance develops and further progression to overt T2D is characterized by severe β-cell dysfunction.

Islet cell dysfunction remains the pivotal event in T2D. The molecular mechanisms responsible for islet β-cell failure remain elusive and few models offer the opportunity to make progress towards unraveling its pathophysiology. The mouse model described in Example 1 is relevant to T2D, is more physiological (lacks significant genetic alterations, no dietary manipulation is needed, no hyperphagia is seen) and is a clear departure from other models.

It is proposed that glucose metabolism in the β islets is accelerated in the polyQ AR mice, provoked by either insulin resistance and/or hyperglycemia itself, leading to excessive mitochondrial ROS, cell stress, metabolic alterations and subsequent cellular damage, most notably DNA damage that eventually leaves cells incapable of normal function. Such an analysis in a comparative and chronological fashion will be pursued so as to define molecular underpinnings at various stages of islet β-cell function: from the earliest stage prior to the establishment of islet cell hyperplasia, to hyperplasia with normal glycemia, and finally to dysfunctional hyperplasia with hyperglycemia. Four groups of mice will be used: Wild-type C57BL/6 on normal or high glucose diets; and AR-19Q on normal or high glucose diets. Dietary manipulation will also allow us to identify both the islet β-cell molecular responses (or the lack thereof in 19Q mice) to heightened glucose loads (glucose stress), and the molecular mechanisms associated with possible long-term decline in islet β-cell functionality, especially in the 19Q mice. The studies will entail in situ islet cells immunohistochemistry, and isolating islets to perform expression experiments, mass spectroscopy metabolomics and ultra-deep DNA sequencing. Islets will be isolated using a classical approach at 3, 6, and 18 months. All mice will have routine blood sugars drawn and GTTs (oral and intraperitoneal) performed with concomitant systemic insulin levels determined at the same time points.

Results.

The mouse model described in Example 1 was used to investigate the AR-19Q mice as a model for T2D. As described herein, theAR-19-Q mouse provides a suitable model for T2D.

As mentioned in Example 1, the AR-19Q mice first appear to have post-prandial hyperglycemia and eventually develop moderate fasting hyperglycemia, as seen from glucose tolerance tests and elevated blood glucose levels. On a standard diet, glucose impairment phenotypes are seen starting at 12 months and older. Elevated glucose levels are seen much earlier and precede glucose impairment. On a high fat diet, glucose impairment is seen much earlier starting for example after 3 months of HFD. Equally important are the pancreases of middle-aged 19Q mice (e.g. 10-14 months), which have significant islet hyperplasia (FIG. 5), with insulin resistance.

Example 3

Metabolic Syndrome Mouse Model and Type 2 Diabetes (T2D) and Islet Beta-Cell Failure Model Experiments Blood glucose levels are monitored on a biweekly basis on all 19Q mice with age matched controls, as well as circulating triglycerides and non-esterified fatty acids levels (monthly). Insulin resistance is formally established by analyzing in vivo insulin-induced phosphorylation of insulin receptor, IRS1 and Akt ($T^{308}$ and $S^{473}$) in liver, skeletal muscle and adipose tissue homogenates by western blot using corresponding commercially available antibodies (monthly). Furthermore, to assess obesity status mice fat pads, both epididymal and subcutaneous will be weighed, as well as brown adipose tissue vs. age-matched controls (monthly). In addition, liver and pancreas will be weighed and pancreas analysis for insulin and glucagon content by immunofluorescence and quantitatively using Metabolic Syndrome and Assay (MSA) kits (months 3, 6 12, 18, 24); white adipose tissue will be assessed for leptin and adiponectin contents (MSA) (months 3, 6 12, 18, 24). Circulating insulin leptin and adiponectin levels will be assessed at different ages using MSA kits while triglycerides and non-esterified fatty acids (NEFAs) will be determined (months 3, 6 12, 18, 24).

Circulating triglycerides, p-AKT and fat distribution analysis were determined.

Immunohistochemistry In Situ.

Islet cell quantitative immunochemistry techniques will be employed in situ in the 4 groups (C57BL/6 or 19Q mice, on normal or high glucose diets).

Insulin, glucagon and glucokinase content will be analyzed in conjunction with proteins supporting insulin promoter activity (PDX1, MafA)[11]. Other assays will include: i) oxidative damage analysis [cellular ROS detection kit e.g. MitoSOX staining of mitochondrial ROS]; ii) assessment of antioxidant/oxidative stress response [SOD1, Ape1/Ref-1 (or NM23-H1 and MPG), thioredoxin, thioredoxin reductase and protein disulfide isomerase]; iii) ER stress [ER stress antibody sampler kit]; iv) oxidative DNA damage markers (8-OxoG, γ-H2AX and protein carbonyls); vi) induction of DNA transcriptional repair (Xbp Xbd); and vii) standard apoptosis (annexin v/propidium iodide).

The baseline immunohistochemical data (normal islets, normal insulin/glucagon content of C57BL/6 animals on a normal diet) has been established.

With the C57BL/6 animals on a high glucose diet it is expected to observe potentially enhanced insulin content, but not any excessive oxidative damage nor DNA damage over time (1-24 months). On the other hand, it is expected that very young 19Q mice will have features similar to their C57BL/6 counterparts, but rapidly develop islet cell hyperplasia with exaggerated insulin production, and later on, oxidative stress, ER stress and DNA damage that may be accelerated in 19Q mice on a high glucose diet; in both latter cases, islet β-cell failure will be defined as inadequate insulin production.

Insulin Production.

Pancreatic islets will be isolated from all 4 groups (C57BL/6 or 19Q mice, on normal or high glucose diet) at time points 3, 6, and 18 months. After 2 days in culture, islets will be subjected to glucose-induced insulin secretion assays, using 5-16.7 mM glucose for 1 h. These experiments will be repeated in the presence of GLP-1 (10 nM). Insulin released in the medium will be normalized according to insulin content and both quantified using the appropriate MSA kit.

Gene Expression Studies.

Perusing the NCBI database hundreds of gene expression (GEO) datasets pertinent to diabetes have been identified, but fewer derived from pancreatic islets themselves. Though the latter are informative, many limitations were found with regards to experimental approaches in characterizing gene expression profiles: most or all are cross sectional analysis, many are sporadic humans cases (mostly cadavers after trauma), or from islet cell lines. In T2D rodent models there is a scarcity of expression data obtained in a direct comparative fashion (wild-type vs. rodent model), with alternative diets, coupled with time frames reflecting islet developmental/maturation studies, hyperplasia and eventual islet dysfunction. By combining studies of islet gene expression, further information will be known on genes and pathways that are responsible for islet hyperplasia and, more importantly, for islet failure during T2D development.

Thus, full gene expression data assessment will be performed on freshly isolated pancreatic islets from the 4 mouse groups [(normal or high glucose diet) at time points 3, 6, and 18 months], using the Affymetrix Mouse 2.0 ST microarray platform. This microarray platform will allow to assess over 26,000 annotated transcripts, including almost 6,000 non-coding RNAs (miRNAs and lncRNAs). Simultaneously, this array platform will also allow to study alternative RNA splicing. All 4 groups of animals will be assessed, but only 3 time points (3, 6, and 18 months) will be chosen to carry out the analysis. Approximately 3-5 million islet cells per mouse group and time point are expected to be isolated, which would be adequate to obtain sufficient input RNA for analysis.

After assessment of microarray studies, islet cell expression data will be supplemented with RNA Sequencing experiments of the same samples, but at selected time points (3, 6, and 18 months).

Example 4: Prostate Pre-Cancer/Cancer Mouse Model

In prostate cancer (PCa), years of investigative studies, supplemented by many recent and comprehensive genomic analyses, have helped enormously to garner a better understanding of PCa genetics. Although a fair number of PCa mutational landscape analyses have been disclosed, a more recent comprehensive analysis has become the new reference for PCa genetics[12]. This includes the analysis (whole exome, matched germline, transcriptome characterization) of 150 metastatic CaPs (localized, bone and soft tissue). The vast majority of previous PCa genetic analyses support the androgen receptor (AR) as a pivotal role-player in prostate cell tumor biology[13], but this recent analysis reports an even higher incidence of AR alterations in metastatic PCa (62.7%). Thus, the AR and its alterations play a fundamental role in both prostate cell and PCa biology, and therefore it is not unexpected that AR functionality is a real determinant of PCa progression and may play a crucial role in participating in the mutator phenotype.

A proper investigation of the mutator phenotype requires assessment of ongoing pathological status, (DNA alterations, specific gene analysis, and metabolic studies) in a continuum, with special emphasis on early histological abnormalities prior to established PCa, which is simply not feasible with clinical specimens (typically only cross sectional in nature), but feasible in an appropriate animal model.

The mouse AR shares over 90% homology with the human ortholog, but, interestingly, lacks the NTD CAG/polyQ tract; instead mice possess a mixed CAG/CAC-glutamine/histidine tract. Mice normally do not develop any element of prostatic hypertrophy or hyperplasia, and mouse models displaying prostate pathology are oncogenic transgenics where pathological time frames are not in keeping with humans[14]. As well, the transgenic oncogenes do not always represent the human condition, as many human CaPs do not have the same oncogenic expression.

A "humanized" knock-in mouse model containing the equivalent of the human polyQ tract was created, as described in Example 1. The AR-19Q mice phenotype can be best described as a mice counterpart to the Metabolic Syndrome seen in humans. Metabolic syndrome is a well-recognized association and possible risk factor for PCa.

AR-19Q Spontaneous Prostate Phenotype.

Figure 6C:
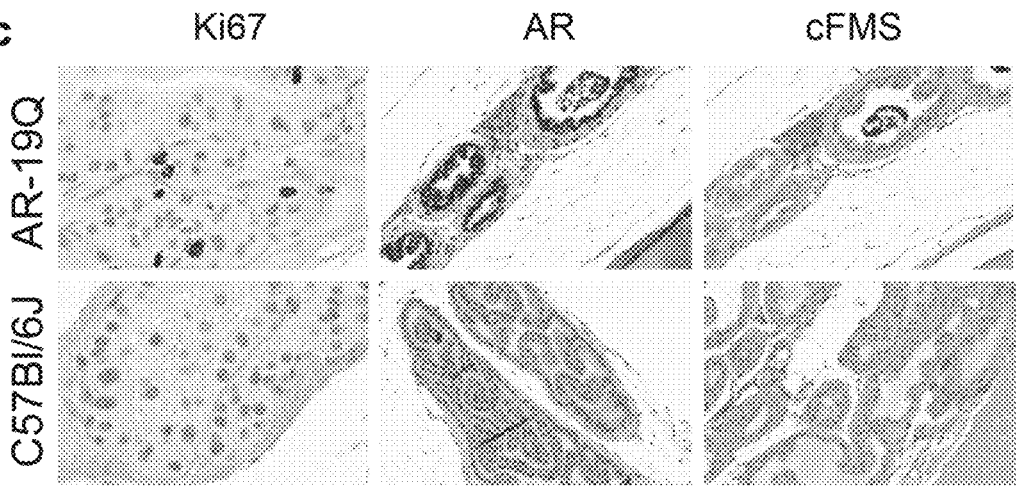

AR-19Q mice have shown a phenotype that presents high degree of benign prostatic hyperplasia (BPH)/hypertrophy with lymphocytic infiltration indicating an inflammatory process, prostatic intraepithelial neoplasia (PIN), and invasive adenocarcinoma. (FIG. 6A, B); Also, clear from the AR-19Q mice is the high lipid content. Inflammation is a key component in the initiation and development of PCa[15]. Immunohistochemical analyses have been done using antibodies against AR, cellular proliferation (Ki-67) and mouse macrophages (CFm-C20), and we found an increase in expression of these proteins in AR-19Q mice (FIG. 6C).

To analyze gene expression in the prostate samples, Qiagen RT$^2$ array platforms were employed, allowing to use real time RT-PCR to assess the gene expression profiles related to several pathways involved in PCa development at three different time points (18 months) [Platforms; Prostate Cancer, Metabolism, Mitochondrial Function/Energy Metabolism, AMPK Signaling, and Inflammation (FIG. 7A). The genes that show changes in expression between the AR-19Q mice vs. wild-type (VVT) including up-regulation of BCL2, EGR3, ERG, HK2 and HK3, CPT1B, and cytokines and interleukins. Similarly, the down-regulation of PTEN, APC, and GYS2 was observed. Gene expression abnormalities developing in a time dependent fashion, by analysis 6 vs. 12 vs. >18 prostate samples were also observed (FIG. 7B). Early up-regulation of cell cycle genes (CCNA1 and CDNK2A) at 6 and 12 months, expression of EGR3 and GPX3 at 12 months and continuing through to 18 months can be seen. Another group of genes found to be upregulated in the analysis included, H+-ATPase synthases, major components in ROS production in cells. Proteomic analysis also found the expression of ATP synthases were able to differentiate between BPH and PCa. Therefore, these changes in gene expression patterns in the AR-19Q-knock-in mouse are parallel observations that have been very well characterized in PCa, but here the observation of these gene expression patterns suggests initiation events occur prior to the full neoplasia phenotype.

Analysis of the inflammation RT$^2$ array show a strong inflammatory response in AR-19Q prostates (FIG. 7C and FIG. 7D). Intriguing data on inflammation as a potential driver for PCa development and progression has recently emerged[16]. The prostate gland is an immunocompetent organ, and along with epithelial and stromal cells, the prostate also contains a small number of immunocompetent cells (lymphocytes, macrophages and granulocytes). Stromal prostatic cells are able to secrete several cytokine, chemokine and growth factors, including IL-8, CXCL-10, and IL-6 not only in response to specific proinflammatory stimuli (i.e., tumor necrosis factor-α or the Toll-like receptor-4 agonist lipopolysaccharide), but also to metabolic insults and, in particular, to oxidized LDL and insulin. Moreover, chronic prostatic inflammation as observed in patients with MetS is associated with a milieu enriched in cytokines, inflammatory mediators and growth factors, which may lead to an uncontrolled proliferative response. In fact, increased circulating levels of MetS-related cytokines as well as leptin and adiponectin alterations have been preliminarily associated with PCa carcinogenesis[17].

Experiments

Metabolic profiles, ROS generation and quantify extent of DNA damage will be assessed in prostates of 19Q mice vs WT mice. An assay will be introduced to determine the DNA mutation rates of pertinent genes in order to gauge the mutator phenotype. Five mice of each group (VVT and AR-19Q) will be used at 5 different time points (2, 6, 12, 18, and 24 months) for the investigations described below.

RNA Sequencing—Gene Expression Profiling.

RNA sequencing will be used to define overall gene expression and transcript splicing profiles of prostate tissue isolated from each group. Whenever possible, if the prostates contain distinct areas of pathology and inflammation, these areas will be laser micro-dissected and analyzed independently. It is expected that the AR-19Q mice will have unique expression profiles associated with alterations in metabolic pathways, DNA repair and oxidative stress.

Immunohistochemistry for Protein Expression, ROS, and DNA Damage.

Specific protein quantification by immunohistochemistry will be completed: androgen receptor, glucose transporters, and hexokinases including glucokinase will be assessed. Mitochondrial ROS levels will be quantified and the antioxidant/oxidative stress response [SOD1, Ape1/Ref-1, thioredoxin (TRX), thioredoxin reductase (TRXR), and protein disulfide isomerase (PDI)], and induction of DNA repair proteins (Ape1/Ref-1, NM23-H1 and MPG), and oxidative damage markers (8-OxoG, γ-H2AX and protein carbonyls) will be assessed. Other analyses will be sought which will be dependent on data generated by metabolomics studies described herein. It is expected that there will be differences in a number of markers in 19Q mice vs. their WT counterparts, and within the 19Q mice themselves in areas of prostate hyperplasia.

Metabolomic Tumor Profiling.

The association of altered metabolism with the evolution of prostate pathology will be assessed by repeating the analysis at different time points: 2, 6, 12, 18, and 24 months in the AR-19Q mice.

The metabolomics analysis will assess metabolic fluxes through several important pathways, namely the glycolytic pathway, the pentose phosphate pathway, and oxidative phosphorylation. All of the major metabolites can be ascertained; glucose-6-P, glucose-1-P, 6-phosphogluconolactone, pyruvate, lactate, oxaloacetate, fructose-6-P, glyceraldehyde 3-P, ribose 5-P and many others. Glutathione levels ratios will be done to assess antioxidant status. Whenever possible, if the prostates contain distinct areas of pathology and inflammation, these areas will be laser micro-dissected and analyzed independently.

It will be determined whether the 19Q mice harbor abnormal glucose metabolism profiles and it is expected that the full metabolomics studies will give insight into the intracellular molecular abnormalities accounting for the glucose hypermetabolism phenotype. There exist many signature metabolomics profiles that are well characterized and cataloged, defined by key regulators of metabolism, e.g., PI3K, TP53, mTOR, AMPK. It is expected to see a time-dependent evolution of altered metabolomics, in hand with time-dependent prostatic pathology evolution.

Example 5: Non-Alcoholic Fatty Liver Disease, Non-Alcoholic Steatohepatitis and Hepatocellular Carcinoma Mouse Model The mouse model described in Example 1 was used to investigate the AR-19Q mice as a model for alcoholic fatty liver disease, non-alcoholic steatohepatitis and hepatocellular carcinoma and was found to be a suitable model for these diseases.

Figure 8B:
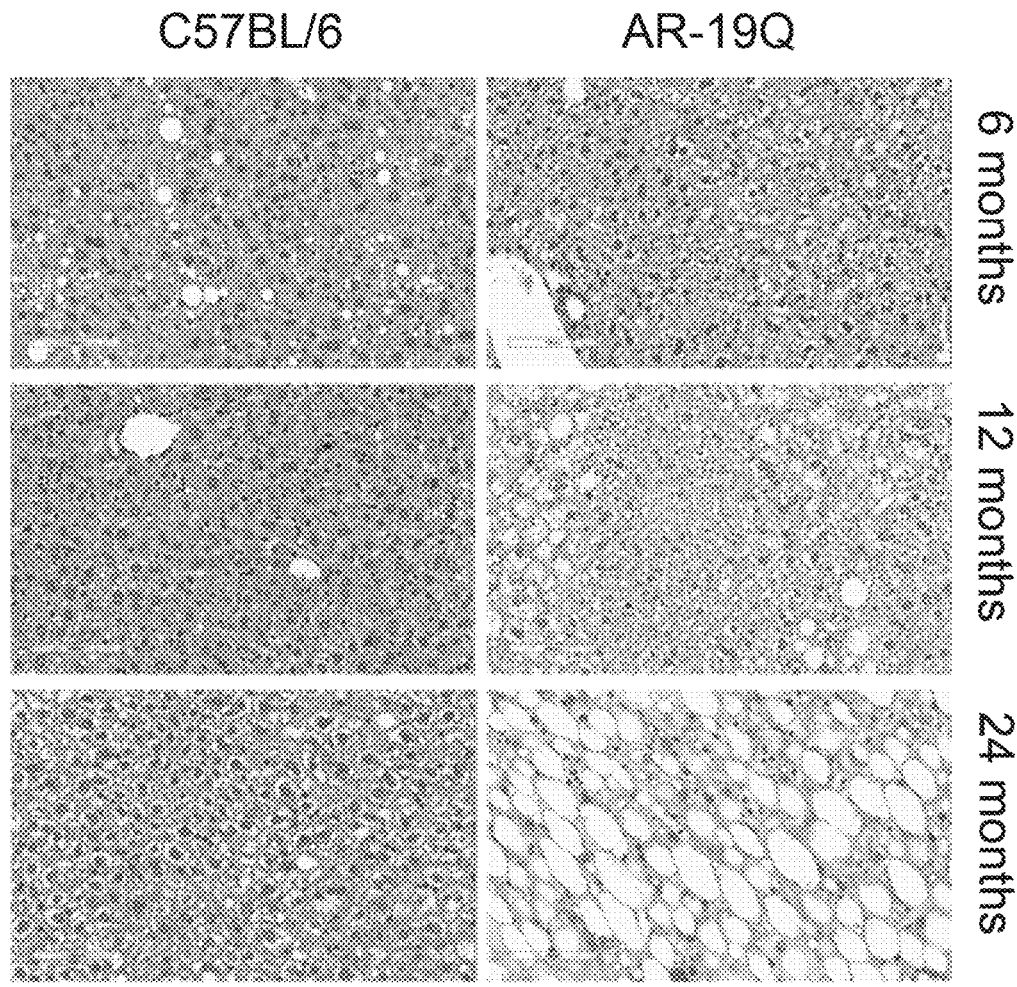
Figure 9A:
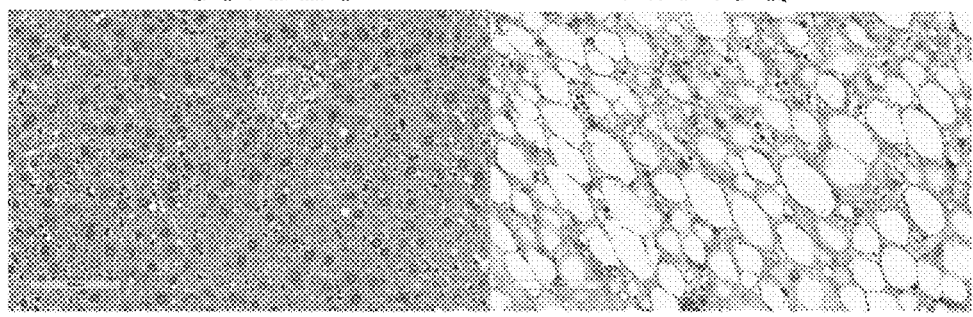
FIGS. 9A, 9B, 9C and 9D are images showing characterization of liver phenotype of AR-19Q mice.
Figure 9B:
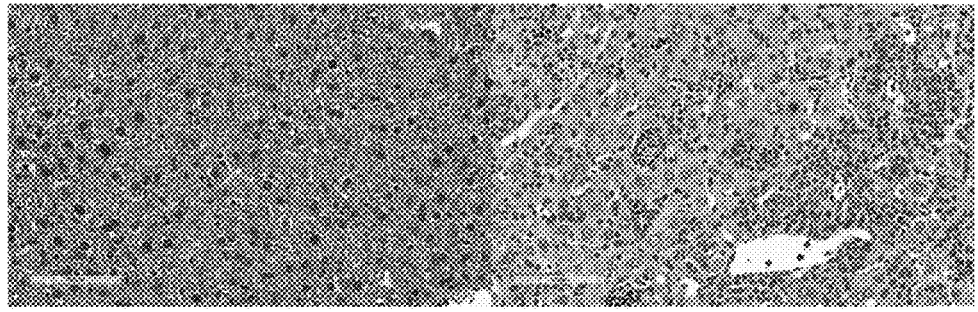
Figure 9C:
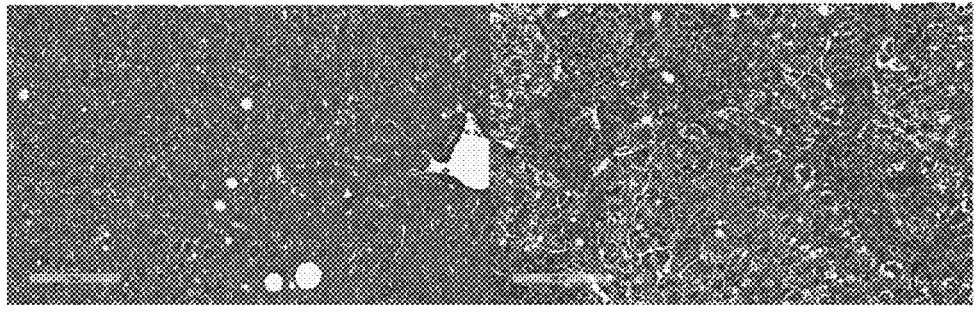
Figure 9D:
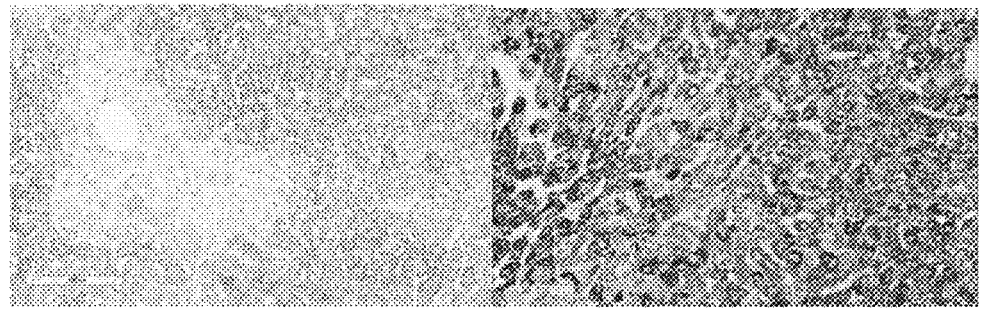

Blood tests showed a significant increase in alanine aminotransferase (ALT) levels, indicative of liver damage (FIG. 8A), and an intense fatty infiltration that with time develops into classical nonalcoholic steatohepatitis (NASH), hepatitis and subsequent NASH fibrosis (FIG. 8B). Nonalcoholic fatty liver disease (NAFLD) is caused by excessive uptake of lipids by the liver and, if left untreated, can result in chronic inflammation and eventually NASH (FIG. 9). Of AR-19Q mice, approximately 20% develop hepatocellular carcinoma (HCC). This progressive hepatic disease often accompanies obesity and has a complex set of causes that include insulin resistance, as well as signaling effects from adipose tissue, pancreatic islets, and skeletal muscle.

Preliminary Mouse Liver $RT^2$ Profiler PCR Arrays were completed for AR-19Q livers (FIG. 10) (profiles the expression of 84 key genes involved in the mechanisms of NAFLD/NASH and hepatic insulin resistance). We observed an upregulation of inflammatory/anti-inflammatory genes, Il-6, Il-10; tumor necrosis factor (Tnf); lipid/fatty acid metabolism notably, lipoprotein lipase (Lpl) leptin receptor, adiponectin receptor, PPAR gamma; and glucose metabolism, Akt, Mtor, PIK3a genes; Xbp1 mediator of cellular ER stress: Ptpn1 regulates phosphorylation of insulin receptor kinase and negatively regulates insulin signaling. Notable down-regulated genes include, Abca1, fatty acid synthase and glucose-6-phosphatase, as well as decreased expression of important glucose transporter genes, Slc2a2 and Slc2a4 encoding GLUT2 and GLUT4 respectively. Mlxipl, a basic HLH leucine zipper transcription factor that activates carbohydrate response element motifs in the promoters of triglyceride synthesis genes, is also decreased. Finally, Pdk4 is a kinase a regulator pyruvate dehydrogenase activity (pyruvate to acetyl-CoA). Decreased expression of Pdk4 will allow for significant increases in mitochondrial-mediated oxidative phosphorylation of glucose metabolites and ROS generation also found in limited clinical specimens. Pdk4 also has been linked to HCC. PPAR-γ-coactivator 1a is a transcription factor that coordinates genes required for healthy mitochondria biogenesis and is known to be deficient in NASH[18,19]. At least half of these are novel genes associated with NAFLD/NASH.

The androgen receptor (AR) Q19 mouse model described in Example 1, manifesting metabolic syndrome accompanied by the complete gamut of progressive liver diseases, (alcoholic fatty liver disease (NAFLD), non-alcoholic steatohepatitis (NASH) and hepatocellular carcinoma (HCC) alongside type 2 diabetes (T2D) can be used in the following studies to garner a better understanding of the molecular mechanisms responsible for liver diseases associated with metabolic syndrome and, as well, to serve as a therapeutic platform to assess treatment regimens.

Histopathology, immunochemistry studies of livers to assess metabolic stress and oxidative damage in the early spectrum of NAFLD to NASH to HCC.

gene expression analysis of the livers using RNA Seq to evaluate disease associated genes and pathways again at early stages of tissue pathology, coupled with Mass spectroscopy metabolomic profiling of livers to assess dysfunctional metabolism lending to NAFLD, NASH, and NASH cirrhosis.

Using recently acquired human clinical data, effectiveness of treatment regimens that are currently undergoing clinical trial using the AR-Q19 mouse as a pre-clinical test platform will be tested.

Animal Models.

Animal models are key to garner more information especially relevant to the early etiologies of HCC. Mouse models have been employed for HCC studies and include xenograft and orthotropic models, chemical models and allograft models. Genetically engineered models include transgenes of Hepatitis B (or C), c-MYC, TGFα or SV40-T Antigen and a very recent mitochondrial prohibitin gene knockout mouse (MITO-mouse)[20]. While these mouse models are appropriate in their respective areas they are not representative of HCC in the background of common metabolic syndrome liver diseases and are not "best-fit models". As a result, a complete understanding of the molecular pathological mechanisms responsible for NASH and NASH related diseases including HCC have been severely hampered by inadequate mouse models, where either a significant gene alterations or highly manipulated diets are required to capitulate phenotypes that are not in-keeping with the manifestation of the human condition.

The AR-19Q mouse model offers a unique opportunity to investigate the molecular pathological etiologies of several important livers diseases associated with metabolic syndrome and T2D. Thus, investigations can be had in a very systematic fashion and will give new insight on the pathophysiology of each related disease entity and potential future drug targets. Omics are very inclusive in nature and are excellent choices to pursue systematic studies. The mouse model is equally attractive to be employed as a therapeutic platform and is an important as the investigative model. Here recent data will be used to pursue new and novel therapeutic options aimed at early disease NAFLD which if successful should prevent evolution to NASH, cirrhosis and HCC. The anatomy and histology of the fatty acid deposition in the AR Q19 mouse appears to be quite identical to the human counterpart (macro vs micro steatohepatomegaly).

High Fat Diet.

AR-19Q mouse a high fat diet (HFD) that resulted in an accelerated weight gain vs. the normal chow 19Q mice in 3 months (FIG. 11). Ultrasound showed significantly larger livers, as well as fatty liver. Higher glucose and liver ALT enzyme were also observed in HFD AR-19Q fed mice.

The AR-19Q model developed in is physiologically relevant to metabolic syndrome and related liver disorders, displaying liver pathologies in continuum from early fatty liver NAFLD to NASH to HCC, without significant genetic alterations or dietary manipulations. Thus, it is unique and is a clear departure from other models mimicking the human condition and represents a major advancement in available working models for HCC. This model will allow us to assess ongoing genetic and metabolic changes in the evolution of liver disorders from NASH to HCC in a chronological fashion and will certainly help establish initial pathways and events related to the initiation of several stages of liver diseases. Critically the mouse model is equally qualified to be used as a competent therapeutic platform allowing the assessment of treatment regimens to defer disease pathologies.

Preliminary data strongly suggests that intermediary metabolism, provoked by either insulin resistance and/or hyperglycemia itself with inflammation initiates liver disorders commonly seen in metabolic syndrome. It is believed that heightened metabolic fluxes leads to excessive mitochondrial ROS and lipid synthesis, cell stress, and subsequent cellular damage with associated inflammatory involvement; excessive oxidative damage lends to continuing DNA alterations eventually allowing for a neoplastic HCC transformation. To investigate the link between abnormal metabolism, oxidative damage and inflammatory alterations studies in a comparative and temporal fashion, to define the molecular underpinnings at various stages of disease progression, from normal liver to fatty liver to hepatitis to cirrhosis and HCC will be pursued.

It has been noted, that mice fed HFD for 3 months develop a liver phenotype which is not reversed by switching to SFD. Although mice switched to SFD for 3 months, lost weight the liver phenotype was not altered or reversed.

These studies will be done under different conditions that already have been shown clearly to have an important effect on the phenotype i.e diet and hormonal status. For Specific Aims 1-3 the cohorts that will be studied are as follows: AR Q19 and WT mice normal diet (SFD), AR Q19 and WT mice fed high fat diet (HFD), and AR Q19 castrated and WT mice castrated normal diet (SFD). The former studies help delineate and define the critical molecular pathological mechanisms underlying the several stages of liver related diseases associated with metabolic syndrome/T2D and the latter castrated mice studies will help discover the molecular pathways by which the AR-19Q vs WT utilize to confer disease etiology. Wth respect to mice harboring HCC tumors, adjacent non-HCC-matched tissue will be included. The studies will be comparative and sequential in nature; normal vs. NASH vs. HCC. For Specific Aim 3 (therapeutic intervention) only AR-19Q vs WT mice normal diet will be used. Early diseased NAFLD mice will be chosen, as successful treatment of NAFLD can be considered to be a preventative measure avoiding later disease pathologies.

Experiments

Metabolic Syndrome (10 Mice/Cohort).

A liver Metabolic Syndrome and Assay (MSA) kits (months 3, 6 12, 18, 24) will be used and changes in leptin and adiponectin contents (MSA) in white adipose tissue (months 3, 6 12, 18, 24) will be assessed. Circulating insulin leptin and adiponectin levels will be assessed at different ages using MSA kits while triglycerides, cholesterol profiles and non-esterified fatty acids (NEFAs) will be determined (months 3, 6 12, 18, 24). Finally, a group of control and 19Q mice assessed for their metabolic activity and food intake in metabolic cages.

For liver immunohistochemistry (months 3, 6 12, 18, 24), assays will include: 0 oxidative damage analysis [cellular ROS detection kit e.g. MitoSOX staining of mitochondrial ROS]; ii) assessment of antioxidant/oxidative stress response [SOD1, Ape1/Ref-1 (or NM23-H1 and MPG), thioredoxin, thioredoxin reductase and protein disulfide isomerase]; iii) ER stress [ER stress antibody sampler kit]; iv) oxidative DNA damage markers (8-OxoG, γ-H2AX and protein carbonyls); vi) induction of DNA transcriptional repair systems (XbpXbd); and vii) standard apoptosis (annexin v/propidium iodide).

Liver Studies: OMIC Studies. (5 Mice/Cohort).

The AR-19Q Mouse model offers a unique opportunity to study the molecular mechanism and evolution of significant liver diseases associated with the metabolic syndrome. The preliminary RT$^2$ data, though providing limited profiling, suggests significant alterations in carbohydrate, lipid and mitochondrial oxidative phosphorylation; a full expression study is warranted and will be pursued with emphasis placed on metabolism and inflammation pathways. Altered metabolism is clearly one the major properties of early to late stages of liver diseases NAFLD and NASH. Most cancers also have clear departures in metabolism that plays a pivotal role in cancer evolution. As such the AR Q19 mouse will allow us to characterize metabolic properties of each in a systematic fashion. AR Q19 castrated vs WT mice castrated normal diet cohort is a critical group as it will help delineate and define the critical molecular pathological mechanisms by which the AR Q19 AR vs WT AR utilize to confer disease etiology.

OMIC Studies: Gene Expression RNA Seq.

RNA Sequencing has a greater ability, and outperforms microarrays, in quantifying and identifying expressed genes (plus alternative RNA splicing), RNAs of low abundance and a greater number of non-coding RNAs including miRNAs. miRNAs are critical non-coding RNAs that can master-regulate multiple expression of many genes simultaneously. The preliminary RT$^2$ data, though providing limited profiling, suggests significant alterations in carbohydrate, lipid and mitochondrial oxidative phosphorylation; a full expression study is warranted with emphasis placed on metabolism and inflammation pathways. Analysis NAFLD, NASH, adjacent HCC and HCC will be performed at months 3, 6 12, 18. RNA Seq will be completed at facilities within the McGill Genome Center.

OMIC Studies: Metabolomics (Fasting Vs 1 hr Post Prandial).

The Metabolomics Center ultra-high-pressure liquid chromatography quadrupole time of fight mass spectrometry to conduct metabolomics. Liquid chromatography is preferred as it gives greater metabolite coverage and higher mass metabolites. The chemical analysis will be conducted in different ways, to provide good coverage across the metabolome: C18 reverse phase for non-polar components, and hydrophobic interaction liquid chromatography (HILIC) for polar components. A total of 4 orthogonal data sets will be obtained. In addition, MS/MS analysis will also be performed on each respective mode for subsequent metabolite identification and matching with known databases such as the Human Metabolite Database. The data sets will then be processed via Agilent qualitative analysis and mass profiler professional for peak detection and alignment for peak table generation for the identification of dysregulated metabolites and pathways in the various stages of liver pathologies.

Fresh liver cell preparations from the 4 mouse groups, isolated time points, from fasting and 1 hr post prandial mice will be used. The tissue will be collected and flash frozen, awaiting cell extraction using an acetonitrile extraction protocol (10 replicates). The metabolomics analysis will assess metabolic fluxes through several important pathways, namely the glycolytic and lipid pathways, the pentose phosphate pathway, and oxidative phosphorylation. All the major metabolites can be ascertained: glucose-6-P, glucose-1-P, 6-phosphogluconolactone, pyruvate, lactate, oxaloacetate, fructose-6-P, glyceraldehyde 3-P, ribose 5-P and many others. Glutathione levels and NADP/NADPH ratios will be done to assess antioxidant status.

Only a few metabolomic studies[21,22] have been completed but are of limited scope: cross sectional pathologies including HCC.

Histochemistry and Immunohistochemistry.

Tissue Microarrays (TMA) will be prepared for liver analysis from the most representative areas of paraffin embedded livers.

Liver histochemistry will comprise of standard liver histochemistry, which will include assessment of steatosis (micro vs macro-vesicular), cellular ballooning, hepatocytolysis, later stage perisinusoidal fibrosis to periportal fibrosis, Mallory bodies and important inflammatory (neutrophils, eosinophils, lymphocytes, Kupffer cells) infiltrates (intralobular and periportal). Attention will be paid to pathological findings according to zonal liver architecture. Standard H&E staining and Masson's trichrome (fibrosis) will be completed supplemented by Sirius red (collagen proportional area) using digital imaging. The NASH Clinical Research Network criteria will be used as much as possible in staging disease.

For liver immunohistochemistry, adiponectin (stimulates anti-inflammatory cytokines), insulin receptor, TNFα will be assessed, as well as a panel of extensive CD markers to identify and characterize classes and subclasses of inflammatory cellular infiltrates [B lymphocytes, T lymphocytes, macrophages, To assess more specifically cellular stress and oxidative damage (months 6, 9, 12, and 15), assays will include: 1) oxidative damage analysis [cellular ROS detection kit e.g. MitoSOX staining of mitochondrial ROS] and iNOS (nitric oxide synthase associated with insulin resistance inflammatory mediators) 2) assessment of antioxidant/oxidative stress response [SOD1, Ape1/Ref-1 (or NM23-H1 and MPG), thioredoxin, thioredoxin reductase and protein disulfide isomerase]; 3) ER stress [ER stress antibody sampler kit]; 4) oxidative DNA damage markers (8-OxoG, γ-H2AX and protein carbonyls); 5) induction of DNA transcriptional repair systems (XbpXbd); and 6) standard apoptosis (annexin v/propidium iodide).

Liver Disease Etiology.

Metabolism. (5 Mice/Cohort).

Human NAFLD liver samples were obtained and used to perform extensive omics, histochemistry, immunohistochemistry and spatially resolved mass spectroscopy imaging (MALDI). Macro steatosis contained higher proportions of saturated triglycerides compared to micro steatosis. Laser capture microdissection transcriptomics illustrated several genes (EIF2S1, MBTPS1 ATF6) higher in macro vs micro steatosis. Thus, macro steatosis correlates with lipogenesis, increased ER stress and CLDs containing higher saturated lipids that can be converted to unsaturated lipids augmenting ER stress. Overall fatty acid production results in the generation of reactive oxygen species (ROS) damaging components involved in the mitochondrial electron transport chain, accruing even more ROS production. ROS also creates ER stress directly by forming adducts with both lipids and proteins. This triggers several stress signaling pathways including the UPR and autophagy processes.

It will be first validated that the AR Q19 mice follow a similar hepatic pattern of increased ER stress (e.g. EIF2S1 and MBTPS1), lipogenesis (i.e. nuclear localization of SREBP-1c and SREBP-2 by immunohistochemistry) and macro steatosis (as determined by histochemistry) as outlined by human samples. These studies will be used together with histological features as endpoints of early disease and disease progression in drug intervention studies (see below). During these studies, AR Q19 mice will be followed beyond NAFLD and ER stress progression and correlate with NAFLD, NASH, cirrhosis and HCC (months 3, 6, 9, 18) will be examined. The time schedule was chosen as an ideal time period allowing for early intervention and possible prevention of later disease phenotype.

Dietary manipulations will first include palmitic acid[23] (30 µmol/mouse in 50 µL castor oil intraperitoneal (IP) injection daily vs vehicle alone starting at 6 months for 3 months), a saturated fatty acid known to increase ER stress and therefore should provoke macro steatosis and disease progression; The second dietary manipulation will include an inhibitor of stearoyl-CoA deasturase-1(N-(2-hydroxy-2-phenylethyl)-6-[4-(2-methylbenzoyl)piperidin-1-yl]pyridazine-3-carboxamide)[24] already proven to be effective in inhibiting the conversion saturated fats to unsaturated fats (30 mg/kg/d oral administration starting at 6 months for 3 months duration). Again, it will be examined whether this ameliorates disease progression (months 3, 6, 9, 18) as described above.

Removal of ROS and other reactive species (e.g. NOS) through scavengers should mitigate damage caused on organelles, proteins, lipids and alleviate ER stress. Thus AR Q19 mice will be treated with MnTBAP (a mimic of superoxide dismutase converting ROS to hydrogen peroxide)[25] 20 mg/kg in PBS IP daily vs vehicle starting at 6 months for 3 months). To assess ROS, thiobrabituric acid-reactive substances and mitochondrial glutathione levels will be monitored (months 3 6, 9, 18). Again, treatments will be correlated with disease status by routine histochemistry of liver sections and endpoints described above and assess roles in liver pathologies beyond NALFD ie NASH, cirrhosis and HCC. (months 3, 6, 9, 18).

Therapeutic Intervention Study.

Historically, molecules proven to be the most effective against NASH have been thiazolidinediones (TZDs), particularly Pioglitazone, a PPARγ agonist having demonstrated significant results in clinical studies (NCT00062764) with a 30 mg/day doses. Unfortunately, at this dosage, side effects of pioglitazone are noteworthy: weight gain, edema, bone fractures and increased risk of bladder cancer. For this reason, the PPARγ agonists could not be considered as a therapeutic option for the treatment of NASH. Therefore, other compounds are being pursued and upon a review of the literature and currently ongoing clinical trials, two compounds to test with the AR19Q mouse were selected and ranked.

Elafibranor/GFT505 (Genfit).

In November 2015, GENFIT announced the design of the global Phase 3 clinical trial RESOLVE-IT (NCT02704403) to evaluate the benefits of Elafibranor treatment on NASH patients. RESOLVE-IT is a randomized pivotal trial, double-blind, placebo-controlled (2:1), conducted in approximately 2000 patients, at 250 centers worldwide. The patient population are NASH patients with (NAS4) with F2 or F3 fibrosis given Elafibranor 120 mg or placebo, administered once daily. Elafibranor, initially developed to target T2D, is a new dual activator of the nuclear receptors PPARα/O having multiple properties: modulates plasma glucose and lipid levels, have prominent anti-fibrotic and anti-inflammatory affects. From their Phase IIb trials (NCT01694849), the following claims were made: 1. Improvement in markers of hepatic dysfunction, including liver enzymes: ALT, AST, GGT, and ALP; 2. Improved insulin sensitivity and glucose homeostasis; 3. Beneficial effects on plasma lipids, with a reduction in triglyceride and LDL-C and increased HDL-C levels; 4. Anti-inflammatory effects; 5. Beneficial effects on histological parameters NASH (steatosis, inflammation, fibrosis) in animal models (anti-fibrotic activities); 6. A good safety profile with no unwanted side effects in clinical trials (reinforced profile in toxicology studies with up to two-year carcinogenicity studies).

The study included patients with NASH/NAFLD scores of 3 to 8 inclusive. This inclusion, which had been validated by the FDA, represented a small group of patients (~15%). The study advocated to the patients a healthy eating and exercise lifestyle. Thus, the statistical impact of patients with a NAS score <4, prevented Elafibranor from having statistically significant results across the entire study population. The mere withdrawal of NAS <4 patients immediately altered the results of study:t a statistically acceptable positive result (22.4% vs 12.7%; Elafibranor vs placebo, p=0.046, RR=1.9).

MSDC-0602K (Octeta).

To target NASH, Ocetata Therapeutics have developed a different strategy by targeting mTOT (a mitochondrial target of thiazolidinediones), which would defer the activation of PPARγ. By modulating mTOR one can increase insulin sensitivity significantly without side effects PPARγ agonists. Regulating NASH via insulin sensitizer has been a promising pathway. A clinical Phase IIa was conducted for 28 days weeks comparing the effect of the MSDC-0602K (100 mg, 250 mg) to the Pioglitazone (45 mg). Their results show MSCD-0602K was equivalent to Pioglitazone on overall glucose control, adiponectin levels, and extrapolated a potential positive effect of MSCD-0602K on NASH prompting a 12 month Phase IIb trial (NCT02784444) which is currently underway, assessing tolerability and efficacy, with the goal of hepatic histological improvement in NASH with a NAS decrease in at least 2 points with no concurrent worsening of fibrosis. Also, the reduction in NAS must include either a 1 point reduction in ballooning or inflammation.

Obeticholic Acid/Ocaliva (Intercept).

Ocaliva is approved for primary biliary cirrhosis. Intercept is currently recruiting NASH patients for a phase 3 trial: "Randomized Global Phase 3 Study to Evaluate the Impact on NASH with Fibrosis of Obeticholic Acid Treatment (REGENERATE)": NCT02548351. In a Phase 2 trial, NCT01265498 (Farnesoid X nuclear receptor ligand obeticholic acid for non-cirrhotic, non-alcoholic steatohepatitis (FLINT): a multi-centered, randomized, placebo-controlled trial results), 141 patients were randomly assigned to receive obeticholic acid and 142 to placebo. 50 (45%) of 110 patients in the obeticholic acid group who were meant to have biopsies at baseline and 72 weeks had improved liver histology compared with 23 (21%) of 109 such patients in the placebo group (relative risk 2.2, 95% CI 1.4 to 3.3; p=0·0002)[26].

Selonsertib/ASK1 Inhibitor (Gilead Science).

Selonsertib is currently undergoing clinical trials, with Gilead Science recently publishing their Phase 2 study[27]. After 24 weeks of treatment, the proportion of patients with a one or more stage reduction in fibrosis in the 18-mg selonsertib group was 13 of 30 (43%; 95% confidence interval, 26-63); in the 6-mg selonsertib group, 8 of 27 (30%; 95% confidence interval, 14-50); and in the simtuzumab-alone group, 2 of 10 (20%; 95% confidence interval, 3-56). Improvement in fibrosis was associated with reductions in liver stiffness on magnetic resonance elastography, collagen content and lobular inflammation on liver biopsy, as well as improvements in serum biomarkers of apoptosis and necrosis. Phase 3 studies of selonsertib in patients with NASH and bridging fibrosis (STELLAR-3; NCT03053050) and compensated cirrhosis (STELLAR-4; NCT03053063) are planned for.

Drug Intervention Studies: AR-19Q Animal Studies with Elafibranor, MSDC-0602K, Selonsertib, and Obeticholic Acid.

AR Q19 mice on normal diet or high fat diet will receive either Elafibranor[28] or MSDC-0602K[29] (30 mg/kg/day and 50 mg/kg/day orally) or obeticholic acid (10 mg/kg/day and 20 mg/kg/day orally) or Selonsertib (3 mg/kg/day and 6 mg/kg/day) vs. a vehicle control (1% methyl cellulose), for 6 and 12 weeks. The study will begin at 12 months for SFD and 6 months for HFD, where it is believed that mice will be displaying NAS>4 an appropriate stage for treatment. The mice will be evaluated for the following criteria and expected improve outcomes for each compound. For these experiments 10 mice/cohort will be used Biochemistry Profiling.

Blood glucose will be monitored weekly, with liver enzyme profiling (Abaxis—Mammalian Liver Profile) and liver ultrasounds to assess size and content will performed every two weeks. Weights are performed weekly.

Histopathology and Immunohistochemistry.

Following the 6 week period, mice will be sacrificed and dissected, with histopathology performed on the livers. Liver histopathology will again comprise of standard liver histopathology, assessing degree/improvements with respect to: steatosis (micro vs macro-vesicular), cellular ballooning, hepatocytolysis, later stage perisinusoidal fibrosis to periportal fibrosis, Mallory bodies and important inflammatory (neutrophils, eosinophils, lymphocytes, Kupffer cells) infiltrates (intralobular and periportal). Attention will be paid to pathological findings according to zonal liver architecture. Degree of fibrosis will be measured by Masson's trichrome and supplemented by Sirius red (collagen proportional area) using the aforementioned digital imaging.

For liver immunohistochemistry, adiponectin (stimulates anti-inflammatory cytokines), insulin receptor, TNFα will be assessed, with the panel of CD markers to identify and characterize classes and subclasses of inflammatory cellular infiltrates [B lymphocytes, T lymphocytes, macrophages].

Example 6

Females Fed HFD Develop Metabolic Disease

Female AR-19Q mice do not develop the metabolic phenotype observed in male mice when they are fed a standard fat diet (SFD). Female AR-19Q mice were fed with high fat diet (HFD), starting at the age of 1.5 months and for a duration of 6 months. Food and water was ad libitum and the mice were kept in standard cages and in a light/dark cycle of 12 hours.

At the end of the 6 months the mice were euthanized, and necropsies performed to collect organs for histopathological analyses: standard Hematoxylin and Eosin staining, and Trichrome and Sirius Red staining for fibrosis, in the liver. Also, blood was collected by cardiac puncture to perform biochemical analyses: Glucose level, Alanine Amino Transferase (ALT), and Triglycerides level (TG).

Female mice fed with HFD presented with an obese phenotype as early as 3 months after starting the HFD and they had a progressive gain of weight comparable to that obtained with male AR-19Q fed HFD. Female AR-19Q mice fed HFD present with a slight hyperglycemia when compared with those mice fed SFD and they present with a significant increased ALT, indicating that they have liver damage. The liver damage is seen after 3 months on HFD.

An approximate 8-fold and statistically significant increase was observed in white adipose tissue (WAT) weight in female AR-19Q fed HFD which is one of the characteristic of metabolic syndrome. The liver of the female AR-19Q mice fed HFD present a difference in weight (approaching significance), indicative of hepatomegaly and liver steatosis (FIG. 11F).

The biochemical profile showed that when females were fed SFD the females did not have increase in their biochemical profile as did males (Table 5). On the other hand, when mice were fed HFD the values of the weight increased, and biochemical profile were very similar.

TABLE 5

| | WEIGHT (g) | GLU (mmol/L) | ALT (IU/L) | AST (IU/L) | TG (mg/dl) |
|---|---|---|---|---|---|
| Biochemical Profile. AR-19Q. 6 months on SFD | | | | | |
| AR-19Q FEMALE | 24 | 7.8 | 29 | 17 | 60 |
| AR-19Q MALE | 33 | 9.5 | 36 | 93 | 139 |
| Biochemical Profile. AR-19Q. 6 months on HFD | | | | | |
| AR-19Q FEMALE | 52.3 | 9.9 | 126.8 | 55 | 84 |
| AR-19Q MALE | 56.4 | 10.9 | 112 | 90.2 | 128 |

Necropsies were performed after 6 months on HFD for male and female mice and their organs were weighed. Although the total weight of each organ of the mice is comparable, it is observed that the female mice present with a higher WAT, with infiltration through all the organs.

The liver histopathologic analysis, shows that the female mice fed HFD for 6 months develop NASH grade 3: steatosis 66%, ballooning, stage 1 fibrosis and lobular inflammation with the presence of foci of leukocyte infiltration. This phenotype is like the one observed with male AR-19Q.

Example 7

Ovarian Disease in Female Mice on HFD

Female AR-19Q mice and wild type mice were fed a HFD for 3 months, starting at starting at the age of 1.5 months. Food and water was ad libitum and the mice were kept in standard cages and in a light/dark cycle of 12 hours.

Female mice on HFD also develop ovarian disease.

Ovaries were dissected and stained by H/E. As shown in FIG. 12, the AR-19Q knock-in female mice on HFD presented ovarian disease phenotype with strong fat infiltration. Ovaries dissected from female AR-19Q mice on a high-fat diet stained by H/E are shown in FIG. 12. Ovaries display significant fat infiltration compared to their wild-type counterparts. Moreover, follicle cells surrounding the oocyte also show significant fat ballooning.

These female mice, on HFD, also display an accompanying infertility phenotype, and cannot be mated males to produce offspring.

REFERENCES

1. Lieberman A P, Robins D M. The androgen receptor's CAG/glutamine tract in mouse models of neurological disease and cancer. J Alzheimers Dis 2008; 14:247-55.
2. Mousavi G. Generating vectors for production of transgenic mouse models to investigate the role of the androgen receptor and its CAG repeat in human prostate cancer [Thesis (M Sc)]; 2005.
3. Ausubel F M. Short protocols in molecular biology: a compendium of methods from Current protocols in molecular biology. 4th ed. New York: Wiley; 1999.

4. Hogan B, Costantini F, Lacy E. Manipulating the mouse embryo: a laboratory manual. Cold Spring Harbor, N.Y.: Cold Spring Harbor Laboratory; 1986.
5. Hogan B. Manipulating the mouse embryo: a laboratory manual. 2nd ed. Plainview, N.Y.: Cold Spring Harbor Laboratory Press; 1994.
6. Mhatre A N, Trifiro M A, Kaufman M, et al. Reduced transcriptional regulatory competence of the androgen receptor in X-linked spinal and bulbar muscular atrophy. Nature genetics 1993; 5:184-8.
7. Southwell J, Chowdhury S F, Gottlieb B, et al. An investigation into CAG repeat length variation and N/C terminal interactions in the T877A mutant androgen receptor found in prostate cancer. The Journal of steroid biochemistry and molecular biology 2008; 111:138-46.
8. Alvarado C, Beitel L K, Sircar K, Aprikian A, Trifiro M, Gottlieb B. Somatic mosaicism and cancer: a microgenetic examination into the role of the androgen receptor gene in prostate cancer. Cancer research 2005; 65:8514-8.
9. Sircar K, Gottlieb B, Alvarado C, et al. Androgen receptor CAG repeat length contraction in diseased and non-diseased prostatic tissues. Prostate Cancer Prostatic Dis 2007; 10:360-8.
10. Gottlieb B, Alvarado C, Wang C, et al. Making sense of intratumor genetic heterogeneity: altered frequency of androgen receptor CAG repeat length variants in breast cancer tissues. Human mutation 2013; 34:610-8.
13. Nickerson M L, Im K M, Misner K J, et al. Somatic alterations contributing to metastasis of a castration-resistant prostate cancer. Human mutation 2013; 34:1231-41.
14. Wu X, Gong S, Roy-Burman P, Lee P, Culig Z. Current mouse and cell models in prostate cancer research. Endocrine-related cancer 2013; 20:R155-70.
15. Nelson W G, De Marzo A M, DeWeese T L, Isaacs W B. The role of inflammation in the pathogenesis of prostate cancer. The Journal of urology 2004; 172:S6-11; discussion S-2.
16. Vignozzi L, Maggi M. Prostate cancer: intriguing data on inflammation and prostate cancer. Nat Rev Urol 2014; 11:369-70.
17. De Nunzio C, Aronson W, Freedland S J, Giovannucci E, Parsons J K. The correlation between metabolic syndrome and prostatic diseases. European urology 2012; 61:560-70.
18. Hwang B, Jeoung N H, Harris R A. Pyruvate dehydrogenase kinase isoenzyme 4 (PDHK4) deficiency attenuates the long-term negative effects of a high-saturated fat diet. The Biochemical journal 2009; 423:243-52.
19. Hwang B, Wu P, Harris R A. Additive effects of clofibric acid and pyruvate dehydrogenase kinase isoenzyme 4 (PDK4) deficiency on hepatic steatosis in mice fed a high saturated fat diet. The FEBS journal 2012; 279:1883-93.
20. Ande S R, Nguyen K H, Gregoire Nyomba B L, Mishra S. Prohibitin-induced, obesity-associated insulin resistance and accompanying low-grade inflammation causes NASH and HCC. Sci Rep 2016; 6:23608.
21. Nakatsu D, Horiuchi Y, Kano F, et al. L-cysteine reversibly inhibits glucose-induced biphasic insulin secretion and ATP production by inactivating PKM2. Proceedings of the National Academy of Sciences of the United States of America 2015; 112:E1067-76.
22. Pillai R, Huypens P, Huang M, et al. Aryl hydrocarbon receptor nuclear translocator/hypoxia-inducible factor-1{beta} plays a critical role in maintaining glucose-stimulated anaplerosis and insulin release from pancreatic {beta}-cells. The Journal of biological chemistry 2011; 286:1014-24.
23. Pardo V, Gonzalez-Rodriguez A, Muntane J, Kozma S C, Valverde A M. Role of hepatocyte S6K1 in palmitic acid-induced endoplasmic reticulum stress, lipotoxicity, insulin resistance and in oleic acid-induced protection. Food and chemical toxicology: an international journal published for the British Industrial Biological Research Association 2015; 80:298-309.
24. Kurikawa N, Takagi T, Wakimoto S, et al. A novel inhibitor of stearoyl-CoA desaturase-1 attenuates hepatic lipid accumulation, liver injury and inflammation in model of nonalcoholic steatohepatitis. Biol Pharm Bull 2013; 36:259-67.
25. Pires K M, Ilkun O, Valente M, Boudina S. Treatment with a SOD mimetic reduces visceral adiposity, adipocyte death, and adipose tissue inflammation in high fat-fed mice. Obesity (Silver Spring) 2014; 22:178-87.
26. Hossain D, Bostwick D G. Significance of the TMPRSS2:ERG gene fusion in prostate cancer. BJU international 2013; 111:834-5.
27. Loomba R, Lawitz E, Mantry P S, et al. The ASK1 inhibitor selonsertib in patients with nonalcoholic steatohepatitis: A randomized, phase 2 trial. Hepatology 2017.
28. Staels B, Rubenstrunk A, Noel B, et al. Hepatoprotective effects of the dual peroxisome proliferator-activated receptor alpha/delta agonist, GFT505, in rodent models of nonalcoholic fatty liver disease/nonalcoholic steatohepatitis. Hepatology 2013; 58:1941-52.
29. Fukunaga T, Zou W, Rohatgi N, Colca J R, Teitelbaum S L. An insulin-sensitizing thiazolidinedione, which minimally activates PPARgamma, does not cause bone loss. J Bone Miner Res 2015; 30:481-8.

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Specifically, the sequences associated with each accession numbers provided herein including for example accession numbers and/or biomarker sequences (e.g. protein and/or nucleic acid) provided in the Tables or elsewhere, are incorporated by reference in its entirely.

The invention claimed is:

1. A construct comprising a) a nucleotide sequence comprising a 5' androgen receptor (AR) arm comprising a portion of exon 1 of mouse AR gene, and b) an exogenous polyglutamime (polyQ) tract encoding sequence, and c) optionally a selectable marker,
   wherein the exogenous polyQ tract encoding sequence replaces an endogenous polyglutamine/histidine (polyQ/H) tract encoding sequence corresponding to amino acids 9 to 19 of the endogenous polyglutamine/histidine (polyQ/H) tract in the portion of exon 1 of mouse AR gene,
   wherein only the endogenous poly Q/H encoding tract is replaced and wherein the exogenous polyQ tract encoding sequence encodes 16 to 23 glutamine residues.

2. The construct of claim 1, wherein the exogenous polyQ tract encoding sequence is 16 to 23 contiguous CAG repeats.

3. A recombinant cell, fertilized egg or tissue comprising a recombinant androgen receptor (AR) cassette, the recombinant AR cassette containing an exogenous polyglutamine (polyQ) tract encoding sequence in mouse exon 1 of said cassette, wherein the exogenous polyQ tract encoding sequence is stably integrated into the genome of the cell, fertilized egg or tissue and replaces an endogenous polyglutamine/histidine (polyQ/H) tract encoding sequence corresponding to amino acids 9 to 19 of the endogenous polyglutamine/histidine (polyQ/H) tract in exon 1 of mouse AR gene and expressing a recombinant AR polypeptide, wherein only the endogenous poly Q/H encoding tract is replaced and wherein the exogenous polyQ tract encoding sequence encodes 16 to 23 glutamine residues, optionally wherein the exogenous polyQ tract encoding sequence is contiguous CAG repeats.

4. The recombinant cell, fertilized egg or tissue of claim 3, wherein the recombinant cell is a stem cell optionally an embryonic stem cell or an induced pluripotent stem cell, a pancreatic cell, a prostate cell, a kidney cell, a hepatic cell, a mammary cell, or an ovarian cell.

5. The recombinant cell, fertilized egg or tissue of a claim 3, wherein the recombinant cell, fertilized egg or tissue is isolated from a recombinant polyQ AR knock-in mouse.

6. A polyglutamine (polyQ) androgen receptor (AR) knock-in mouse, expressing a recombinant AR polypeptide, the recombinant AR polypeptide comprising a mouse AR and an exogenous polyQ tract, wherein the exogenous polyQ tract replaces an endogenous polyglutamine/histidine (polyQ/H) tract corresponding to amino acids 9 to 19 of the endogenous polyglutamine/histidine (polyQ/H) tract encoded by a portion of exon 1 of mouse AR gene, wherein only the endogenous poly Q/H encoding tract is replaced and wherein the exogenous polyQ tract consists of 16 to 23 glutamine residues.

7. The polyQ AR knock-in mouse of claim 6, wherein the exogenous polyQ tract is encoded by contiguous CAG repeats.

8. The knock-in mouse of claim 6, wherein the mouse is a female mouse with altered androgen hormone levels, optionally wherein the hormone levels are altered surgically or by hormone replacement therapy or by diet.

9. The knock-in mouse of claim 6,
   a) wherein the knock-in mouse is a mouse model for metabolic syndrome, metabolic syndrome related liver disorder, optionally wherein the mouse model for metabolic syndrome related liver disorder develops non-alcoholic fatty liver disease (NAFLD), non-alcoholic steatohepatitis (NASH), liver cirrhosis and/or hepatocellular carcinoma (HCC), optionally an animal model for obesity, hypertension, Type 2 diabetes mellitus (T2D), prostate disease, and/or ovarian disease and accompanying infertility; optionally
   b) wherein the knock-in mouse is a mouse model for obesity and the mouse is optionally about 3 months to about 12 months of age and has an increased weight on average of at least 10%, at least 20% or at least 30% compared to control age matched mice lacking the recombinant AR cassette;
   c) wherein the knock-in mouse is a mouse model for hypertension and the mouse is about 3 months to about 12 months of age and has an increased systolic blood pressure of at least 5 mm Hg or an increased diastolic blood pressure of at least 5 mm Hg compared to control age matched mice lacking the recombinant AR cassette;
   d) wherein the knock-in mouse is a mouse model for T2D and the mouse is about 3 months to about 12 months of age, optionally wherein the knock-in animal has a fasting blood sugar level of 8 mmol/L or higher and/or a post-prandial blood sugar level of 11 mmol/L or higher or an increased blood sugar level compared to control age matched mice lacking the recombinant AR cassette;
   e) wherein the knock-in mouse exhibits hypertriglyceridemia and/or elevated LDL cholesterol levels compared to control age matched mice, and the mouse is about 3 months to about 12 months of age;
   f) wherein the knock-in mouse exhibits one or more of pancreatic hyperplasia, beta islet cell hyperplasia or insulin resistance, optionally wherein the mouse is about 3 months to about 12 months of age;

g) wherein the knock-in mouse is a mouse model for metabolic syndrome related liver disorders and develops non-alcoholic fatty liver disease (NAFLD), non-alcoholic steatohepatitis (NASH), liver cirrhosis and/or hepatocellular carcinoma (HCC);

h) wherein the knock-in mouse is a mouse model for a prostate disorder, and wherein the mouse is a male mouse; and/or i) wherein the knock-in mouse is a mouse model for ovarian disease and wherein the mouse is a female mouse.

10. The knock-in mouse of claim 6 or a recombinant cell, fertilized egg or tissue isolated therefrom or a recombinant cell line derived therefrom for identifying dietary effects, genetic alterations, macromolecules, metabolites or pathways involved in the initiation, evolution and/or progression of metabolic syndrome and/or a related liver disorder or prostate disorder, optionally wherein the recombinant cell or knock-in mouse is for use in a screening assay.

11. The construct of claim 1, wherein the exogenous polyQ tract encoding sequence is 18 to 21 contiguous CAG repeats.

12. The construct of claim 1, wherein the exogenous polyQ tract encoding sequence is 19 contiguous CAG repeats.

13. The recombinant cell, fertilized egg or tissue of claim 3, wherein the exogenous polyQ tract encoding sequence encodes 18 to 21 glutamine residues.

14. The recombinant cell, fertilized egg or tissue of claim 3, wherein the exogenous polyQ tract encoding sequence encodes 19 glutamine residues.

15. A recombinant cell, fertilized egg or tissue isolated or derived from the knock-in mouse of claim 6.

16. The knock-in mouse of claim 6, wherein the exogenous polyQ tract consists of 18 to 21 glutamine residues.

17. The knock-in mouse of claim 6, wherein the exogenous polyQ tract consists of 19 glutamine residues.

* * * * *